(12) United States Patent
Charneau et al.

(10) Patent No.: US 6,399,294 B1
(45) Date of Patent: *Jun. 4, 2002

US006399294B1

(54) NUCLEOTIDE SEQUENCES OF HIV-1 TYPE (OR SUBTYPE) O RETROVIRUS ANTIGENS

(75) Inventors: Pierre Charneau; François Clavel, both of Paris; Andrew Borman, Villemeux-sur-Eure; Caroline Quillent, Vitry sur Seine; Denise Guetard, Paris; Luc Montagnier, Le Plessis-Robinson; Jacqueline Donjon De Saint-Martin, Clamart; Jacques Cohen, Reims, all of (FR)

(73) Assignee: Institut Pasteur, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,441

(22) PCT Filed: Oct. 20, 1995

(86) PCT No.: PCT/FR95/01391

§ 371 (c)(1),
(2), (4) Date: Jul. 11, 1997

(87) PCT Pub. No.: WO96/12809

PCT Pub. Date: May 2, 1996

(30) Foreign Application Priority Data

Oct. 20, 1994 (FR) .............................. 94 12554
Mar. 3, 1995 (FR) ............................ 95 02526

(51) Int. Cl.$^7$ .......................... C12Q 1/70; A61K 39/21; C12N 7/00; C07H 21/04
(52) U.S. Cl. .................. 435/5; 424/188.1; 435/235.1; 530/324; 530/325; 530/326; 530/327; 530/328; 530/395; 536/23.72; 536/24.32
(58) Field of Search .............. 424/148.1, 160.1, 424/188.1, 208.1; 435/70.21, 172.2, 235.1, 339.1, 320.1, 449, 451, 452, 5; 530/388.35, 389.4, 395, 324–330; 536/23.72, 24.32

(56) References Cited

U.S. PATENT DOCUMENTS

| 5,030,714 A | 7/1991 | Alizon et al. |
|---|---|---|
| 5,304,466 A | 4/1994 | De Leys et al. |
| 5,352,576 A | 10/1994 | Haynes et al. ............ 435/5 |
| 5,567,603 A | 10/1996 | De Leys et al. |
| 5,759,770 A | 6/1998 | Guertler et al. |
| 5,770,427 A | 6/1998 | Guertler et al. |

FOREIGN PATENT DOCUMENTS

| AU | 7189394 | 1/1995 |
|---|---|---|
| EP | 0 284 587 | 9/1988 |
| EP | 0 290 893 | 11/1988 |
| EP | 0 330 359 | 8/1989 |
| EP | 0 471 407 | 2/1992 |
| EP | 0 657 520 A1 | 8/1993 |
| EP | 0 570 357 | 11/1993 |
| WO | 90 13564 | 11/1990 |
| WO | 94 29339 | 12/1990 |
| WO | 91 09869 | 7/1991 |
| WO | 92 05266 | 4/1992 |
| WO | 94 26298 | 11/1994 |
| WO | 94 28871 | 12/1994 |

OTHER PUBLICATIONS

Charneau, P., et al., "Isolation and envelope sequence of a highly divergent HIV–1 isolate: definition of a new HIV–1 group," *Virol.* 205(1):247–253 (Nov. 15, 1994).

Gürtler, L.G., et al., "A new subtype of Human Immunodeficiency Virus Type 1 (MVP–5180) from Cameroon," *J. Virol.* 68(3):1581–1585 (Mar. 1994).

Nkengasong J.N. et al., "Genomic Subtypes of HIV–1 in Cameroon," *AIDS* 8(10):1405–1412 (Oct. 1, 1994).

Van Den Haesevelde, M., et al., "Genomic cloning and complete sequence analysis of a highly divergent african Human Immunodeficiency Virus isolate," *J. Virol.* 68(3):1586–1596 (Mar. 1994).

Schable, C., et al., "Sensitivity of United States HIV antibody tests for detection of HIV–1 group 0 infections," *The Lancet* 344(8933):1333–1334 (Nov. 12, 1994).

*Primary Examiner*—Robert D. Budens
(74) *Attorney, Agent, or Firm*—Finnegan, Henderson, Farabow, Garrett & Dunner, L.L.P.

(57) ABSTRACT

An HIV-1 type (or subtype) O retrovirus protein, or a natural or synthetic polypeptide or peptide including at least a part of said protein, which is capable of being recognised by antibodies isolated from a serum resulting from infection by an HIV-1 type O VAU strain or an HIV-1 type (or subtype) O DUR strain.

11 Claims, 37 Drawing Sheets

| 1 | 2 | 3 | 4 | 5 | 6 | 7 | |
|---|---|---|---|---|---|---|---|
| 1 | 28 | 27 | 30 | 31 | 23 | 24 | |
|   |    |    |    |    |    | ■ | – gp160 (env) |
|   |    |    |    |    |    |   | – gp160 (env) |
|   |    |    |    |    |    | – | – p66 (RT) |
|   | –  | –  | –  | –  |    | ≡ | – p55 (gag) |
|   |    |    |    |    |    | ■ | – gp41 (env) |
|   |    |    |    |    |    | – |  |
|   | –  | –  | –  |    |    |   | – p32 (IN) |
|   | ■  | ■  | ■  | –  |    | ■ | – p24 (CA) |
|   |    |    |    |    |    |   | – p17 (MA) |

FIG. 2

```
                 SIGNAL PEPTIDE
VAU    1  ..MTAIMKAMGKRNRKLGIWCLILALIIPCL SCNQLYATVYSGVPVWEDA   48
          :..    . : ::..:|:|   .::::::: |  |..:.|:.|||  |||||.:|
LAI    1  MRVKEKYQHLWRWGWKWG..TMLLGILMICS ATEKLWVTVYYGVPVWKEA   48

VAU   49  KPTLFCASDANLTSTEQHNIWATQACVPTDPSPNEYELKNVTGKFNIWKN   98
          ..||||||||.  .||  ||:|||:|||||||.|.|  |  |||:.||:|||
LAI   49  TTTLFCASDAKAYDTEVHNVWATHACVPTDPNPQEVVLVNVTENFNMWKN   98

VAU   99  YIVDQMHEDIIDLWDQSLKPCVQMTFLCVQMNCTDIKNSINTTNSPLNSN  148
          :|:|||||||.|||||||||||:|  |||  :.|||:  |..||..|   ||.
LAI   99  DMVEQMHEDIISLWDQSLKPCVKLTPLCVSLKCTDLGNATNTNSSNTSS  148

VAU  149  NTK......EVKQCDFNVTTVLKDKQEKKQALFYVTDLVKINATSNETMY  192
          ...      |:|.|.||:..|  :::|   :|.  |:||   |:::.|:   .:.| |
LAI  149  SGEMMMEKGEIKNCSFNISTSIRGKVQKEYAFFYKLDIIPID..NDTTSY  196
```

FIG. 3A

```
VAU  193  RLINCNSTTIRQACPKVSFEPIPIHYCAPAGCAIFKCNETGFNGTGLCKN  242
          |..||...| ||||||||||||||||||||| ||:|||:..||||| |.|
LAI  193  TLTSCNTSVITQACPKVSFEPIPIHYCAPAGFAILKCNNKTFNGTGPCTN  246

VAU  243  VTVVTCTHGIKPTVSTQLILNGTLSKGNITIMGKNISDSGENILITLNTN  292
          |..| ||||||:|.||||||:|||.|..::..|.: |:.|.:..|:: ||.
LAI  247  VSTVQCTHGIRPVVSTQLLLNGSLAEEEVVIRSANFTDNAKTIIVQLNQS  296
                       V3 LOOP
VAU  293  ITIACERPGNQTIQKIMAGPMAWYSMALSNTKGDTRAAYCNYSATDWNKA  342
          :.|.||.||.|.| ..|. ...:   .:.   .. |: |.|.||.| ..||.
LAI  297  VEINCTRPNNNTRKSIRIQRGPGRAFVTIGKIGNMRQAHCNISRAKWNAT  346

VAU  343  LKNITERYLELVEYNQTDVTMKFGNHSGEDAEVTNFFFNCHGEFFYCNTN  392
          ||.|...:. | .: |.| :    | . ||:|:|:.. ||| |||||||..
LAI  347  LKQIASKLREQFGNNKTII...FKQSSGGDPEIVTHSFNCGGEFFYCNST  393

VAU  393  RLFNHTFSCKKNMTNNKINCTNISNNSNGTQAI..PCRLRQVVRDWMRGG  440
          .||| |:        |.. :|: |||.:|.:.| ||||::|.:. | .|
LAI  394  QLFNSTWF.......NSTWSTEGSNNTEGSDTITLPCRIKQFINMWQEVG  436
```

FIG. 3B

```
VAU  441  SGLYAPPIPGNLVCRSNITGMILQLDTPWNKTHPNSTTLPPGGGDMKDIW  490
          .::||||.|.: |.|||||::|  |.. |..  .|..:|||||||:| |
LAI  437  KAMYAPPISGQIRCSSNITGLLLTRDGGNNNN..GSEIFRPGGGDMRDNW  484
                                    GP120 ←——┬——→ GP41

VAU  491  RTQLFKYKVVRVKPFSVAPTKIARPTIGTRSHREKRAAGLAMLFLGILSA  540
          |.:|:|||||::.|::||||| |..:   :|||||.|:: ||||:|:|
LAI  485  RSELYKYKVVKIEPLGVAPTKAKRRVV....QREKRAVGIGALFLGFLGA

VAU  541  AGSTMGAAATALTVRTQHLIKGIVQQQDNLLRAIQAQQHLLRPSVWGIRQ  590
          ||||||  . |||...:|:..||||||:|||||:||||||. .||||:|
LAI  531  AGSTMGARSMTLTVQARQLLSGIVQQQNNLLRAIEAQQHLLQLTVWGIKQ  580
                    IMMUNODOMINANT EPITOPE
VAU  591  LRA⎡RLLALETFIQNQQLLNLWGCKNRLIC⎤YTSVKWNKTWGGDN.ESIWDE  639
          |.|⎢:||:| :::.:||||.:|||...:|||⎥ |.|.|| .|:... | ||::
LAI  581  LQA⎣RILAVERYLKDQQLLGIWGCSGKLIC⎦TTAVPWNASWSNKSLEQIWNN  630
```

FIG. 3C

```
VAU  640  LTWQQWDQQINNVSSFIYEKIQEAQEQQEKNEKELLELDEWASIWNWLDI  689
          :||  :||..:|||  .|:|..  |:|.|:||||||.||||||.|||:|||::|
LAI  631  MTWMEWDREINNYTSLIHSLIEESQNQQEKNEQELLELDKWASLWNWFNI  680

VAU  690  TKWLWYIKIAIIIVGALIGVRVVMIVLNLVKNIRQGYQPLSLQIPIQQQA  739
          |.|||||||  |:|||:|:|:|:  ||..:|..:||||  |||:|..:..
LAI  681  TNWLWYIKIFIMIVGGLVGLRIVFAVLSIVNRVRQGYSPLSFQTHLPTPR  730

VAU  740  EVGTPGGTGEGGGDEDRRRWTPLPQGFLHLLYTDLRTIILWIYHLLSNLA  789
          :.:  |:|..:|:||:  ||  |...|..|  |  |::.|||.:.|:  ||  |.:|
LAI  731  GPDRPEGIEEEGGERDRDRSIRLVNGSLALIWDDLRSLCLFSYHRLRDLL  780

VAU  790  SEIQKLIRHLGLGLWIIGQRTIEACRLFKAIIQYWLQELQTSATNLLDTV  839
          :  :::              ::|.|.  ||  :.:..::|||  |||..||..||:..
LAI  781  LIVTRIVE.......LLGRRGWEALKYWWNLLQYWSQELKNSAVSLLNAT  823

VAU  840  AVAVANWTDSTILGIQSIGRGILNIPRRIRQGLERLLL  877
          |:|||:  ||..|  .:|:  .|:|  :|||||||||||:||
LAI  824  AIAVAEGTDRVIEVVQGACRAIRHIPRRIRQGLERILL  861
```

FIG. 3D

```
HIV-1lai      RILAVERYLKDQQLLGIWGCSGKLIC
HIV-1Z321     -------------------------I--
HIV-1eli      -------------------------H--
HIV-1JRCSF    -V------------M-------------
HIV-1WMJ      -V--------R-----------------
HIV-1NDK      -V--------R-------------RH--
HIV-1mal      -V--------Q--R---M------H--
SIVCPZGAB     -L--------Q---I--L------AVvau           -L--L-TFIQN----NL---KNR---
mvp5180       -LQ-L-TLIQN--R-NL---K-----
ant70         -L--L-TL-QN----SL---K---V-

HIV-2rod      -VT-I-K--Q--AR-NS---AFRQV-
HIV-2D194     -VT-I-K-----AQ-NS---AFRQV-
```

FIG. 4

```
DNA SEQUENCE   2631 B.P.   ATGACAGCGATT ... CGACTCCTGTTA  LINEAR
            |         |         |         |         |         |         |         |         |         |
            10        20        30        40        50        60        70        80        90        100
   1  ATGACAGCGA TTATGAAAGC AATGGGGAAG AGGAACAGGA AGTTAGGGAT CTGGTGCTTG ATTTTGGCTT TGATAATCCC ATGTTTGAGC TGTAACCAAC
 101  TATATGCCAC AGTCTATTCT GGGTACCTG TATGGGAAGA TGCAAAACCA ACATTGTTCT GTGCTTCAGA TGCTAACTTG ACAAGCACTG AACAGCATAA
 201  TATTTGGGCA ACACAAGCCT GTGTTCCCAC AGACCCCAGT CCAAAATGAT ATGAGCTAAA AAATGTGACA GGTAAATTCA ATATATGGAA AAATTATATA
 301  GTAGACCAAA TGCACGAAGA CATTATAGAT TTGTGGGACC AGAGTTTAAA ACCTTGTGTT TCTTGTGTGT ACAAATGAAT TGTACAGATA
 401  TCAAAAATAG TATTAATACC ACAAACAGTC CCTTAAACTC AAACAATACA AAAGAGGTGA AACAGTGTGA CTTTAATGTA ACTACAGTGC TCAAAGACAA
 501  ACAGGAGAAA AAACAGGCTC TATTCTATGT GACAGATTTG GTTAAGATTA ACGCCACATC AAATGAAACA ATGTATAGAT TAATTAATTG TAACTCCACA
 601  ACCATCAGGC AGGCCTGTCC AAAGGTATCT TTTGAGCCCA TTCCCATACA CTATTGTGCT CCAGCGGGAT GTGCCATCTT TAAGTGTAAT GAAACAGGAT
 701  TTAATGGAAC AGTCTCTGT AAAAACGTTA CAGTAGTTAC TTGTACACAT GGCATCAAAC AACAGTAAG TACCCAACTA ATACTAAATG GGACACTCTC
 801  TAAAGGAAAT ATAACAATCA TGGGAAAGAA TATTTCAGAC AGTGGGAGA ACATCCTAAT AACCCTAAAT ACTAATATAA CAATAGCATG TGAGAGACCA
 901  GGAAATCAGA CAATACAAAA GATAATGGCA GTCCAATGG CTTGGTACAG AGTAATACAA AGGGGATAC AGGGCCAGCT TATTGTAATT
1001  ATAGTGCCAC TGACTGGAAC AAAGCCTTAA AAACATAAC TTAGAACTTG TAGAATATAA TCAAACTGAT GTTACCATGA AATTCGGTAA
1101  TCACAGTGTT GAAGATGCAG AAGTAACAAA TTTCTTTTTT AACTGTCATG GAGAATTCTT TTATTGTAAC ACAAATCGGC TGTTTAATCA TACCTTTCC
1201  TGCAAGAAGA ATATGACCAA TAACAGATCC AATTGTACTA ATATTAGCAA GGCACTCAGG CAATACCTTG CAGGTGAGA CAAGTAGTAA
1301  GGGACTGAT GAGGGAGGA TCGGGACTTT ATGCACCTCC CATCCCAGA GCAGTAGTAT GCACTCTGA ATGATTCTAC AATTGGACAC
1401  GCCATGGAAT AAAACACATC CTAACAGCAC AAATTGCAA CACCCTTAGA CCAGGAGGG GAGATATGAA AGAACTCAAT TGTTCAAATA TAAAGTAGTA
1501  AGAGTAAAAC CTTTTAGTGT AGCAAGAACA CTAAACTGGG AGAAAAGAGC TCTCATAGAG AGAAACTAGA GGCCAACTAT AGCAGGTTTG GCAATGCTAT
1601  TCTTGGGAT TCTAAGTGCA GCAGGAAGCA CTATGGCGCC AGCGGCAACA TACGACGG GCATCGATA AAGGGTATAG TGCAACAGCA
1701  GGATAACCTG CTAAGAGCAA TACAGCGCA GCAACACTTG CTGAGGCCT CTGTATGGGG ATTAGACAA CTCCGAGCTC GCCTGCTAGC CTTAGAAACC
1801  TTTATACAGA ATCAGCAACT CCTTAACCTG TGGGCTGCA AGAATAGACT ACATCAGTAA AGTGGAATAA AACATGGGA GGAGATAATG
1901  AATCAATTTG GGATGAGTTA ACATGGCAGC AGTGGGATCA ACAGATAAAC CCTTCATATA TGAAAAAATA CAAGAGGCAC AAGAACAACA
2001  GGAGAAAAT GAGAAAGAAT TGCTGGAGTT AGATGAATGG GCCTCTATTT TGACATAACT AAATGGTTGT GGTATATAA AATAGCTATA
2101  ATCATAGTAG GAGCACTAAT AGTTGTAAGA GTAGTTATGA TAGTACTTAA TCTAGTAAAG AACATTAGGC AGGGATATCA ACCCCTCTCG TTACAGATCC
2201  CCATCCAACA ACAAGCGGAA GTAGGAAACG CAGGAGAAAC AGGAGAAGGA GGTGGAGACG AAGACAGGCG CAGGTGGACT CCATTGCCGC AAGGGTTCTT
2301  GCATCTGTTG TACACGGACC TCAGGACCA AATCTTGTGG ATTTACCACC TCTTGAGCAA CTTAGCCTCA GAGATCCAGA AGTTGATCAG ACACCTGGGA
2401  CTTGGACTAT GGATCATAGG GCAGAGGACA ATCAGCAACT ATTGAAGCTT GCAGACTCTT TAAAGCTATA ATACAATACT GGCTACAAGA ATTGCAAACT AGTGCTACAA
2501  ATCTACTAGA TACTGTTGCA GTGGCAGTTG CTAATTGGAC TGACAGCACA TACAAAGCAT AGGGAGAGGG ATTCTTAACA TACCAAGAAG
2601  GATTAGACAG GGCCTTGAAC GACTCCTGTT A
            |         |         |         |         |         |         |         |         |         |
            10        20        30        40        50        60        70        80        90        100
```

FIG. 6

```
     1          10         20         30         40         50         60         70         80
              |          |          |          |          |          |          |          |
  1   GCAGAGACAG GACAGGAAAC TGCCTACTTC CTGTTAAAAT TAGCAGCAAG ATGGCCTATT AAAATACTAC ATACAGACAA
 81   TGGGCCTAAC TTTACAAGTG CAGCCATGAA AGCTGCATGT TGGTGGACAA ACATACAACA TGAGTTTGGA ATACCATACA
161   ATCCACAAAG TCAAGGAGTA GTAGAAGCCA TGAACAAGGA ATTAAAAATCA ATCATACAGG TGAGGGACCA AGCAGAGCAC
241   TTAAGGACAG CAGTACAAAT GGCAGTATTT GTTCACAATT TTAAAAGAAA AGGGGGATT GGGGGGTACA CTGCAGGAGA
321   GAGATTAATA GACATATTAG CATCACAAAT ACAAACAACA GAACTACAAA AACAAATTTT AAAAATTCAA AATTTTCGGG
401   TCTATTACAG AGACAGCAGA GACCCTATTT GGAAAGGACC GGCACAGCTC CTG
              |          |          |          |          |          |          |          |
             10         20         30         40         50         60         70         80
```

*FIG. 7*

GAG REGION

```
              #              # ##       #        #         #           #  #
    qgqmvhqgalsprtlnawvkaveekafnpeiipmfmalsegavpydinvmlnaiggghqgal
DUR ------------------------------------------------------------
ANT ----i-------------------------------is----t------------------
MVP ----i--------------------------------------t-----------------
LAI ----i-------v-------------s--v----s----t-q-l-t----tv----a-m
MAL -i--i-------vi------------s--v----s----t-q-l-m----iv----a-m
CPZ ----i-------v-------------s--v----s----l-q-v-t-------v-----m
```

*FIG. 8A*

```
                    #        #  # #     #          #  #
    qvlkevindeaadwdrahpqqagplppgqireptgsdiagttstqqeqilwttragnpip
DUR ------------------------------------------------------------
ANT -----e--ve---t--ppv------------------------------------h---pnq---
MVP -----e------e---t--pam------------------------------i---gans---
LAI --m---t---e---v--vh---ia---m--r-------------------l---g-m-nnp---
MAL --m-dt---e---v--vh---i---m--r-------------------l---g-m_snp---
CPZ -------e---e---l--th---ia---l--r-------------------l---g---np---
                         |||                                    |||
```

*FIG. 8B*

```
                  #  #        #                                #
     vgdiyrkwivlglnkmvkmyspvsildirqgpkepfrdyvvdrfyktlrae
DUR  ----------------------------------------------------
ANT  ----------------------------------------------------
MVP  ---------------------------------k------------------
LAI  --e--kr--i--i-r----t--------------------------------
MAL  ----kr--i--i-r--------------------------------------
CPZ  ---v--vi----v-r--

REGION OF THE V3 LOOP OF GP120

```
----YK-----QRTG-    ---Q-LY-  THR-I-DI  ------         MAD
CTRPNNNTRKSIRIQRGPGRAFVT IGK IGNM RQAHC               LAI
--------NR-S-   -------H--   TKQ-I-DI  ------         OYI
-A---YQ----QRTP-    -L-QSLY-  TR SRSII  G-----         ELI
----G-----RGIHF    ---QALY-  T---V-DI  -R-Y--         MAL
-S--Y-TRKNIRRYSI-S-QAFYV  T---I-DI  -Q----         455
--H--G----GE  VQI----MTFYN   -ENVV-DT  -S-Y--         CPZ

-E---QI DIQE  MRI--  M-WYSMG--GTA--S S---Y-         ANT
-I--EGIAEVQD--YT  -- MRWRSM TLIRSNNT S-V-Y-         MVP
-E--G-QTIQK-MA  ---  M-WYSMALSNTK-DT  -A-Y-         VAU
-V--G--SV-E-K-  ---  M-WYSMQ-EREGKGANS-T-F-         DUR

C*R**********I****GP M*W*SM**********SR*A*C HIV-O CONSENSUS
CVRPGNNSVKEIKI GP MAWYSMQIEREGKGANSRTAFC DUR
```

*FIG. 9A*

```
                    IMMUNODOMINANT REGION OF GP41
               [~~~~~~~~~~~~~~~~~~~~~~~~~~~~~~~~~~]
               [===================]
MAD            -V-------Q---------H----T----S----
LAI            RILAVERYLKDQQLLGIWGCSGKLICTTAVPWNASWS
OYI            -V--------------------T-------------
ELI            -------------------H----N----S------
MAL            -V----Q-R---M------H----F----S------
455            -V----Q-------------------T---------
CPZ            -L----Q---I--L-----AV-Y-T----N--P

ANT            -L--L-TL-QN----SL---K----V-Y-S-K--RT-I
MVP            -LQ-L-TLIQN--R-NL---K----Y-S-K--RT-I
VAU            -L--L-TFIQN----NL---KNR--Y-S-K--KT-G
DUR            -L--L-TLMQN----NL---R-A--Y-S-Q--ET-G

HIV-O CONSENSUS  RL*ALET**QNQQ*L*LWGC*****CYTSV*WN*TW*

DUR              RLLALETLMQNQQLLNLWGCRGKAICYTSVQWNETWG
                 [                                  ]
```

FIG. 9B

CAGGGACAAATGGTACATCAGGCCATCTCCCCCAGAACTTTATATGTATGGGTAAAGGCA
GTAGAAGAAAAGGCCTTTAACCCTGAAATTATCCCTATGTTTATGGCACTATCAGAAGGA
GCTGTTCCCTATGATATCAATGTTATGCTAAATGCCATAGGAGGACACCAAGGGGCTTTA
CAAGTATTAAAAGAAGTAATCAATGATGAAGCAGCAGACTGGGATAGAGCTCACCCACAA
CAGGCAGGGCCGTTACCACCAGGGCAGATAAGGGAACCAACAGAGAAGTGACATTGCTGA
ACAACTAGCACACAGCAAGAGCAAATTCTCGGACTACTAGGGCAGGTAACCCTATCCCA
GTTGGAGACATCTATAGGAAATGGATAGTGTTGGGTCTAAACAAAATGGTAAAAATGTAT
AGTCCAGTGAGCATCTTAGATATTAGGCAGGAGCCAAAAGAACCATTTAGAGATTATGTA
GACAGGTTCTACAAAACATTAAGAGAGCTGAGCAG

GAG REGION OF HIV1-O DUR STRAIN: 513 BASE PAIRS

= SEQ ID N° 9

FIG. 10A

QGQMVHQALSPRTLNAWVKAV

```
ATTCCAATACACACTATTGTGCTCCAGCAGGATATGCTATCTTTAAATGCAACAACGAGGAG
TTTACTGGAAAAGCCCATGTAACACATTCAGTAGTTCAGTTACCTGTACACAGGTATCAAG
CCAACAGTAAGCACTCATCATCTAATATTCAATGGACAATCTCTGAAAGAAGAATAAGAATT
ATGGGAAAGAACATCTCGAGCAACTCAGTAATATCCTAGTGACCCTAAATTCTACTATA
AACATGACCTGTGTGAGGCAGGAAATTGAGCGAGAGGAAAAATCAGTACAGGAGATAAAATAGTCCAATG
GCTTGGTACAGTATGCCACGGACTGGAGAAAAACCTTGCAAGGATAGCTGAAAGGTATTA
TGTACCTATAATGCCACGGACTCCGACTGAAATAATGTTCAATAAAAGCAATGGTGAGAT
GAACTTGTAAATAAAACAAGTCCGACTTTGCATTTTAACTGTCATGGAGAATTCTTT
GCAGAAATAACCCGTTTGCATTTTAACTGTCATGGAGAATTCTTT
```

V3 LOOP OF GP120 DUR STRAIN: 525 BASE PAIRS

= SEQ ID N° 10

FIG. 11A

IPIHYCAPAGYA

ATAGTGCAACAGCAGGACAACCTGCTGAGAGCAATACAGGCCCAGCAACATCTGCTGAGG
TTATCTGTATGGGGTATTAGACAACCCGAGCTCGCTGAGCCTTAGAGAAACCCTTATG
CAGAATCAGCAACTCCTAAACCTGTGGGGTTGTGAGAGGAAAAGCAATCTGCTACACATCA
GTACAATGGAATGAAACATGGGGAGGAAATGACTCAATTTGGGACAGGTTAACATGGCAG
CAATGGGATCAACAGATAGCCAATGTAAGCTCTTTTATATATGACAAAATACAAGAAGCA
CAAGAACAACAA

DNA SEQUENCE OF THE IMMUNODOMINANT REGION OF GP41 OF
HIV1-O DUR: 312 BASE PAIRS

= SEQ ID N° 11

FIG. 12A

IVQQQDNLLRAIQAQQHLLRLSVWGIRQLRARLLALETLMQNQQLLNLWGCRGKAICYTS
VQWNETWGGNDSIWDRLTWQQWDQQIANVSSFTYDKIQEAQEQQ

DNA SEQUENCE OF THE IMMUNODOMINANT REGION OF GP41 OF HIV1-O DUR - PREDICTED PROTEIN: 104 AMINO ACIDS

FIG. 12B

SPECIFIC PRIMERS OF THE HIV-O TYPE

| | |
|---|---|
| DUR V3a | ATT-CCA-ATA-CAC-TAT-TGT-GCT-CCA-3′ |
| DUR V3r | AAA-GAA-TTC-TCC-ATG-ACT-GTT-AAA-3′ |
| DUR 41a | GGT-ATA-GTG-CAA-CAG-CAG-GAC-AAC-3′ |
| DUR 41r | AGA-GGC-CCA-TTC-ATC-TAA-CTC-3′ |

FIG. 13A

POSITIONS OF THE PRIMERS:

IN HIV MVP5180

| | |
|---|---|
| dur V3a | 6896 TO 6919 |
| dur V3r | 7400 TO 7423 |
| dur 41a | 7934 TO 7957 |
| dur 41r | 8292 TO 8302 |

IN HIV ANT70

| | |
|---|---|
| dur V3a | 6896 TO 6920 |
| dur V3r | 7392 TO 7415 |
| dur 41a | 7917 TO 7940 |
| dur 41r | 8256 TO 8276 |

IN HIV1 VAU

| | |
|---|---|
| dur V3a | 640 TO 663 |
| dur V3r | 1138 TO 1161 |
| dur 41a | 1684 TO 1707 |
| dur 41r | 2026 TO 2046 |

FIG. 13B

| V3 | |
|---|---|
| HIV1-M CONSENSUS | NEGATIVE |
| HIV1-M MAL (AFRICAN) | NEGATIVE |
| HIV1-M CTV-CPZ (CHIMPANZEE) | NEGATIVE |
| HIV1-O MVP5180 | NEGATIVE |
| HIV1-O ANT70 | POSITIVE |

FIG. 14A

| GP41 | |
|---|---|
| HIV1-M CONSENSUS: | |
| -PASTEUR STANDARD | NEGATIVE |
| -INNOGENETICS RIGHT-EXTENDED | WEAK POSITIVE |
| HIV1-O MVP5180: | |
| -INNOGENETICS | NEGATIVE |
| -BEHRING LEFT-EXTENDED | POSITIVE |
| HIV1-O VAU | POSITIVE |

FIG. 14B

NUCLEOTIDE COMPARISONS

EXPRESSED AS PERCENTAGE DIFFERENCE

GP41 (OUT OF 330 BASES)

| | LAI | MAL | CPZ | MVP5180 | ANT70 | VAU | DUR |
|---|---|---|---|---|---|---|---|
| LAI | 0 | | | | | | |
| MAL | 11 | 0 | | | | | |
| CPZ | 33 | 31 | 0 | | | | |
| MVP5180 | 39 | 38 | 38 | 0 | | | |
| ANT70 | 36 | 39 | 37 | 15 | 0 | | |
| VAU | 39 | 38 | 38 | 14 | 14 | 0 | |
| DUR | 38 | 36 | 37 | 13 | 15 | 11 | 0 |

*FIG. 15A*

V3 (OUT OF 558 BASES)

| | LAI | MAL | CPZ | MVP5180 | ANT70 | VAU | DUR |
|---|---|---|---|---|---|---|---|
| LAI | 0 | | | | | | |
| MAL | 19 | 0 | | | | | |
| CPZ | 37 | 34 | 0 | | | | |
| MVP5180 | 46 | 43 | 45 | 0 | | | |
| ANT70 | 45 | 44 | 43 | 23 | 0 | | |
| VAU | 44 | 41 | 41 | 24 | 24 | 0 | |
| DUR | 46 | 43 | 42 | 25 | 22 | 24 | 0 |

FIG. 15B

GAG (OUT OF 520 BASES)

| | LAI | MAL | CPZ | MVP5180 | ANT70 | DUR |
|---|---|---|---|---|---|---|
| LAI | 0 | | | | | |
| MAL | 9 | 0 | | | | |
| CPZ | 21 | 25 | 0 | | | |
| MVP5180 | 24 | 26 | 25 | 0 | | |
| ANT70 | 25 | 25 | 24 | 10 | 0 | |
| DUR | 25 | 26 | 25 | 9 | 10 | 0 |

FIG. 15C

PROTEIN COMPARISONS

EXPRESSED AS PERCENTAGE DIFFERENCE

GP41 (OUT OF 109 AMINO ACIDS)

| | LAI | MAL | CPZ | MVP5180 | ANT70 | VAU | DUR |
|---|---|---|---|---|---|---|---|
| LAI | 0 | | | | | | |
| MAL | 17 | 0 | | | | | |
| CPZ | 33 | 28 | 0 | | | | |
| MVP5180 | 42 | 40 | 41 | 0 | | | |
| ANT70 | 42 | 45 | 39 | 22 | 0 | | |
| VAU | 44 | 47 | 45 | 19 | 21 | 0 | |
| DUR | 44 | 42 | 39 | 17 | 17 | 14 | 0 |

*FIG. 16A*

V3 (OUT OF 186 AMINO ACIDS)

| | LAI | MAL | CPZ | MVP5180 | ANT70 | VAU | DUR |
|---|---|---|---|---|---|---|---|
| LAI | 0 | | | | | | |
| MAL | 31 | 0 | | | | | |
| CPZ | 46 | 39 | 0 | | | | |
| MVP5180 | 55 | 50 | 59 | 0 | | | |
| ANT70 | 55 | 50 | 55 | 36 | 0 | | |
| VAU | 55 | 51 | 55 | 39 | 36 | 0 | |
| DUR | 56 | 51 | 56 | 39 | 35 | 42 | 0 |

FIG. 16B

GAG (OUT OF 174 AMINO ACIDS)

| | LAI | MAL | CPZ | MVP5180 | ANT70 | DUR |
|---|---|---|---|---|---|---|
| LAI | 0 | | | | | |
| MAL | 6 | 0 | | | | |
| CPZ | 11 | 14 | 0 | | | |
| MVP5180 | 21 | 23 | 18 | 0 | | |
| ANT70 | 21 | 24 | 19 | 6 | 0 | |
| DUR | 22 | 22 | 19 | 7 | 9 | 0 |

FIG. 16C

CHROMATOGRAPHIC RESULTS

| RETENTION TIME (MIN) | INITIAL TIME (MIN) | FINAL TIME (MIN) | % SURFACE AREA | INT TYPE |
|---|---|---|---|---|
| 24.482 | 23.898 | 24.932 | 100.00 | BB |

*FIG. 18B*

VAU PEPTIDE

REF: F VAU 0994 C 710

SEQUENCE: RLLALETFIQNQQLLNLWGCKNRLICYTSVKWNKT

LENGTH: 35

MOLECULAR WEIGHT: 4210

ANALYTICAL CONTROLS: > 95% BY HPLC AND MASS SPECTROMETRY

FIG. 19B

STUDY OF THE IMMUNOREACTIVITY OF THE PEPTIDE MIMICKING THE IMMUNODOMINANT EPITOPE OF THE GP160 VAU SEQUENCE (SUBTYPE O)

| VS=0.1 RATIO | VAU PEPTIDE 2µg/ml |
|---|---|
| HIV1 SERA (PANEL BBI) | |
| BO1 NO° 12 | 0.80 |
| BO1 NO° 13 | 0.40 |
| BO1 NO° 15 | 0.80 |
| PRB911K6 | 0.20 |
| HIV1 SERA (ROMANIA) STAGE 3/4 | |
| 3989 | 9.50 |
| 5116 | 8.60 |
| HIV1 SERA (PANEL AFM) SUBTYPE O | |
| MAA | >30 |
| LOB | >30 |
| HAM | >30 |
| DUR | 12.50 |
| HIV1 SERUM (REIMS) SUB TYPE M? | |
| MAD | 0.20 |

FIG. 20A

| SUSPICION OF SUBTYPE O (YAOUNDE PASTEUR CENTER) | |
|---|---|
| | 0.60 |
| 3372 | >30 |
| 3361 | 28.80 |
| 1507 | 28.70 |
| 3167 | >30 |
| 2628 | 28.10 |
| 1060 | 0.60 |
| 4020 | 0.30 |
| 4783 | 0.30 |
| 5322 | 0.40 |
| 6661 | 0.50 |
| 5527 | 0.30 |
| 5863 | 25.00 |
| 5969 | >30 |
| 6487 | >30 |
| 6509 | 0.70 |
| 6782 | >30 |
| 5453 | 27.30 |
| 3826 | 1.50 |
| HIV2 SERA | |
| BERT | 0.30 |
| PAOL | 4.50 |
| RIV | 15.80 |

INDIRECT EIA PROCEDURE; 3 X 30 MIN TYPE GENELAVIA MIXT

FIG. 20B

| NEGATIVE SERA | |
|---|---|
| N=48 AVERAGE | 0.022 |
| DS AVERAGE | 0.007 |
| +12DS | 0.107 |
| VS | 0.100 |

FIG. 20C

SUMMARY OF THE RESULTS OBTAINED ON THE AFRICAN SERA

| | WB1 RESULTS | | | | | | | | | |
|---|---|---|---|---|---|---|---|---|---|---|
| | GP 160 | GP 120 | P 68 | P 55 | GP 41 | P 40 | P 34 | P 25 | P 18 | |
| 3361 | ++ | +- | + | | | | ++ | + | + | POS |
| 1507 | + | +- | | | | | +- | +- | | POS |
| 2628 | +- | | ++ | ++ | | + | + | ++ | ++ | POS |
| 3167 | ++ | + | ++ | ++ | + | + | ++ | ++ | ++ | POS |
| 3372 | ++ | +- | + | ++ | + | + | ++ | ++ | +- | POS |
| 5453 | ++ | +- | + | + | +- | + | + | + | + | POS |
| 5863 | ++ | +- | + | + | +- | +- | + | + | + | POS |
| 5969 | +-- | | + | + | | + | + | + | | IND |
| 6487 | ++ | | + | + | | | + | +- | +- | IND |
| 6782 | ++ | | + | + | + | + | + | + | | POS |
| 950 | +- | | +- | | | | +- | +- | +- | IND |
| 1060 | +- | | | | | | | +- | + | IND |
| 5527 | | | | | | | | | | ? |
| 6509 | ++ | | +- | | | | +-- | | | IND |
| 6661 | + | | | | | | | + | | IND |
| 4020= SEMT | + | | | | | | | (+-) | | IND |
| 4783= 5322 | +- | | | | | | | +- | +- | IND |
| 3826 | | | | | | | | +- | +- | IND |
| MAD | ++ | + | + | + | + | + | + | + | + | POS |
| DUR MAA LOB HAM | + | | ++ + | +- | | | ++ + | ++ + | | IND IND |

| =RATIO<1 |
|---|
| =RATIO>2 |

FIG. 21A

|  | TEST DE SCREENING (RATIO : DO/VS) | | | |
|---|---|---|---|---|---|
|  |  | GEM IND HIV1+2 | ABBOTT SDW HIV1+2 | MUREX SDW HIV1+2 |  |
| 3361 | 0.10 | 18.00 | 0.56 | 0.72 | 1.40 |
| 1507 | 0.97 | 14.25 | 3.03 | 5.35 | 0.98 |
| 2628 | 0.70 | 18.00 | 4.84 | 1.71 | 1.34 |
| 3167 | 0.38 | 18.30 | 11.89 | >6 | 0.88 |
| 3372 | 0.19 | 16.80 | 11.63 | 3.76 | 0.47 |
| 5453 | 2.50 | >20 |  |  | 1.70 |
| 5863 | 2.30 | >20 |  |  | 1.90 |
| 5969 | 2.30 | 15.20 |  |  | 2.25 |
| 6487 | 0.32 | 19.70 |  |  | 1.90 |
| 6782 | 0.07 | 13.40 |  |  | 2.95 |
| 950 | 1.20 | 6.00 | 5.76 | >6 | 0.68 |
| 1060 | 0.60 | 18.00 | 0.46 | 1.25 | 0.67 |
| 5527 | 0.27 | 2.40 |  |  | 0.52 |
| 6509 | 0.32 | >16 |  |  | 2.14 |
| 6661 | 8.10 | 10.10 |  |  | 1.54 |
| 4020= SEMT | 0.23 | 6.30 | 1.03 | 4.98 | 4.12 |
| 4783= 5322 | 0.19 | 8.10 10.90 | 0.41 |  | 0.55 0.52 |
| 3826 |  | 3.93 |  | 1.64 | 0.72 |
| MAD | - | + | + |  |  |
| DUR MAA |  | >8 | 2.00 | 0.80 |  |
| LOB | | >19 | 2.00 | 2.70 | 1.50 |
| HAM | | >19 | 1.80 | 7.80 | 2.70 |

FIG. 21B

|  | EIA PEPTIDES | | | | | | | |
|---|---|---|---|---|---|---|---|---|
|  | CLONATEC RAP HIV1 | 39D6 HIV1B | FER HIV1B | 39A HIV1B | VAU HIV1O | MVPP 5180 HIV1O | BNR 19 HIV1O | PEPTI-LAV1-2 |
| 3361 | + |  |  |  | 28.8 | 25.80 | NT |  |
| 1507 | DUBIOUS |  |  | 8.4 | 28.7 | 28.80 | 1.7 |  |
| 2628 |  |  |  | 3.6 | 28.1 | 19.30 | 1.2 |  |
| 3167 | + |  |  | >30 | >30 | >30 | 1.6 |  |
| 3372 | +- |  |  | 2.8 | >30 | 24.00 | 4.9 |  |
| 5453 | - | 4.36 | 1.37 | 3.6 | 27.3 |  | 1.6 | - |
| 5863 | - | 1.42 | 0.40 | 1.4 | 25 |  | 0.5 | - |
| 5969 | - | 0.94 | 1.90 | 19.4 | >30 |  | 0.6 | + |
| 6487 | + | 25.75 | 5.76 | >30 | >30 |  | 0.7 |  |
| 6782 | - | 0.64 | 0.49 | 0.8 | >30 |  | 10.3 | - |
| 950 |  |  |  |  | 0.6 |  | 0.4 |  |
| 1060 | DUBIOUS |  |  | 1.9 | 0.6 | 0.40 | 0.6 |  |
| 5527 | - |  |  | 4.5 | 0.3 |  | 0.2 | +/- |
| 6509 | + |  |  | 16.9 | 0.7 |  | 0.2 |  |
| 6661 | + |  |  | 2.8 | 0.5 |  | 0.4 |  |
| 4020= SEMT | ?Ag- |  |  | 1.15 1.2 | 0.3 0.7 |  | 0.5 0.9 |  |
| 4783= 5322 |  |  |  | 2.5 4 | 0.3 0.4 |  | 0.3 0.3 |  |
| 3826 |  |  |  | 1.6 | 1.5 |  | 0.7 |  |
| MAD |  | 0.66 | 2.72 | 26.7 | 0.2 |  | >30 | - |
| DUR |  | >30 | >30 | >30 | 12.5 |  | 0.2 |  |
| MAA |  |  |  | NT | >30 |  | NT |  |
| LOB |  | 1.02 | 5.62 | 12.5 | >30 |  | >30 |  |
| HAM |  | 0.73 | 0.41 | 13.3 | >30 |  | 0.7 |  |

FIG. 21C

NUCLEOTIDE SEQUENCES OF HIV-1 TYPE (OR SUBTYPE) O RETROVIRUS ANTIGENS

This application is the National Stage Application filed under 35 U.S.C. § 371 of International Application No. PCT/FR95/01391, filed Oct. 20, 1995.

The invention relates to the antigens obtained by expression of nucleotide sequences or by chemical synthesis, for example using *Applied Biosystems* brand synthesizers, present in HIV-1 group (or subgroup) O variants and more particularly the antigens corresponding to those which may be isolated from viral particles. By way of example of HIV-1 viruses of the subgroup O, reference is made to the HIV-1$_{(VAU)}$ isolate and to the HIV-1$_{(DUR)}$ isolate.

The invention also relates to monoclonal or polyclonal antibodies induced by these antigens.

The invention also relates to cloned DNA sequences either having sequence analogy or complementarity with the genomic RNA of the abovementioned virus. The invention also relates to processes for the preparation of these cloned DNA sequences. The invention also relates to polypeptides containing amino acid sequences coded for by the cloned DNA sequences.

Furthermore, the invention relates to applications of the antigens mentioned above to the in vitro detection in at-risk individuals of certain forms of AIDS and, as regards some of them, to the production of immunogenic compositions and vaccinating compositions against this retrovirus. Similarly, the invention relates to applications of the abovementioned antibodies for the same purposes and, for some of them, to their application to the production of active principles for medicinal products against this human AIDS.

The invention also relates to the application of the cloned DNA sequences and of the polypeptides obtained from these sequences as probes or primers for gene amplification, in diagnostic kits.

The invention also relates to antigenic compositions which may be obtained by chemical synthesis or by expression in a recombinant cell host and which allow the diagnosis of an infection due to a human retrovirus of HIV type independently of the HIV-1 or HIV-2 subtype. Such compositions comprise at least one peptide chosen from the antigenic peptides common to the HIV-1, HIV-2, HIV-1$_{(DUR)}$ and HIV-1$_{(VAU)}$ viruses or variants of the antigenic peptides possessing similar immunogenic characteristics.

The invention is also directed toward compositions which allow the specific diagnosis of an infection due to a human retrovirus of HIV-1 type, more particularly HIV-1, group M, HIV-2 or HIV-1 group (or subgroup) O and comprising at least one antigenic peptide specific for the HIV-1 virus, an antigenic peptide specific for the HIV-2 virus and an antigenic peptide specific for the HIV-1 group (or subgroup) O virus or variants of these antigenic peptides possessing similar immunogenic characteristics. More particularly, the antigenic peptides are derived from the envelope protein of HIV-1 group M and HIV-2 and HIV-1 group (or subgroup) O viruses.

The invention is moreover directed toward a peptide allowing detection of anti-HIV antibodies which the peptides of the prior art did not always make it possible to detect, based in particular on the discovery of a new HIV-1 strain: HIV-1 DUR. The antiserum directed against it does not always have reactivity with the peptides of the consensus HIV as it is used nowadays. The term "consensus HIV" refers to the regions which are conserved between isolates and whose demonstration is essential to the design of diagnostic reagents or vaccines, and whose mutations impart resistance to antiviral medicinal products. The term "peptide" used in the present text defines both oligopeptides and polypeptides.

STATE OF THE ART

Two types of human immunodeficiency virus (HIV) which have responsibility for the development of an LAS or AIDS have been isolated and characterized. A first virus, known as LAV-1 or HIV-1, was isolated and described in GB patent application 8324,800 and patent application EP 84401,834 of Sep. 14, 1984. This virus was also described by F. Barré-Sinoussi et al. in Science (1983), 220, 868–871.

The type 2 HIV retrovirus belongs to a separate class and has only a limited immunological relationship with type 1 HIV retroviruses. HIV-2 retroviruses have been described in European patent application No. 87,400,151,4 published under the number 239,425.

The HIV-1 retrovirus is the most common and its presence is predominant in several regions worldwide. As regards the HIV-2 retrovirus, it is most often found in West Africa, although its propagation outside this region has recently been documented by Grez et al., (1994) J. Virol. 68, 2161–2168.

The totality of primate immunodeficiency lenti-viruses, comprising the type 1 and type 2 human immuno-deficiency viruses as well as several types of non-human primate viruses, is increasing in size and complexity. The most common of these viruses, HIV-1, is currently spreading in the form of a worldwide epidemic and is responsible for a major public health problem. Shortly after the identification and molecular characterization of this virus, it was recognized as being highly variable, and currently comprises several subtypes (Myers, 1994, Louwagie, et al. 1993, Louwagie et al. 1992, Myers, G. (1994) HIV-1 subtypes and phylogenetics trees. In: Human Retrovirus and AIDS 1994; Myers, G., Korber, B., Wain-Hobson, S., Smith, R. F. and Pavlakis, G. N., Eds. Los Alamos National Laboratory, Los Alamos, N.M. III-2–III-9.). This differentiation of subtypes is mainly based on the divergence of the gag and env genes. At least 6 subtypes have been identified, designated A to F, but several are still likely to emerge from the ongoing extensive worldwide survey on the isolates of HIV-1. It has been found that these various subtypes are equidistant from each other, in a phylogenetic profile termed star phylogeny, which suggests that the various HIV-1 subtypes might have evolved and diverged synchronously from a common ancestor.

Recently, two separate viruses of this group of HIV-1 viruses were isolated and characterized. These two viruses were obtained from patients living in Cameroon, in West Central Africa (Gürtler, et al. 1994, Vanden Heasevelde, et al. 1994). Their sequence, more particularly the sequence of their env (envelope) gene, shows clearly that these viruses belong to a separate category of HIV-1-related viruses, referred to as HIV-1 group O (Nkengasong et al., 1993).

However, the diversity of the isolates within this group of HIV-1-related viruses is not known, and its propagation outside Africa has not been documented.

A general constraint, in the development of HIV serological tests, is to avoid both falsely positive—or falsely negative—results while at the same time retaining or improving the sensitivity in terms of detection of seropositivity which the previous tests allow.

Tests based on the use of consensus peptide(s), essentially derived from the "env" gene, were considered as an almost ideal solution until the discovery of the HIV-1-O variant brought to light the possibility of falsely negative results (Genomic cloning and complete sequence analysis of a highly divergent African human immunodeficiency virus isolate. J. Virol. 1994; 68: 1586–96; a new subtype of human immunodeficiency virus type 1 (MPV-5180) from Cameroon. J. Virol. 1994; 68: 1581–85).

The non-reactivity of certain tests with "env" peptide antigen, in patients nonetheless exhibiting certain clinical syndromes characteristic of AIDS or lymphadenopathy syndromes which occasionally precede them, is, at the present time, occasionally attributed to an infection of the HIV-1-O group (HIV-1/HIV-2 seronegativity in HIV-1 subtype O infected patients, Lancet 1994; 343: 1393–94; New HIV-1 subtype in Switzerland. Lancet 1994; 344: 270–71).

BRIEF DESCRIPTION OF THE DRAWINGS

This invention will be more fully described with reference to the drawings in which:

FIG. 2 is a Western blot analysis of a series of serum samples.

FIGS. 3A–D show an amino acid alignment of the HIV-1$_{VAU}$ and HIV-1$_{LAI}$ envelope sequences (SEQ ID NO:102 and SEQ ID NO:103), including an alignment of HIV-1$_{VAU}$ and HIV-1$_{LAI\ gp}$120 sequences (SEQ ID NO:46 and SEQ ID NO:48) and HIV-1$_{VAU\ and\ HIV}$-1$_{LAI}$ gp41 sequences (SEQ ID NO:47 and SEQ ID NO:49).

FIG. 4 is a multiple alignment of the immunodominant peptides in the extracellular segment of the transmembrane envelope glycoprotein of various HIV-1 isolates (SEQ ID NOs:50–62).

FIG. 6 is the DNA sequence of HIV-1$_{VAU}$ env gene (SEQ ID NO:63).

FIG. 7 is the DNA sequence of HIV-1$_{VAU}$ virus integrase gene (SEQ ID NO:64).

FIGS. 8A–C contain a comparison of the GAG amino acid sequence of various HIV-1 strains (SEQ ID NOs:65–70).

FIG. 9A is a multiple alignment of the V3 loop of gp120 (SEQ ID NOs:71, 73, 75, 77, 79, 81, 83, 85, 87, 89, 91, and 93).

FIG. 9B is a multiple alignment of the immunodominant region of gp41 (SEQ ID NOs:72, 74, 76, 78, 80, 82, 84, 86, 88, 90, 92, and 94).

FIG. 10A is a 513 base pair DNA sequence of the GAG region of HIV-1$_{DUR}$ (SEQ ID NO:95).

FIG. 10B is the corresponding 171 amino acid sequence of FIG. 10A (SEQ ID NO:96).

FIG. 11A is a 525 base pair DNA sequence of the V3 loop region of gp120 of HIV-1$_{DUR}$ (SEQ ID NO:97).

FIG. 11B is the corresponding 175 amino acid sequence of FIG. 11A (SEQ ID NO:98).

FIG. 12A is a 312 base pair DNA sequence of the immunodominant region of gp41 of HIV-1$_{DUR}$ (SEQ ID NO:99).

FIG. 12B is the corresponding 104 amino acid sequence of FIG. 12A (SEQ ID NO:100).

FIG. 13A shows specific primer sequences for HIV-1 type O (SEQ ID NOs:42–45).

FIG. 13B shows the corresponding positions of the primers of FIG. 13A in different HIV type O strains.

FIGS. 14A–B are serological correlation results.

FIGS. 15A–C are nucleotide comparisons of HIV sequences.

FIGS. 16A–C are protein comparisons of HIV sequences.

FIGS. 18A–B show an HPLC chromatogram of a VAU peptide.

FIGS. 19A–B show a mass spectroscopy analysis of a VAU peptide (SEQ ID NO: 101).

FIGS. 20A–C contain immunoreactivity data.

FIGS. 21A–C contain immunoreactivity data.

DESCRIPTION OF THE INVENTION

Figure 1A:
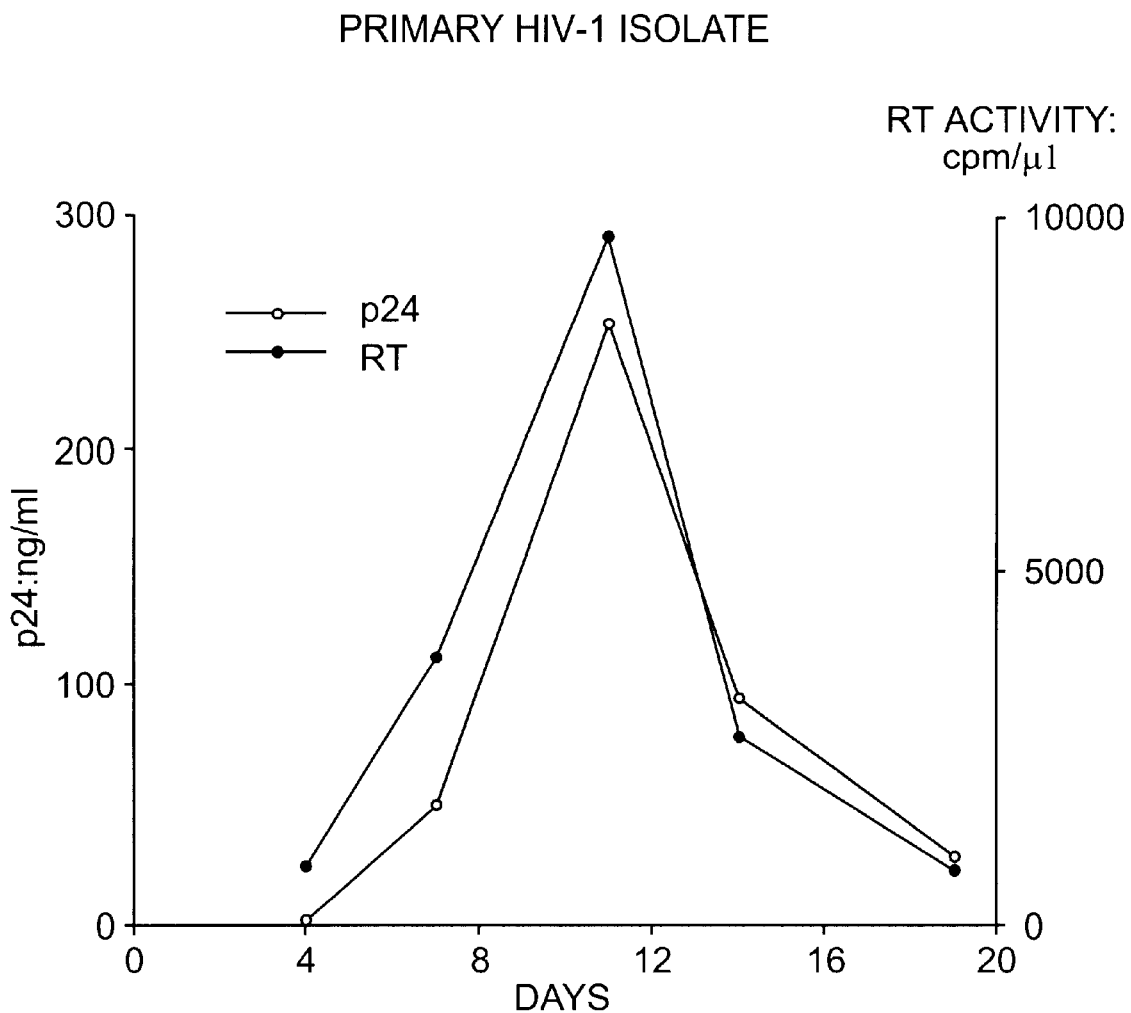
FIGS. 1A and B depict RT activity and p24 levels.

The aim of the present invention is to provide diagnostic laboratories with means, in particular specific peptides, allowing a detection of anti-HIV antibodies which were hitherto liable to be undetected. The invention also relates to mixtures of peptides obtained from HIV-1 DUR and of corresponding peptides from other HIVs, so as to avoid potential "false negative" results.

The invention moreover relates to a process of detection and of discrimination, in a biological sample, between antibodies characteristic of an HIV-1-M type retrovirus and antibodies characteristic of an HIV-1 group (or subgroup) O retrovirus.

The invention stems from observations made on a seropositive woman who had stayed in the Cameroon and who had revealed an atypical serological reactivity, in the course of several tests of screening for HIV infection, these tests having been confirmed by "Western blot" techniques.

On account of this atypical serological reactivity, in particular the lack of reactivity to certain third-generation tests, even modified for the O type, the inventors considered it interesting to carry out sequencing of certain parts of the genome of this HIV-1 DUR strain, more specifically of the GAG and ENV genes.

However, gene amplifications by PCR using primers obtained from the M group and known primers from the O group were unsuccessful for the parts coding for the V3 loop of gp120, and for the immunodominant region of gp41. Only the GAG region could be amplified using primers known in the prior art (Loussert-Ajaka I, Lancet 1994; 343: 1393). Another aim of the present invention is consequently to determine primers capable of overcoming this problem.

Partial sequences of the glycoproteins gp41 and gp120 were determined, along with capsid proteins (GAG gene), from lymphocyte DNA and from viral cultures, indicating that this HIV-1 DUR strain belongs in part to the HIV-1-O group, and that it differs considerably from the M group, more particularly as regards gp41 and gp120.

Thus, it was possible to demonstrate, more particularly as regards the GAG sequence of HIV-1$_{(DUR)}$, the existence of consensus sequences in the O group, in several regions, which are distinct from the consensus sequences of the M group in the same regions.

Cloning of the sequences coding for the GAG, gp41 and gp120 fragments of HIV-1$_{(DUR)}$ was carried out in a Bluescript® plasmid containing a PST1 site. The amplification products were cloned either according to the standard techniques using T3 and T7 universal primers, or directly sequenced by using the primers of the preceding amplification. The sequences were then determined with the Applied Biosystems 373A automated sequencer (ESGS Montigny le Bretonneux, France).

Within the context of the present invention, the inventors have isolated and sequenced the env gene from an O group isolate, HIV-1$_{(VAU)}$, obtained from a French patient who had never traveled outside Europe and who died of AIDS in 1992. According to its envelope sequence, HIV-1$_{(VAU)}$ is related to two recently characterized Cameroonian viruses HIV$_{ANT70}$ and HIV$_{MVP5180}$. Phylogenetic analysis of the env sequences reveals that the three viruses appear to constitute a separate group, which will be referred to herein as HIV-1 group O. The isolation of HIV-1$_{(VAU)}$ from this patient also indicates that a degree of propagation of HIV-1 group O has already occurred outside Africa.

Isolation of the HIV-1$_{(VAU)}$ Virus

HIV-1$_{(VAU)}$ was isolated in 1992 from a 41-year-old French patient suffering from AIDS. This patient exhibited, in 1986, a severe leuconeutropenia associated with a carcinoma of the uterine cervix. However, she gradually showed signs of opportunistic infections, with a reduction in the number of circulating CD4$^+$ T cells and she died of AIDS in 1992. Anti-HIV-1 antibodies were first detected by ELISA (Elavia, Sanofi Diagnostics Pasteur and Abbott test) in 1990.

The patient had never traveled outside Europe, had not used intravenous medicinal products and had not received any known blood transfusion. No sexual partner of African origin has been identified. She gave birth to a healthy child in 1971, but a son, born in 1980, died at the age of one following a clinical episode highly suggestive of neonatal AIDS. Her third child, born in 1983, and her husband are currently in good health and not infected.

The isolation of the virus was carried out in the following manner: the CD8$^+$ cells present in the PBMCs (peripheral blood lymphocytes) of the patient were removed using beads coated with IOT8 antibodies (Immunotech). These remaining PBMCs were stimulated with PHA, then cocultured with CD8-depleted PBMCs obtained from a healthy donor and stimulated with PHA. Viral growth in the coculture was monitored by assaying the reverse transcriptase (RT) activity of the supernatant and by ELISA test of the HIV-1 p24 (diagnostic kit marketed by DuPont de Nemours). The virus obtained from the initial coculture was subjected to several passages in CD8-depleted and PHA-stimulated PBMC cultures. Several attempts were made to infect, with the HIV-1$_{(VAU)}$, various transformed cell lines, including MT4 cells (Harada, et al. 1985) and CEM cells (Rey, et al. 1989), as well as the Hela-CD4-LTRLacZ cell line P4-2 (Clavel and Charneau 1994).

Biological Characterization of HIV-1$_{(VAU)}$

Figure 1B:
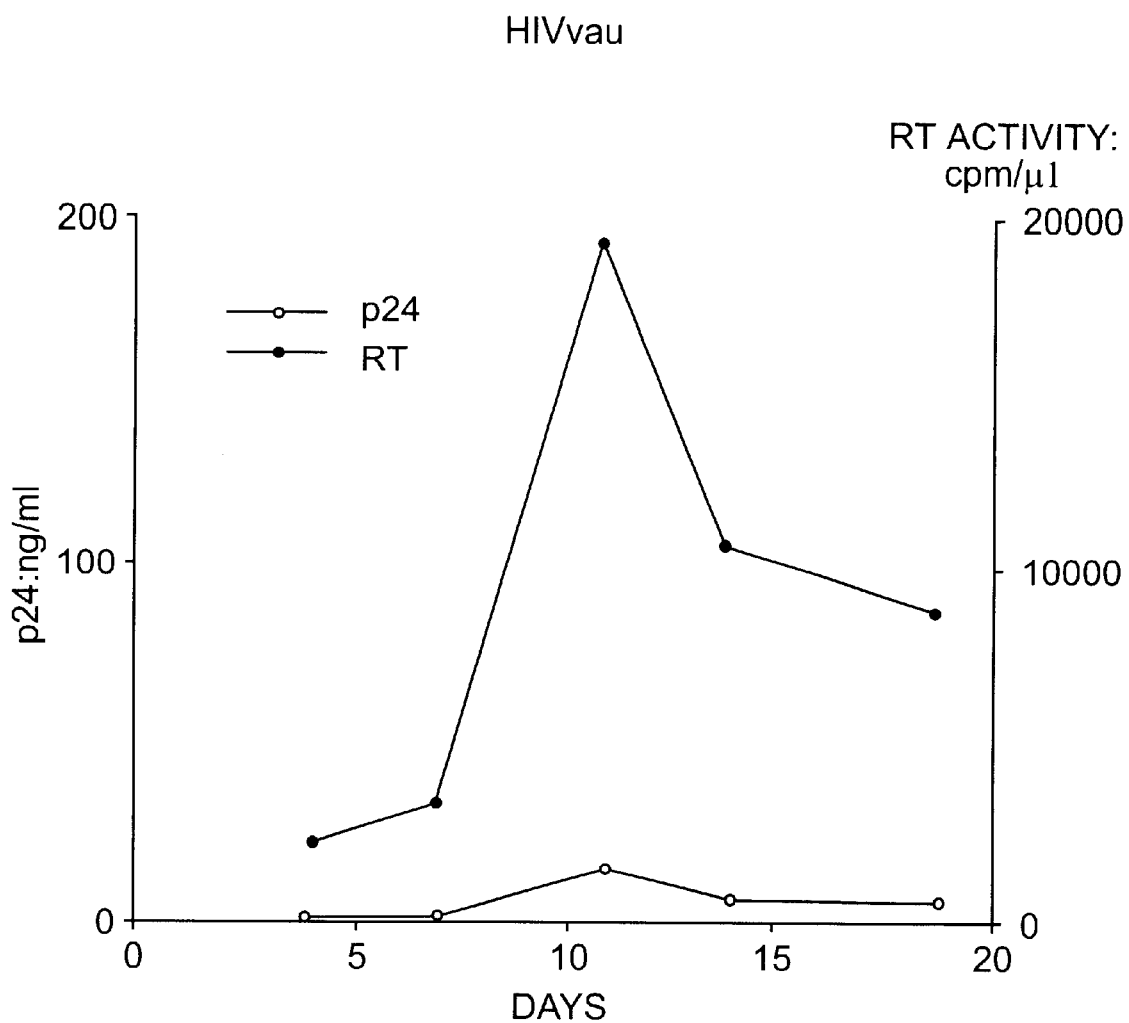

Two weeks after coculturing the patient's CD8-depleted, PHA-stimulated PBMCs with similar cells from a healthy donor, the production of virus was detected in the form of an RT activity peak in the culture supernatant. This virus could then be subjected to serial passages on CD8-depleted, PHA-stimulated normal PBMCs. FIG. 1A represents the production of HIV-1$_{(VAU)}$ in infected PBMC culture supernatants, checked by RT assay (filled circles) and HIV-1 p24 antigen capture ELISA (empty circles). The concentration of HIV-1 p24 is expressed in ng/ml and the RT activity in cpm/µl. In FIG. 1B, the same experiment was carried out with a standard primary HIV-1 isolate from an AIDS patient.

Although the growth of HIV-1$_{(VAU)}$ was easily detected by RT assay, the detection of virus in the culture supernatants by HIV-1 p24 ELISA (DuPont) was substantially less sensitive. FIG. 1 shows the comparison between the profiles of productive infection of PBMCs either with HIV-1$_{(VAU)}$ or with a primary HIV-1 isolate from an AIDS patient, assayed by RT or p24. For equivalent quantities of particles, determined by assay of RT activity in the supernatants assayed, approximately 25 times less p24 was detected in the case of HIV-1$_{(VAU)}$ than in the case of the other HIV-1 isolate. The difference may be due to the fact that the monoclonal antibody specific for HIV-1 p24, which is used to coat the ELISA plates, has only a weak affinity for the gag products of HIV-1$_{(VAU)}$.

Several negative attempts were made to propagate HIV-1$_{(VAU)}$ on transformed human T cell lines sensitive to HIV-1. In particular, cocultures between PBMCs infected with HIV-1(VAU) and either MT4 cells or CEM cells did not lead to propagation of the virus. It was also found that this virus was not capable of infecting CD4$^+$ HeLa cells (P4-2) (Clavel and Charneau 1994) carrying a lacZ gene inducible by the tat gene. Likewise, no replication of HIV-1$_{(VAU)}$ could be detected in activated peripheral blood lymphocytes from several chimpanzees.

Analysis of the HIV-1$_{(VAU)}$ envelope sequence, which will be described in detail later, and its comparison with that of the two recently described Cameroonian isolates indicate that all three viruses belong to the same group of HIV-1-related viruses. Furthermore, this comparison indicates that these three variants of the virus are approximately phylogenetically equidistant from each other. Consequently, each of the three virus variants constitutes on its own a distinct subtype of their group, which is now called HIV-1 group O. This group is different from the group of other HIV-1 isolates, identified up until now, which the inventors call here HIV-1, group M.

The appearance of this new group poses the question of its origin: did group O evolve from group M viruses (or conversely) or does each group have a different history? The inventors think that, insofar as both group M and group O have a similar internal divergence profile, it is likely that they each correspond to the diversification of distinct viral ancestors in distinct human populations. It is not possible to assess from the phylogenetic and virological data currently available whether the ancestor of either of the two groups affected humans naturally or was introduced into humans from other species. The only virus similar to HIV-1 present in a nonhuman primate is the SIVCPZGAB isolate (Huet, et al. 1990), isolated from a chimpanzee apparently infected naturally, which is clearly different both from group M and from group O, and for which no human equivalent has been found. It is unlikely that the group O viruses evolved recently from a chimpanzee virus insofar as HIV-1$_{(VAU)}$ has not succeeded in replicating in chimpanzee lymphocytes.

Why does the group O epidemic appear only now, some 15 to 20 years later than group M? There are three possible explanations: firstly, the introduction of the ancestor of the group O viruses into humans is thought to have occurred more recently than that of group M; secondly, it is possible that group M was allowed to spread earlier compared with group O because of different social conditions in their region of origin; and thirdly, the group O viruses could have a lower capacity for transmission compared with that of the group M viruses. It has been proposed that such a property explains the absence of significant worldwide propagation of HIV-2, for which a smaller viral load in infected subjects is linked to reduced transmissibility (De Cock, et al. 1993). In this regard, although no data are available on the viral load in patients infected with an HIV-1 group O, the pathogenicity of these viruses does not appear to be different from that of HIV-1. The patient from whom HIV-1$_{(VAU)}$ was isolated died of AIDS, like the patient from whom the HIV$_{MVP5180}$ group O isolate was obtained.

However, the natural history of infection of the HIV-1$_{(VAU)}$ patient is still not clear, but there are several indications that this patient was infected before 1980, as suggested by the death on that date of her second child suffering from a syndrome resembling AIDS.

The invention relates to any variant of the nucleic acid sequences of the HIV-1$_{(VAU)}$ virus or of any group O equivalent virus, containing structural proteins which have the same immunological properties as the structural proteins coded for by the env gene comprising the sequence described in FIG. 6 and called "vau", also designated by SEQ ID No:63.

The present invention also relates to compositions containing either antigens according to the invention, or a mixture of antigens according to the invention combined with extracts originating from one or more HIV-1 group O viruses or from other variant viruses, on the one hand, and from one or more HIV-2 and/or HIV-1 viruses, on the other hand, these compositions being optionally labeled. It is possible to use any type of appropriate label: enzymic, fluorescent, radioactive, etc.

Nucleic Acids

The invention relates to the DNAs or DNA fragments, more particularly cloned DNAs and DNA fragments, obtained from RNA, cDNA or primers which can be used in PCR, or other gene amplification methods, derived from the HIV-1$_{(VAU)}$ retrovirus RNA or DNA. The invention relates more particularly to all the equivalent DNAs, especially to any DNA having sequence homologies with the HIV-1$_{(VAU)}$ DNA, in particular with the sequence coding for for the env region of the HIV-1$_{(VAU)}$ strain comprising the sequence corresponding to SEQ ID No:63 represented in FIG. 6 and called "vau". The homology with HIV-1 group M is at least equal to 50%, preferably to 70% and still more advantageously to about 90%. Generally, the invention relates to any equivalent DNA (or RNA) capable of hybridizing with the DNA or RNA of a group O HIV-1 retrovirus.

The invention also relates to the RNA sequences corresponding to the DNA sequences defined above.

The invention also relates to the HIV-1$_{(VAU)}$ virus integrase gene comprising the sequence identified by the name SEQ ID No:64 or hybridizing with SEQ ID No:64. The invention also relates to the RNAs corresponding to the DNA described above.

The subject of the invention is also compositions containing the peptides or polypeptides encoded by the above-mentioned DNA or DNA fragments.

Oligonucleotides derived from the VAU sequence or alternatively from the HIV-1$_{(VAU)}$ virus integrase gene, particularly oligonucleotides comprising at least 9 nucleotides, may be used for the detection of group O HIV-1 virus DNA or RNA sequences in biological samples, cell cultures or cell extracts, by the PCR technique or any other gene amplification technique. These sequences could be used either as gene amplification primers or as probes for the specific detection of the gene amplification products. Also capable of being used as hybridization probes are the amplification products, or their corresponding synthetic sequence, obtained by chemical synthesis (Applied Biosystems).

The invention also covers any fragment of at least 100 nucleotides which may be used as a probe in hybridization reactions and capable of permitting reaction with part of the genome of an HIV-1$_{(VAU)}$ variant under high stringency hybridization conditions.

Cloning and Sequencing of the HIV-1$_{(VAU)}$ Env Gene

For the initial PCR amplification of the HIV-1$_{(VAU)}$ DNA, the total DNA was extracted from PBMCs infected with HIV-1$_{(VAU)}$ and a segment of the pol gene (integrase region) was amplified using degenerate primers:

primer 4506: 5'AGTGGAT(A/T)(T/C)ATAGAAGCAGAAGT3'; Seq. ID No. 1;

primer 5011: 5'ACTGC(C/T)CCTTC(A/C/T)CCTTTCCA3'; Seq. ID No. 2.

The reaction medium including 50 mM KCl, 10 mM Tris-HCl (pH 8.9), 1.5 mM MgCl$_2$, 0.1 mg/ml gelatin, 0.2 mM DNTP, 1U of Taq polymerase (Amersham). The PCR was carried out in 43 thermal cycles at 92° C. for 10 seconds, 50° C. for 1 minute and 72° C. for 40 seconds.

The resulting amplification product was cloned into a pBluescript vector, generating the clone ph4, deposited at the COLLECTION NATIONALE DES CULTURES DE MICRO-ORGANISMES (CNCM), Institut Pasteur, 28 rue du Docteur Roux, 75724 Paris Cedex 15, France, on Oct. 20, 1994 under No. I-1486, which was subsequently used as a probe to screen a lambda library of low molecular weight DNA, which was digested with EcoRI and was obtained from cells infected with HIV-1$_{(VAU)}$. Briefly, the PBMCs infected with HIV-1$_{(VAU)}$ were cocultured for 24 hours with new PBMCs stimulated with PHA and depleted of CD8$^+$ cells, after which a high cytopathic effect (CPE) was visible. The low molecular weight DNA was then extracted according to the Hirt method (Hirt 1967), and digested with the enzyme EcoRI. A previous Southern-blot analysis of this DNA had indeed shown that the HIV-1$_{(VAU)}$ genome contained only one EcoRI site, permitting the cloning of non-integrated circular DNA species representing the entire viral genome. The resulting digestion product was subjected to agarose gel electrophoresis, and the population of DNA fragments of approximately 8–12 kb in size was purified and ligated to EcoRI-digested lambda Zap DNA (Stratagene). After encapsidation, plating and screening by hybridization with $^{32}$P-labeled ph4 DNA, a clone, λH34, was identified as being positive, and amplified. The EcoRI insert was purified, sonicated, and cloned by the "shotgun" technique into the phosphatase-treated vector M13mp18 digested with the enzyme SmaI. One hundred and fifty of the clones obtained were sequenced in a 373A DNA sequencer (Applied Biosystems), and the resulting sequences were assembled into a single sequence using the Wisconsin GCG DNA analysis package.

Analysis of this sequence revealed numerous nonsense codons in all the reading frames, which is highly suggestive of a hypermutated genome (Vartanian, et al. 1991). This sequence being unusable, it was consequently decided to amplify, by PCR, the HIV-1$_{(VAU)}$ env gene using the total DNA from PBMCs infected with HIV-1$_{(VAU)}$, and the oligonucleotide primers derived from the sequence λH34:

primer TH2 5'GCTCTAGATGGGGATCTCCCATG-GCAGG3' Seq. ID No. 3;

primer UH2 5'GCTCTAGATCAGGGAAGAATCCCT-GAGTGT3'. Seq. ID No. 4.

The PCR amplification was carried out in 35 thermal cycles at 92° C. for 15 seconds, 52° C. for 1 minute, 60° C. for 2 minutes and 72° C. for 2 minutes. The resulting amplification product, of 3.5 kb in size, was cloned into the M13mp18 vector and sequenced by successive reactions, first using the M13 universal sequencing primer, and then the primers deduced from the upstream sequences. Analysis of the nucleotide and peptide sequences was carried out using the Wisconsin GCG DNA analysis package. The HIV-1$_{(VAU)}$ env gene codes for 877 amino acids in total, including the signal peptide. The nucleotide sequence of the HIV-1$_{(VAU)}$ env gene corresponds to Seq. ID No: 63 (see FIG. 3).

Use of Nucleic Acids as Probes

The invention also relates naturally to the use of DNA, CDNA or fragments thereof, or of recombinant plasmids or other equivalent vectors containing these fragments, as probes, for detecting the presence or otherwise of the HIV-1$_{(VAU)}$ virus in serum samples or other biological fluids or tissues obtained from patients suspected of being carriers of the HIV-1$_{(VAU)}$ virus. These probes are optionally labeled (radioactive, enzymic or fluorescent labels and the like). Probes which are particularly valuable for the implementation of the method for detecting the HIV-1$_{(VAU)}$ virus or an HIV-1$_{(VAU)}$ variant may be characterized in that they comprise all or a fraction of the DNA complementary to the HIV-1$_{(VAU)}$ virus genome or alternatively especially the fragments contained in various clones. An HIV-1$_{(VAU)}$ cDNA fraction containing all or part of the env region will be mentioned more particularly.

The probes used in this method for detecting the HIV-1$_{(VAU)}$ virus or in diagnostic kits are not in any way limited to the probes described previously. They comprise all the nucleotide sequences obtained from the genome of the HIV-1$_{(VAU)}$ virus, an HIV-1$_{(VAU)}$ variant or a virus similar by its structure, provided that they allow the detection, using biological fluids from individuals likely to have AIDS, of an HIV-1 group O virus, in particular HIV-1$_{(VAU)}$ by hybridization with the HIV-1$_{(VAU)}$ virus DNA or RNA.

Particularly advantageous are the probes which, when hybridized with HIV-1, give a strong reaction with HIVs belonging to group O and a weak reaction with HIVs belonging to group M. By way of nonlimiting example, a probe constructed from the HIV-1$_{(VAU)}$ virus integrase gene sequence (SEQ ID No:64) gives, when it is hybridized with HIV-1 under hybridization conditions such as those described in Patent EP 178 978, a strong reaction with group O HIVs and a weak reaction with group M HIVs.

The detection may be performed in any manner known per se, especially:

by bringing these probes into contact either with the nucleic acids obtained from cells contained in biological fluids (for example spinal fluid, saliva and the like), or with these fluids themselves, provided that their nucleic acids have been made accessible to hybridization with these probes, and this under conditions permitting hybridization between these probes and these nucleic acids, and by detecting the hybridization which may be produced.

The abovementioned diagnosis involving hybridization reactions may also be performed using mixtures of probes derived from HIV-1$_{(VAU)}$, HIV-1 and HIV-2 respectively, provided that it is not necessary to make a distinction between the desired HIV virus types.

The subject of the invention is also expression vectors containing the sequence coding for the HIV-1 envelope proteins or containing the sequence coding for the integrase.

The invention comprises compositions for detecting the presence or otherwise of the HIV-1$_{VAU}$ virus in serum samples or samples of other biological fluids or tissues, obtained from patients likely to be carriers of the HIV-1$_{VAU}$ virus. These compositions are characterized in that they comprise at least one probe obtained from a nucleotide sequence obtained or derived from the HIV-1$_{VAU}$ virus genome, particularly an HIV-1$_{VAU}$ DNA fragment containing the region or part of the region coding for for the env protein of the HIV-1$_{VAU}$ virus or of an HIV-1$_{VAU}$ variant.

Advantageously, the composition described above also comprises a probe obtained from a nucleotide sequence derived from HIV-1 or HIV-2.

Other diagnostic compositions comprise the primers of the invention which are capable of being used in gene amplification of subgroup O retroviruses or variants of these retroviruses.

Antigens, Especially Proteins and Glycoproteins

The invention relates to an HIV-1 group (or subgroup) O retroviral protein, or natural or synthetic peptide or polypeptide comprising at least a part of said protein, which is capable of being recognized by antibodies which may be isolated from serum obtained after an infection with an HIV-1 group O VAU strain, or an HIV-1 group O DUR strain.

The invention relates to an external envelope protein of the HIV-1$_{VAU}$ retrovirus encoded by the gene comprising the sequence corresponding to SEQ ID NO:65. According to a preferred embodiment of the invention, this protein is in addition characterized in that it comprises the amino acid sequence corresponding to Seq ID NO:46 represented in FIG. 3 and comprising amino acid residues 1 to 526. The subject of the invention is also any polypeptide or variant which is derived from said sequence having an epitope which may be recognized by antibodies induced by the HIV-1$_{VAU}$ virus.

The abovementioned protein may be obtained in a glycosylated or nonglycosylated form.

The subject of the invention is also an envelope transmembrane protein comprising the amino acid sequence SEQ ID NO:47 represented in FIG. 3 between amino acid residues 527 and 877. This transmembrane protein is, within the scope of the invention, in glycosylated or nonglycoslated form.

The invention relates to all the antigens, especially proteins, glycoproteins, polypeptides or peptides, obtained by expressing coding sequences of the HIV-1$_{(VAU)}$ genome and having immunological properties equivalent to those of HIV-1$_{(VAU)}$. The antigens are said to be equivalent within the scope of the present invention provided that they are recognizable by the same antibodies, especially antibodies which can be isolated from serum obtained from a patient who has been infected with an HIV-1$_{(VAU)}$.

In particular, the subject of the invention is the peptides or polypeptides which are synthesized chemically and whose amino acid sequence is contained in that of the HIV-1$_{(VAU)}$ envelope proteins, which sequence is represented in FIG. 3, or the equivalent peptides or polypeptides.

There should also be included among the equivalent peptides, polypeptides, proteins or glycoproteins, the fragments of the above antigens and the peptides which are prepared by chemical synthesis or by genetic engineering, so long as they give rise to immunological cross-reactions with the antigens from which they are derived. In other words, the invention relates to any peptide or polypeptide having epitopes which are identical or similar to the epitopes of the abovementioned antigens and which are capable of being recognized by the same antibodies. Forming part of this latter type of polypeptides are the products of expression of DNA sequences corresponding to DNA sequences coding for for the polypeptides or antigens mentioned above.

More particularly, the antigens which are obtained from the HIV-1$_{(VAU)}$ virus or produced by genetic engineering or conventional chemical synthesis, and which are of the greatest interest within the context of the present invention, are the antigens which make it possible to obtain a clear distinction between the HIV-1$_{(VAU)}$ viruses of the invention and the viruses of the HIV-1 and HIV-2 groups. In this regard, considerable differences have been observed at the level of the HIV-1$_{(VAU)}$ virus envelope protein as well as at the level of the immunodominant epitope of the external portion of the PM protein. It appears that the gag and pol proteins exhibit greater similarity with the HIV-1 virus than the envelope protein.

The invention also relates to peptides or polypeptides which are identical to the immunodominant region of the HIV-1$_{(VAU)}$ envelope transmembrane glycoprotein. This region is represented in FIG. 3.

Preferred polypeptides of this region are, for example, those which contain the sequence CKNRLIC (SEQ ID NO:5) or correspond to this sequence. They may also be peptides or polypeptides corresponding to the sequence RLLALETFIQNWWLLNLWGCKNRLIC (SEQ ID NO:6) or comprising this sequence.

Another preferred peptide, identified below by the name "VAU peptide", corresponds to the following sequence or comprises this sequence or any part of this sequence capable of being recognized by antibodies directed against the HIV-$1_{(VAU)}$ retrovirus RARLLALETFIQNQQLLNL-WGCKNRLICYTSVKWNKT (SEQ ID NO:7).

Variant polypeptides of this sequence are for example the polypeptides represented in FIG. 4 for the HIV-$1_{(MVP5180)}$ and HIV-$1_{(ant70)}$ isolates. These polypeptides may also be derived from the preceding ones by insertion and/or deletion and/or substitution, for example conservative substitution by amino acid residues.

The present invention relates to a peptide obtained from the HIV-1-O DUR virus deposited on Feb. 23, 1995 at the COLLECTION NATIONALE DES CULTURES DE MICRO-ORGANISMES (CNCM), Institut Pasteur, 28 rue du Docteur Roux, 75724 Paris Cedex 15, France, under the reference I-1542, or a peptide whose sequence is distinguished from that of the above by substitution, deletion or addition of amino acids, this separate peptide nevertheless retaining the antigenic characteristics of the above one.

Other peptides falling within the scope of the invention are defined below.

Thus, a preferred peptide of the invention is a peptide containing at least 4 consecutive amino acids contained in the GAG sequence represented in FIGS. 8A–C or in an immunologically similar GAG sequence obtained from a variant of the HIV-1-O DUR virus, said immunologically similar sequence being recognized by antibodies which also specifically recognize at least one of the sequences AHPQQA (SEQ ID NO:8), LWTTRAGNP (SEQ ID NO:9) contained in the GAG sequence of FIG. 8.

Preferably, this peptide consists of a peptide whose amino acid sequence is contained either in one of the following sequences:

SPRTLNAWVKAVEEKAFNPEIIPMFMALSEGA (1) (SEQ ID NO:10)

MLNAIGGHQGALQVLKEVIN (2) (SEQ ID NO:11)

GPLPPGQIREPTGSDIAGTTSTQQEQI (3) (SEQ ID NO:12)

IPVGDIYRKWIVLGLNKMVKMYSPVSILDI (4) (SEQ ID NO:13)

QGPKEPFRDYVDRFYKTKLAE (5) (SEQ ID NO:14)

AHPQQA (5a) (SEQ ID NO:8)

LWTTRAGNP (5b) (SEQ ID NO:9)

or in a corresponding immunologically similar sequence, this peptide containing at least 4 consecutive amino acids of one of said sequences.

Preferably also, this peptide consists of a peptide whose amino acid sequence is contained either in one of the following sequences:

SPRTLNAWVK (6) (SEQ ID NO:15)

GSDIAGTTST (7) (SEQ ID NO:16)

QGPKEPFRDYVDRF (8) (SEQ ID NO:17)

or in a corresponding immunologically similar sequence, this peptide containing at least four consecutive amino acids of one of said sequences.

Peptides which are particularly preferred in the present invention are the peptides containing:

the amino acid sequence NPEI (9) (SEQ ID NO:18) or the amino acid sequence AVEEKAFNPEIIPMFM (10) (SEQ ID NO:19), and more particularly peptides whose amino acid sequence is contained, either in one of the following sequences:

IGGHQGALQ (23) (SEQ ID NO:20)

REPTGSDI (24) (SEQ ID NO:21)

or in a corresponding immunologically similar sequence, this peptide containing at least 4 consecutive amino acids of one of said sequences, as well as the peptide whose amino acid sequence is contained, in the following amino acid sequence:

INDEAADWD (25) (SEQ ID NO:22)

or in a corresponding immunologically similar sequence, this peptide containing at least 4 consecutive amino acids of said sequence.

The present invention relates to the nucleic acid sequences coding for peptides (23), (24) and (25) as well as the nucleic acid sequences coding for the immunologically similar sequences, as well as compositions comprising at least one of these nucleic acids.

The invention also relates to the use of at least one of these nucleic acids for detection and discrimination between HIV-1 group M and HIV-1 group O strains.

A peptide derived from the HIV-1-O DUR virus defined above also falls within the scope of the present invention, said peptide containing at least 4 consecutive amino acids of the V3 loop of gp120 represented in FIG. 9A or of the corresponding immunologically similar sequence, obtained from a variant of the HIV-1-O DUR virus, said immunologically similar sequence being recognized by antibodies which also specifically recognize at least one of the sequences:

KEIKI (12) (SEQ ID NO:23),

EREGKGAN (13) (SEQ ID NO:24),

CVRPGNNSVKEIKI (14) (SEQ ID NO:25),

QIEREGKGANSR (15) (SEQ ID NO:26).

This peptide preferably contains:

a) either the sequence CVRPGNNSVKEIKIGPMAW-YSMQIEREGKGANSRTAFC (11) (SEQ ID NO:27) or a part of this sequence which contains at least 4 amino acids b) or an amino acid sequence which is separate from the sequence of a) in which one or more amino acids are replaced with one or more amino acids, with the proviso that the peptide retains its reactivity with an antiserum against the abovementioned peptide, c) or an amino acid sequence which is separate from a) or b), in which one or more amino acids have been deleted or added, with the proviso that the peptide retains its reactivity with an antiserum against the peptide of a), d) or a corresponding immunologically similar sequence or part of sequence.

Preferably also, this peptide contains either the sequence KEIKI (12) (SEQ ID NO:23), or the sequence EREGKGAN (13) (SEQ ID NO:24), or the sequence GPMAWYSM (16) (SEQ ID NO:28).

In a particularly preferred manner, a peptide as defined above contains the amino acid sequence CVRPGNNS-VKEIKI (14) (SEQ ID NO:25) or the sequence QIEREGK-GANSR (15) (SEQ ID NO:26).

A peptide derived from the HIV-1-O DUR virus as defined above also falls within the scope of the invention, said peptide containing at least 4 consecutive amino acids, whose entire sequence is contained in the sequence of the immunodominant region of gp41 represented in FIG. 9B or in a corresponding immunologically similar sequence, obtained from a variant of the HIV-1-O DUR virus, said immunologically similar sequence being recognized by antibodies which also specifically recognize at least one of the following sequences:

RLLALETLMQNQQL (17) (SEQ ID NO:29),
LNLWGCRGKAICYTSVQWNETWG (18) (SEQ ID NO:30),
CRGKAI (19) (SEQ ID NO:31),
SVQWN (20) (SEQ ID NO:32),
RLLALETLMQNQQLLNLWGCRGKAICYTS (21) (SEQ ID NO:33),
QNQQLLNLWGCRGKAICYTSVQWN (22) (SEQ ID NO:34).

This peptide is preferably a peptide containing the sequence RLLALETLMQNQQL (17) (SEQ ID NO:29), or LNLWGCRGKAICYTSVQWNETWG (18) (SEQ ID NO:30) or part of this peptide (18) (SEQ ID NO:30) containing:

a) either. the sequence CRGKAI (19) (SEQ ID NO:31) or the sequence SVQWN (20) (SEQ ID NO:32) in which Q is, where appropriate, replaced by a different amino acid, which is nevertheless also different from K, or the two sequences at the same time, b) or an amino acid sequence which is separate from the sequence of a) in which one or more amino acids are replaced with two amino acids, with the proviso that the peptide retains its reactivity with an antiserum against the peptide of a), c) or an amino acid sequence which is separate from a) or b), in which one or more amino acids have been deleted or added, with the proviso that the peptide retains its reactivity with an antiserum against the peptide of a), d) or in a corresponding immunologically similar sequence or part of sequence.

Preferably also, this peptide possesses one or the other of the following characteristics:

its N-terminal sequence which contains at least 8 amino acids is not immunologically recognized by antibodies formed against the sequence RILAVERY (SEQ ID NO:35) contained in the immunodominant region of gp41 of the HIV-1-LAI strain.

it is not recognized by antibodies formed against the peptide SGKLIC (SEQ ID NO:36) of the HIV-1-LAI strain.

it contains either of the following two sequences:
RLLALETLMQNQQLLNLWGCRGKAICYTS (21) (SEQ ID NO:33)
QNQQLLNLWGCRGKAICYTSVQWN (22) (SEQ ID NO:34)

Synthesis of VAU Peptides

A VAU peptide was prepared by the conventional solid phase peptide synthesis technique using the "continuous flow" Fmoc method. The peptide was prepared using a Milligen 9050 PEP synthesizer and using the "Millipore" PEG PAL resin, substituted with the first C-terminal amino acid residue. The side chains of the amino acids are protected by the following groups: Pmc for arginine; Trt for asparagine, glutamine and cysteine; Boc for lysine; tBu ester for glutamic acid; tBu ether for serine, threonine and tyrosine. The temporary Fmoc groups are removed with a 20% piperidine solution in DMF. The reactions for coupling each amino acid are performed with 6 equivalents of DIPCDI and HOBT. Some residues require a double coupling especially arginines 1 and 23, cysteines 19 and 26, asparagine 11, glutamines 10, 12 and 13, alanine 4, isoleucine 9 and leucines 2, 3, 14 and 15.

After coupling, the resin is dried under vacuum. The peptide is cleaved from the support by the K reagent for 4 hours at room temperature. The crude peptide is precipitated and washed with ethyl ether. The product is purified by high-pressure liquid chromatography (HPLC) in a WATERS LC PREP 4000 instrument with WATERS Delta Pak C18 40×100 mm cartridges, flow rate 30 ml/min, acetonitrile/ 0.1% TFA gradient. The fractions containing the peptide are combined, concentrated in a rotary evaporator and then lyophilized.

Cyclization

The peptide (0.025 mM) is dissolved in a 10 mM ammonium acetate solution. The pH is adjusted to 8.5 with 1M ammonium hydroxide solution. The pH is readjusted after 3 or 4 hours. The cyclization is monitored by HPLC at 214 nm and 280 nm, WATERS Delta Pak C18 5$\mu$p column, acetonitrile/0.1% TFA gradient. The cyclization is complete after 15 hours. The pH is brought to 6 using 97–100% acetic acid, the solution is lyophilized and then purified under the same conditions as for the crude peptide.

The peptide is checked by HPLC and by mass spectrometry according to the electrospray technique (FISON VG Trio 2000 spectrophotometer). (FIGS. 18A–B and FIGS. 19A–B)

Fmoc: 9-Fluoroenylmethyloxycarbonyl
Pmc: 8-Methylpentane-6-sulfonylchroman
Trt: Trityl
Boc: Tertbutyloxycarbonyl
tBU: tert butyl
DMF: Dimethylformamide
DIPCDI: Diisopropylcarbodiimide
HOBT: 1-Hydroxybenzotriazole
TFA: Trifluoroacetic acid
Reagent K: Phenol/water/thioanisole/ethanedithiol/TFA; 2.5 ml/2.5 ml/2.5 ml/1.5 ml/41 ml Comparison of the amino acid sequence of the HIV-1$_{(VAU)}$ envelope with the corresponding sequence of other HIV viruses.

Western-blot analysis of a series of serum samples obtained from a patient infected with HIV-1$_{(VAU)}$ is presented in FIG. 2. Nitrocellulose strips, carrying proteins separated by electrophoresis and obtained from purified HIV particles (LAV BLOT, SANOFI DIAGNOSTICS PASTEUR), were incubated with serum samples and their reactivity was evaluated according to the procedures recommended by the manufacturer. The results obtained are the following: strip 1: proteins specific for HIV-2, which have been reacted with a serum sample obtained in February 1992 from the HIV-1$_{(VAU)}$ patient. Strips 2–7: HIV-1 positive sera; sera from the HIV-1$_{(VAU)}$ patient: 2: obtained in November 1990; 3: in December 1990; 4: in February 1991; 5: in February 1992; 6: negative control; 7: positive control (serum from an individual infected with HIV-1). The names and the size of the proteins (in kD) are indicated in the margin.

FIG. 3 shows an alignment of the amino acid sequence of the HIV-1$_{(VAU)}$ envelope with the corresponding sequence of the HIV-1-LAI reference isolate (Wain-Hobson, et al. 1985). The signal peptides, the V3 loop and the gp41 immunodominant epitope are highlighted by shaded rectangles. The site of cleavage between the external envelope glycoprotein gp120 and the transmembrane gp41 is indicated by arrows.

The vertical lines between the amino acid letters indicate complete identity, colons (:) indicate high homology, and dots (.) indicate limited homology between individual amino acids. The alignment was performed using the GAP program of the Wisconsin GCG package.

The original version (1.0) of the GAP and BESTFIT programs was written by Paul Haeberli from a detailed study of the publications of Needleman and Vunsch (J. Mol. biol. 48, 443–453 (1970) and of Smith and Waterman (Adv. Appl. Math. 2; 482–489 (1981). The limited alignments were developed by Paul Haeberli and added to the package to constitute the 3.0 version. They were then fused into a single program by Philip Marquess to constitute the 4.0 version. The gap absence penalties in the alignment of the proteins were modified as suggested by Rechid, Vingron and Argos (CABIOS 5; 107–113 (1989)).

The alignment of FIG. 3 shows numerous regions of high divergence, with a few domains retained here and there. These retained regions correspond roughly to the domains also retained in the conventional HIV-1 isolates (Alizon et al. 1986, Benn et al. 1985). Among the divergent domains, the V3 loop, also called principal determinant of neutralization (Javaherian et al. 1990, Javaherian et al. 1989, Matsushita et al. 1988) is clearly one of the most divergent, although the two cysteines defining the loop are retained. The sequence of the cap of the loop, GPGRAF (SEQ ID NO:37) for HIV-1-LAI is GPMAWY (SEQ ID NO: 38) in HIV-1$_{(VAU)}$. This unit of the cap is identical to that of the Cameroonian group O isolate HIV$_{(ANT70)}$ (Van den Heasevelde et al. 1994), but is different from that of the other group O isolate, HIV$_{MVP5180}$ (Gürtler et al. 1994), for which the motif is GPMRWR (SEQ ID NO: 39).

In the entire envelope, 29 potential N-glycosylation sites were identified in total, of which 13 are retained compared with other HIV-1 envelope proteins. 19 retained cysteines were also found in total, which indicates that the overall folding architecture of the protein is retained, but 5 nonretained cysteines were found.

FIG. 4 shows the multiple alignment of the immunodominant peptides in the extracellular segment of the transmembrane envelope glycoprotein of various HIV-1 isolates. All the sequences are compared to the HIV-1-LAI reference sequence. Hyphens indicate identity with HIV-1-LAI. The alignment was made with the aid of the PILEUP program of the Wisconsin GCG package.

In the PILEVP program, the assembling strategy represented by the dendrogram is called UPGMA, which means "unweighted pair-group method using arithmetic averages" (Smith, P. H. A. Sokal, R. R. (1973) in Numerical Taxonomy (pp. 230–234), W.H. Freeman and Company, San Francisco, Calif., USA). Each pair alignment in PILEVP uses the Needleman and Wunsch method (Journal of Molecular Biology 48; 443–453 (1970)).

As shown in FIG. 4, the amino acid sequence of the immunodominant epitope of the external portion of the TM protein (Gnann et al., 1987) is substantially different from that of other HIV-1 and HIV-2 isolates. However, it retained most of the amino acids which were found to be conserved between the HIV-1 and HIV-2 viruses.

It was found that some specific amino acids were conserved only between group O viruses: such is the case for lysine in position 21 in a peptide of 26 amino acids, for threonine in position 7 and asparagine in position 11. These differences could explain the absence of detection of conventional HIV-1 envelope antigens by one of the sera from the HIV-1$_{(VAU)}$ patient and also probably by that of the patients infected by other group O viruses. Overall, the comparison between the HIV-1-LAI and HIV-1$_{(VAU)}$ envelope sequences showed a 50% identity. The HIV-1$_{(VAU)}$ envelope sequence was also compared to that of other HIV representatives including the two members of HIV-1 group O described and sequenced: HIV-1$_{ANT70}$ and HIV-1$_{MVP180}$ and SIV representatives. The results of this analysis, which are presented in Table 1, establish that HIV-1$_{(VAU)}$ belongs to group O. The HIV-1$_{(VAU)}$ envelope is 70% identical to the HIV-1$_{ANT70}$ envelope and 71% identical to HIV-1M$_{VP5180}$. Among the most common HIV-1 subtypes, the identity at the level of the envelope is comparable, ranging from 74% to 80%.

| | | | | | | | | | |
|---|---|---|---|---|---|---|---|---|---|
| HIV-1$_{EU}$ | 77 | | | | | | | | |
| HIV-1$_{MAL}$ | 76 | 80 | | | | | | | |
| HIV-1$_{U455}$ | 75 | 74 | 76 | | | | | | |
| SIV$_{CPZGAB}$ | 61 | 62 | 63 | 63 | | | | | |
| HIV-2$_{ROD}$ | 38 | 39 | 39 | 40 | 39 | | | | |
| SIV$_{MAC251}$ | 37 | 37 | 38 | 38 | 38 | 74 | | | |
| SIV$_{AGMTYO}$ | 37 | 36 | 37 | 38 | 40 | 46 | 47 | | |
| HIV$_{ANT\,70}$ | 51 | 52 | 52 | 52 | 53 | 33 | 32 | 33 | |
| HIV$_{MVP5180}$ | 51 | 52 | 54 | 51 | 52 | 36 | 33 | 34 | 70 |
| HIV$_{VAU}$ | 50 | 51 | 52 | 51 | 54 | 35 | 34 | 35 | 70 | 71 |
| | HIV-1$_{LAI}$ | HIV-1$_{EU}$ | HIV-1$_{MAL}$ | HIV-1$_{U455}$ | SIV$_{CPZGAB}$ | HIV-2$_{ROD}$ | SIV$_{MAX251}$ | SIV$_{AGMTYO}$ | HIV$_{ANT\,70}$ | HIV$_{MVP5180}$ |

Figure 5A:
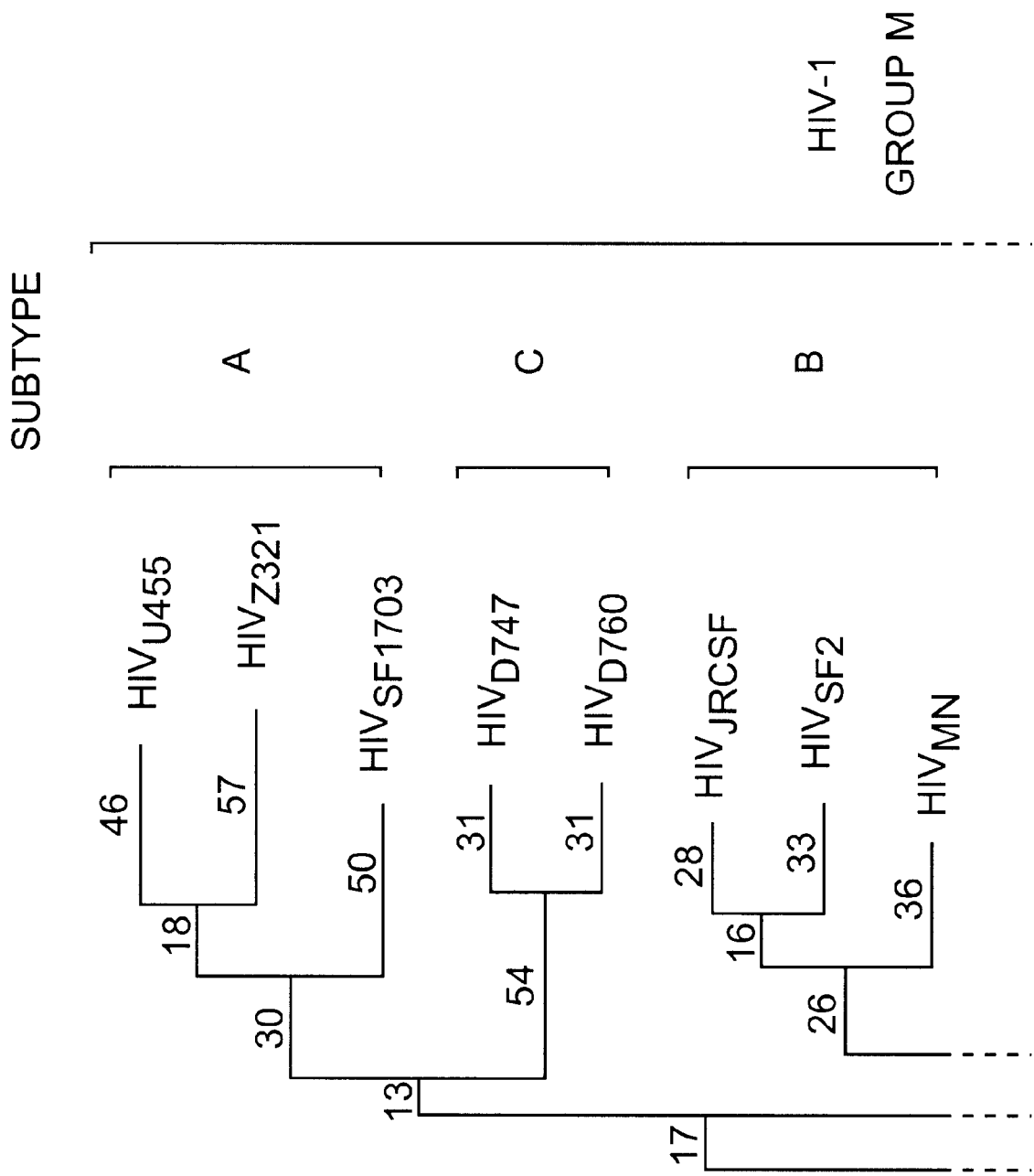
FIGS. 5A–B contain branches of a phylogenetic tree.
Figure 5B:
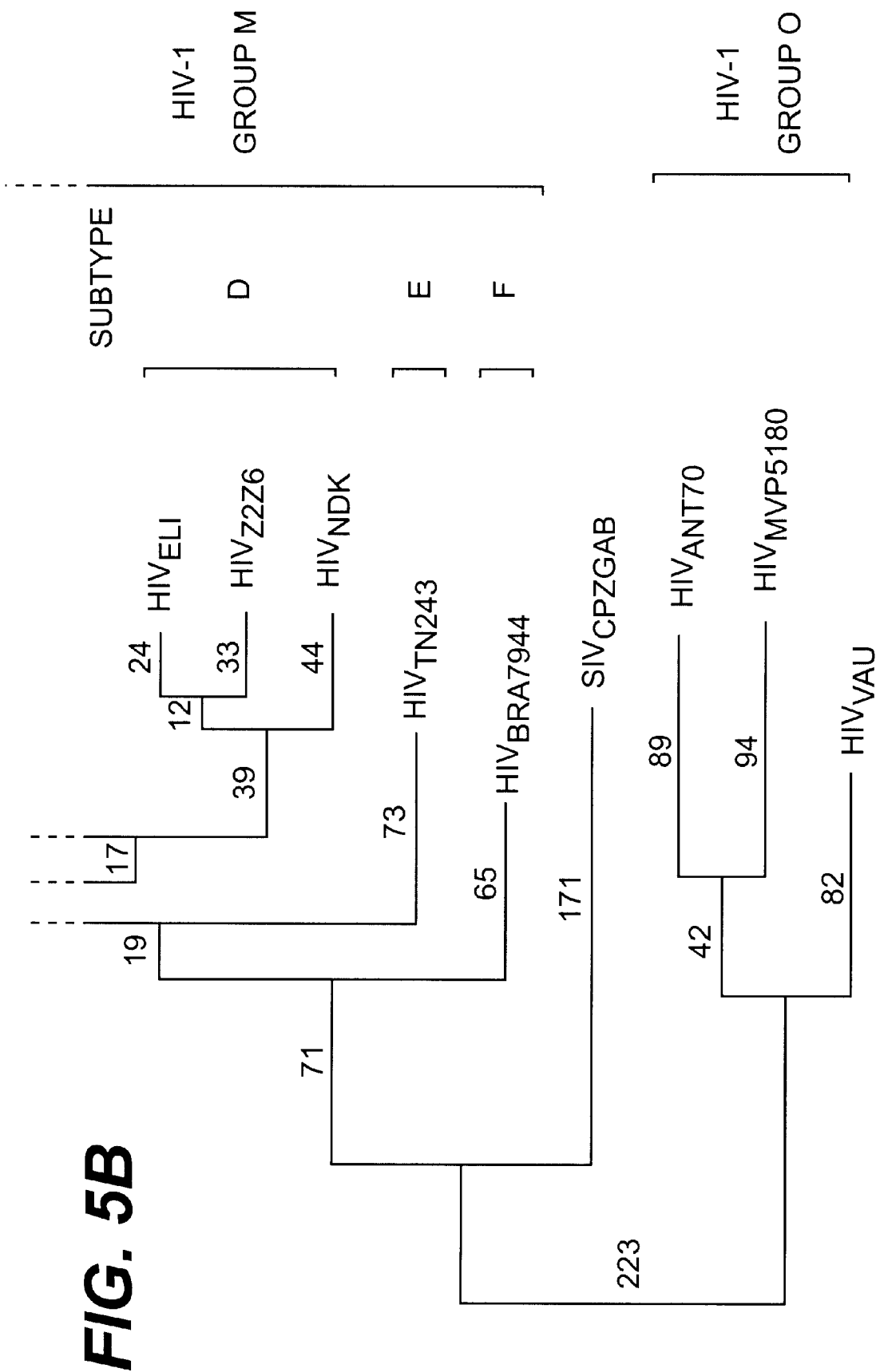

The relationship between HIV-1$_{(VAU)}$, other members of the phylogeny of HIV-1 viruses and the two viruses of group O recently described was analyzed by constructing a phylogenetic tree of unweighted parsimony using the nucleotide sequence of the env transmembrane region. The result of this analysis is represented in FIG. 5 in which the numbers indicate the number of nucleotide changes. FIG. 5 shows that HIV-1$_{(VAU)}$ is roughly equidistant from the other two group O viruses and that, overall, these three viruses appear to be approximately equidistant from each other. Indeed, the number of nucleotide changes between HIV-1$_{MVP180}$ and HIV-1$_{(VAU)}$ is 218 in the segment of the genome analyzed, whereas the distance is 183 between HIV-1$_{MVP5180}$ and HIV-1$_{ANT70}$, and 213 between HIV-1$_{ANT70}$ and HIV-1$_{(VAU)}$. This divergence profile is very similar to that which exists in all the other HIV-1 subtypes, where the number of single nucleotide changes which exist between two different subtypes ranges from 157 (subtype E to subtype F) to 219 (subtype A to subtype D).

Table 1 shows the comparison of the envelope sequences of different viruses related to HIV-1. The numbers indicate the percentage of amino acid identity between the envelope sequences, as calculated using the GAP program of the Wisconsin GCG package.: in the case of HIV$_{ANT70}$, only the external envelope protein was used in the comparison.

Compositions Comprising HIV-1$_{(VAU)}$ Antigens

Generally, the invention relates to any composition which can be used for the in vitro detection of the presence, in a biological fluid, especially from individuals who have been brought into contact with HIV-1$_{(VAU)}$, or with antibodies against at least one of the HIV-1$_{(VAU)}$ antigens. This composition can be applied to the selective diagnosis of infection by an HIV-1 group O by using diagnostic techniques such as those described in Patent Applications EP 84401,834 and EP 87400,151,4. Within the context of the present invention, any constituent comprising antigenic determinants capable of being recognized by antibodies produced against HIV-1$_{(VAU)}$ is used, for example recombinant antigens or peptides or chemically synthesized peptides defined from the sequence of the HIV-1$_{(VAU)}$ envelope. In this regard, the invention relates more particularly to compositions containing at least one of the HIV-1$_{(VAU)}$ virus envelope proteins. There may be mentioned, by way of examples of compositions, those which contain proteins, glycoproteins or peptides from the envelope protein corresponding to the entire 590–620 region of the HIV-1$_{(VAU)}$ gp41 protein or to the parts of this region which are specific for HIV-1$_{(VAU)}$ such as the peptides -TFIQN- (SEQ ID NO:40) or -WGCKNR- (SEQ ID NO:41).

The invention also relates to compositions combining recombinant or synthetic HIV-1$_{(VAU)}$ proteins and/or glycoproteins and/or peptides with proteins and/or glycoproteins and/or peptides from HIV-1 and/or HIV-2 and/or from another HIV-1 group O which are obtained by extraction or in lysates or by recombination or by chemical synthesis and/or peptides which are derived from these proteins or glycoproteins and which are capable of being recognized by antibodies induced by the HIV-1 and/or HIV-2 and/or HIV-1 group O virus.

The diagnostic compositions containing antigenic determinants capable of being recognized by antibodies directed against HIV-1$_{(VAU)}$, in particular the peptide compositions, may be included in or combined with compositions or kits already available for detecting infection by HIV-1 and/or HIV-2 retroviruses, so as to extend the detection range of the kits to the detection of HIV-1 group O retroviruses.

By way of nonlimiting examples:

either core proteins, particularly the gag, pol, HIV-1 and HIV-2 proteins or peptides thereof, and HIV-1$_{(VAU)}$ envelope proteins or peptides, or HIV-1 envelope glycoproteins, HIV-2 envelope glycoproteins and HIV-1$_{(VAU)}$ envelope glycoproteins, or mixtures of HIV-1 proteins and/or glycoproteins, HIV-2 proteins and/or glycoproteins and HIV-1$_{(VAU)}$ envelope proteins and/or glycoproteins.

It is important to note that, although the antibodies from patients infected with HIV-1 group O viruses react strongly with gag and pol antigens from HIV-1 group M viruses, their reactivity is practically zero with group M virus envelope antigens. It is therefore important that the composition of the present invention comprise at least one protein or one peptide of the HIV-1$_{(VAU)}$ envelope so that this virus can be detected with certainty.

Such compositions, when used in diagnosis, consequently help the diagnosis of AIDS or of the symptoms associated with it, which extend over a broader spectrum of causative etiological agents. It goes without saying that the use of diagnostic compositions which contain only HIV-1$_{(VAU)}$ envelope proteins and/or glycoproteins is nonetheless useful for the more selective detection of the category of retrovirus which may be held responsible for the disease.

Methods and Kits for the Diagnosis of Infections Caused Especially by the HIV-1$_{(VAU)}$ Virus The present invention relates to a method for the in vitro diagnosis of infection caused by HIV viruses, etiological agents of AIDS and related syndromes, which comprises bringing a serum or another biological medium, obtained from a patient or subject being subjected to the diagnosis, into contact with a composition containing at least one protein, glycoprotein or peptide from HIV-1$_{(VAU)}$, and detecting a possible immunological reaction. Examples of such compositions were described above.

Preferred methods involve, for example, immunofluorescence or ELISA type immunoenzymic reactions. The detections may be effected by direct or indirect immunofluorescence measurements or direct or indirect immunoenzymic assays.

Such detections comprise for example:

depositing defined quantities of the extract or of the desired antigenic compositions in accordance with the present invention into the wells of a microplate;

introducing into each well a serum, diluted or undiluted, which is capable of containing the antibodies, the presence of which has to be detected in vitro;

incubating the microplate;

carefully washing the microplate with an appropriate buffer;

introducing into the wells of the microplate specific labeled antibodies to human immunoglobulin, the labeling being performed with an enzyme chosen from those which are capable of hydrolyzing a substrate such that the latter then undergoes modification of its absorption of radiation, at least in a defined wavelength band, and detecting, preferably in a comparative manner relative to a control, the extent of the hydrolysis of the substrate as a measure of the potential risks or of the actual presence of the infection.

The present invention also relates to kits or boxes for the diagnosis of HIV-1$_{(VAU)}$ virus infection, which comprise in particular:

an extract, a more purified fraction, or a synthetic antigen derived from the types of viruses indicated above, this extract fraction or antigen being labeled, for example, radioactively, enzymically, fluorescently or otherwise, antibodies to human immunoglobulins or a protein A (which is advantageously attached to a support which is insoluble in water) such as agarose beads for example) or microplate wells, and the like), optionally, a sample of biological fluid or cells obtained from a negative control subject;

buffers and, where appropriate, substrates for visualizing the label.

The subject of the invention is also immunogenic compositions which are capable of inducing the formation of antibodies recognizing antigens which can be obtained by chemical synthesis or by recombination.

Serology

The capacity of the serum antibodies from the patient infected with HIV-1$_{(VAU)}$ to react with HIV-1 antigenic preparations was evaluated using various commercially available kits: Sanofi Diagnostics Pasteur, (Genelavia Mixt) Abbott, Wellcome, and Behring. The reactivity of these antibodies with various HIV-1 proteins was examined using the Sanofi Diagnostics Pasteur Western-blot kit, following the procedures recommended by the manufacturer.

More precisely, the patient's serum was examined several times using HIV-1 specific ELISA kits. It was first tested and proved to be positive in 1990, being noted 7.33 (this figure corresponds to the ratio of the measured OD to the background OD) with the Sanofi Diagnostics Pasteur kit, 3.50 with the Abbott kit and 2.70 with the Wellcome kit. During the use of reagents specific both for HIV-1 and HIV-2, the serum was noted 1.42 with the Behring kit and 4.40 with the Wellcome kit.

The capacity of the patient's serum to react on different dates with different HIV-1 structural proteins was studied using the HIV-1 LAV BLOT immunoblot assay, a test marketed by Sanofi Diagnostics Pasteur. As shown in FIG. 5 with all the serum samples tested, only a very weak reactivity of the serum with the HIV-1 env proteins gp160 and gp120 was noted. However, the serum reacted strongly with the HIV-1 gag proteins p55 (gag precursor) and p24 (CA), and with the pol products p66 (RT) and p34 (IN). By HIV-2 immunoblotting, only a very weak reactivity was detected with the gag p26.

This illustrates that the detection of antibodies specific for group O with commercially available serum diagnostic kits should be carefully controlled. Although serum antibodies from patients infected with group O viruses show strong cross-reactions with the group M gag and pol antigens, they show few or no reactions with the group M envelope antigens. Consequently, it is possible to assume that a significant proportion of these patients might not be detected using some kits based on group M envelope antigenic reagents. Indeed, in a recent preliminary study of several sera from patients infected with group O, it was found that the capacity to detect antibodies specific for group O was very different depending on the detection kit used (Loussert-Ajaka, I., Ly, T. D., Chaix, M. L., Ingrand, D., Saragosti, S., Courroucé, A. M., Brun-Vézinet, F. and Simon, F. (1994). HIV-1/HIV-2 seronegativity in HIV-1 subtype O infected patients. Lancet. 343, 1393–1394.). This implies that a careful and extensive study of the reactivity of a large number of group O sera with all the diagnostic kits available on the market is necessary.

Compositions comprising polyclonal or monoclonal antibodies prepared from recombinant or synthetic antigens from the HIV-1$_{(VAU)}$ virus.

The invention relates to a serum capable of being produced in animals by inoculating them with HIV-1$_{(VAU)}$, particularly the antigenic epitopes of HIV-1$_{(VAU)}$ and more particularly the antigenic epitopes of the HIV-1$_{(VAU)}$ virus envelope protein. The invention relates more particularly to the polyclonal antibodies more specifically oriented against each of the antigens, especially proteins or glycoproteins of the virus. It also relates to monoclonal antibodies produced by various techniques, these monoclonal antibodies being respectively oriented more specifically against the various HIV-1$_{(VAU)}$ proteins, particularly the HIV-1$_{(VAU)}$ envelope proteins.

These polyclonal or monoclonal antibodies can be used in various applications. There may be mentioned essentially their use for neutralizing the corresponding proteins, or even for inhibiting the infectivity of the whole virus. They may also be used for example to detect viral antigens in biological preparations or to carry out procedures for purifying the corresponding proteins and/or glycoproteins, for example during their use in affinity chromatography columns.

By way of example, anti-envelope antibodies or anti-gag antibodies are reagents which can be used in diagnosis, in particular for the detection of HIV-1 group O particles by antigen capture ELISA.

The invention relates to antibodies directed against one or more HIV-1$_{(VAU)}$ viral antigens produced from amino acid sequences of HIV-1$_{(VAU)}$. Techniques for obtaining antibodies from antigenic epitopes similar to the antigenic epitopes of the HIV-1$_{(VAU)}$ virus of the present invention have been described previously.

The technique for the preparation of antibodies which is described in the publication by Ulmer et al., 1993, may be used by persons skilled in the art to prepare the antibodies of the present invention, the modifications which make it possible to adapt this technique to the antigens of the present invention forming part of the knowledge of persons skilled in the art.

Study of the Immunoreactivity of the Vau Peptide

The immunoreactivity of the vau peptide was confirmed, after experimental ELISA plates had been prepared, according to a procedure established for a screening test for anti-HIV antibodies. This test is based on the detection of a solid phase prepared with the peptide which mimics the immunodominant epitope of the envelope glycoprotein of the HIV-1 group (or subgroup) O virus, VAU isolate. The implementation of the test was modeled on the procedure proposed by the Genelavia® Mixt kit, using the reagents in that kit.

The experimental data collated in the two tables of FIGS. 20A–C and 21A–C show that:

a) the four sera taken from patients contaminated with the HIV-1 group (or subgroup) O virus are very reactive with the vau peptide;

b) the ten sera supposedly taken from patients contaminated with the HIV-1 (group or subgroup) O virus, among the 19 sera sent out by the Pasteur Institute of Yacoundé, are also highly reactive with this same peptide;

c) the sera (4 samples) taken from individuals contaminated with the HIV-1 subtype B virus (in the acute phase) are not reactive with the vau peptide;

d) the sera taken from asymptomatic blood donors (48 samples tested) are not reactive with the vau peptide; These experimental data, although limited (in view of the paupicity of HIV-1 group (or subgroup O) antibody-positive samples), bear witness to the sensitivity and specificity of the peptide selected.

From the above text, it follows that the invention also relates to the detection of the HIV-1$_{(VAU)}$ virus or of a variant by virtue of the use of the antibodies described above in a method involving various stages, these stages being specifically intended to reveal the characteristic properties of the HIV-1$_{(VAU)}$ virus.

The invention also relates to the detection of the HIV-1$_{(VAU)}$ virus by molecular hybridization.

Generally, this method for detecting the HIV-1$_{(VAU)}$ virus or a variant in serum samples or samples of other biological fluids or tissues, obtained from patients liable to be carriers of the HIV-1$_{(VAU)}$ virus, comprises the following stages:

the manufacture of at least one optionally labeled probe;

at least one hybridization stage performed under conditions permitting hybridization by bringing the nucleic acid of the suspect patient's sample into contact with said labeled probe and optionally immobilizing the complex formed on an appropriate solid support, where appropriate, washing said solid support with a suitable washing solution, the detection of said complex and therefore of the presence or otherwise of the HIV-1$_{(VAU)}$ virus by an appropriate detection method known to those skilled in the art.

In another preferred embodiment of the method according to the invention, the abovementioned hybridization is performed under nonstringent conditions and the membrane is washed under conditions adapted to those for the hybridization.

By using serology or a gene amplification technique such as specific Polymerase Chain Reaction (PCR), the extent of the HIV-1 group O epidemic was precisely evaluated. It was found that 5 to 10% of patients infected with HIV-1 in Cameroon are in fact infected with group O viruses. However, apart from the virus isolate described here, the propagation of the group O virus outside West Central Africa has not been documented. The patient from whom HIV-1 $_{(VAU)}$ was isolated has always lived in France and has never traveled to Africa. Up until now, we have no precise proof relating to the origin of her infection, but this case indicates that a degree of propagation of the group O viruses in Europe has already occurred.

The invention also relates to a process of detection and discrimination, in a biological sample, between antibodies characteristic of an HIV-1 group (or subgroup) O retrovirus and antibodies characteristic of a retrovirus of the HIV-1-M type, characterized by placing this biological sample in contact with a peptide which does not react with the antibodies characteristic of a retrovirus of the HIV-1-M type, in particular one chosen from the peptides (1), (2), (3), (4), (5a), (5b), (9) and (10) described above.

Also, the invention relates to a process of detection and discrimination, in a biological sample, between antibodies characteristic of an HIV-1 group (or subgroup) O retrovirus and antibodies characteristic of a retrovirus -of the HIV-1-M type, characterized by placing this biological sample in contact with the peptide derived from one of the HIV-1 M viruses taken into consideration in FIGS. 8 and 9 and homologous to a peptide chosen from the peptides (1), (2), (3), (4), (5a), (5b), (9) and (10), the sequence of this homologous peptide resulting from vertical alignments of its own successive amino acids which are themselves contained in the pertinent peptide sequence relative to the corresponding HIV-1-M virus and represented in FIG. 8 or 9 with the successive amino acids of the sequence of the peptide chosen, as also follows from FIG. 8 or 9.

According to the present invention, the process of detection and discrimination between infection by an HIV-1 group (or subgroup) O retrovirus and an HIV-1 subgroup M retrovirus is characterized by placing serum, obtained from individuals subjected to an AIDS diagnostic test, in contact, in particular, with the peptide RILAVERY (SEQ ID NO:35).

In addition, the process for detection of infection due either to an HIV-1 subgroup O or HIV-1 subgroup M retrovirus is characterized by the use of mixtures of two categories of peptides, those of the first category corresponding to the peptides (1), (2), (3), (4), (5a), (5b), (9) and (10).

Moreover, the process for discrimination between an infection due to an HIV-1-O DUR retrovirus and an infection due to another type of HIV-1-O retrovirus, is characterized by placing the biological test sample in contact with any of the peptides (11) to (15) or of the peptides (17) to (20).

Alternatively, it is a process for discrimination between an infection by an HIV-1 group (or subgroup) O retrovirus and an HIV-1 subgroup M retrovirus, using a serine protease whose cleaving action is carried out on an SR dipeptide, and comprising the detection of a cleavage or of a non-cleavage of the V3 loop of gp120 of the retrovirus, depending on whether this retrovirus is an HIV-1 group (or subgroup) O retrovirus or an HIV-1 subgroup M retrovirus.

The invention also relates to a composition for detection and discrimination, in a biological sample, between an HIV-1 subgroup M retrovirus and an HIV-1 group (or subgroup) O retrovirus, comprising a mixture of two categories of peptides, the first being in particular those identified (1), (2), (3), (4), (5a), (5b), (9) and (10).

Monoclonal antibodies specific for the sequences of each of the peptides (1) to (20) also fall within the scope of the present invention.

The invention also relates to a plasmid chosen from those which were deposited at the CNCM on Feb. 24, 1995 under the references I-1548, I-1549 and I-1550.

The invention is also directed towards nucleic acids containing a sequence which codes for each of the peptides (1) to (20) defined in the present invention.

Among the preferred nucleic acid sequences, the nucleotide sequences represented in FIG. 10, 11 or 12 will be chosen.

The invention also relates to vectors containing a nucleic acid as defined above.

The invention is also directed towards cells liable to contain any one of said nucleic acids or of said vectors.

The present invention also relates to a virus such as that deposited on Feb. 23, 1995 at the CNCM under the reference I-1542.

A virus also falling within the scope of the invention is a virus of the same group as the above, characterized in that consensus peptides of this virus are recognized by antibodies which specifically recognize a polypeptide or a peptide defined above.

The genomic RNA of this virus also falls within the scope of the invention.

Also falling within the scope of the invention is a box or kit for detection of antibodies in the serum or any other biological sample from a patient liable to be infected with a human retrovirus of the HIV type, characterized in that it comprises:

- at least one polypeptide or one peptide having, in particular, as its sequence one of the sequences (1) to (20) described above.
- means allowing the reaction for formation of the immunological complex between the polypeptide(s) or the peptide(s) and the antibodies which may be present in the biological sample to be tested, for example one or more incubation buffers, if needed,
- a negative control sample,
- means for visualizing the antigen/antibody complex formed.

Also according to the invention, this kit contains, in addition, at least one consensus peptide or polypeptide derived from another HIV strain or from a peptide or polypeptide comprising

- either an amino acid sequence which is separate from the sequence of this polypeptide or peptide, in which one or more amino acids are replaced with other amino acids, with the proviso that the peptide or polypeptide retains its reactivity with an antiserum against the consensus peptide or polypeptide,
- or an amino acid sequence in which one or more amino acids have been deleted or added, with the proviso that the peptide or polypeptide retains its reactivity with an antiserum against the consensus peptide or polypeptide.

Preferably, a kit according to the invention will contain, in addition, at least one peptide or polypeptide derived from another HIV strain, preferably the HIV-LAI strain.

The invention also relates to a polypeptide composition for the in vitro diagnosis of an infection due to a retrovirus according to the invention, or to one of its variants, this diagnosis being made on a biological sample liable to contain antibodies formed after said infection. This composition is characterized in that it comprises at least one of the peptides (1) to (20).

The biological sample may consist in particular of blood, plasma, serum or any other biological extract. The above compositions may be used for the detection of antibodies in one of the abovementioned biological samples.

The invention is therefore also directed toward a method for the in vitro diagnosis of an infection due specifically to a retrovirus of the HIV type, characterized by the steps of:

placing a biological sample, which is liable to contain antibodies produced after an infection by an HIV-1 group (or subgroup) O retrovirus, in contact with a peptide as defined above, or with a peptide composition as defined above, under suitable conditions which allow the formation of an immunological complex of the antigen/antibody type, detection of the possible presence of the complex.

The invention moreover relates to an immunogenic composition, characterized in that it comprises at least one peptide in combination with a pharmaceutical vehicle which is acceptable for making up vaccines.

The invention also relates to a process for the preparation of capsid proteins and gp41 and gp120 glycoproteins of a retroviral strain according to the invention, the process being characterized by the following steps:

lysis of the cells infected with an HIV-1 retrovirus according to the invention and separation of the supernatant and of the infected cells or lysis of the viral pellets prepared by centrifugation, deposition of the cell extract and/or of the viral extract on an immunoadsorbant containing purified antibodies, which are obtained from the serum of an individual infected by a retrovirus according to the invention and advantageously attached to a suitable support, said serum of the infected individual having the capacity to react strongly with envelope proteins of the virus according to the invention, incubation in the presence of a buffer and for a sufficiently long period to obtain the formation of an antigen/antibody immunological complex, washing of the immunoadsorbant with a buffer in order to remove the molecules not retained on the support, recovery of the desired antigenic proteins.

According to a first embodiment of this preparation process, the separation and the recovery of the capsid proteins and of the gp41 and gp120 glycoproteins of HIV-1 DUR are carried out by electrophoresis and by electroreduction of the proteins.

According to another embodiment of this preparation process, the proteins are recovered by:

elution of the proteins attached to the above immunoadsorbant, purification of the products thus eluted on a chromatography column containing, attached to the separation support, antibodies which recognize the capsid proteins and the gp41 and gp120 glycoproteins of HIV-1 group (or subgroup) O DUR.

Also falling within the scope of the invention is a process for the production of a peptide or polypeptide according to the invention, this peptide or polypeptide being obtained either by expression of a nucleic acid of the invention, or by chemical synthesis, by addition of amino acids until this peptide or this polypeptide is obtained.

The standard principles and processes of genetic engineering may be used here ("Molecular cloning", Sambrook, Fritsch, Maniatis, CSH 1989).

Also falling within the scope of the invention is a process for the production of a nucleic acid defined above, which may be produced either by isolation from a virus of the invention, or by chemical synthesis, or by using techniques of in vitro amplification of nucleic acids from specific primers.

Oligonucleotide primers also according to the invention have a sequence consisting of at least eight consecutive nucleotides of the following nucleotide sequences:

ATT CCA ATA CAC TAT TGT GCT CCA-3' (SEQ ID NO:42)

AAA GAA TTC TCC ATG ACT GTT AAA-3' (SEQ ID NO:43)

GGT ATA GTG CAA CAG CAG GAC AAC-3' (SEQ ID NO:44)

AGA GGC CCA TTC ATC TAA CTC-3' (SEQ ID NO:45)

These primers may be used in a gene amplification process, for example by PCR or an equivalent technique, of a nucleotide sequence coding for a peptide of the invention. Tests carried out with these primers gave conclusive results.

Also, the invention relates to a kit allowing amplification by PCR or an equivalent technique described above.

Also falling within the scope of the present invention is a process for detection of the presence, in a biological sample, of nucleic acid(s) characteristic of an HIV-1 group (or subgroup) O DUR retrovirus, including a retrovirus according to the invention. This process comprises a placing in contact of a cDNA formed from RNA(s) contained in this biological sample, under conditions allowing the hybridization of this cDNA with the retroviral genome, and the execution of a gene amplification on this viral sample.

The invention also relates to a viral lysate as obtained by lysis of cells infected with a virus according to the invention.

A protein extract from an HIV-1$_{(DUR)}$ (or HIV-1$_{(VAU)}$) strain containing in particular a peptide or a polypeptide as defined above also falls within the scope of the invention.

The invention relates to specific peptides obtained from the structure of HIV-1 group (or subgroup) O DUR or from variants of this retrovirus and which make it possible either to discriminate, depending on the case, globally between HIVs-1 belonging to the category O and HIVs-1 belonging to the category M, or, more specifically, between viruses belonging to the subgroup characteristic of the HIV-1 group (or subgroup) O DUR and other viruses of the subgroup O, or, on the other hand, to recognize most, if not all, of the retroviruses both of the group (or subgroup) O and of the subgroup M.

Also falling within the scope of the invention are the corresponding peptides obtained from corresponding structural proteins of other HIV-1 group (or subgroup) O or HIV-1 subgroup M viruses, in particular those derived from the GAG, gp120 and gp41 structural proteins whose parts are indicated in the diagrams, these homologous peptides ensuing from their being placed in alignment, as also results from the diagrams with the peptides obtained from the HIV-1 group (or subgroup) O DUR, more particularly identified in the present text.

Similarly, certain homologous peptides may be used in those tests which make it possible to carry out the abovementioned discriminations, it being understood in this case that they are then used in place of the corresponding peptides, derived from the GAG, gp120 and gp41 structural proteins.

Determination of Oligonucleotides Specific for the O Group

Using the VAU sequence and its correlation with the MVP5180 and ANT70 sequences, oligonucleotide primers were defined which endeavor to be specific for the subgroup O in its entirety for the V3 region and the gp41 region. These primers made it possible to amplify the DUR strain and consequently constituted one solution to the amplification problem encountered. The position and the sequence of these HIV subgroup O primers are represented in FIGS. 13B and A respectively. These primers make it possible to obtain an amplification band which is visible on staining with ethidium bromide, with a single step of 30 cycles of PCR. Partial sequences were obtained:

GAG: 513 base pairs (171 amino acids)=Seq ID NO:95 and SEQ ID NO:96, FIGS. 10A and B gp120 V3 loop: 525 base pairs (75 amino acids)=Seq ID NO:97 and SEQ ID NO:98, FIGS. 11A and B gp41 immunodominant region: 312 base pairs (104 amino acids)=Seq ID NO:99 and SEQ ID NO:100, FIGS. 12A and B Nucleotide (FIGS. 15A–C) and protein (FIGS. 16A–C) comparisons of the DUR sequences with the MVP5180, ANT and VAU sequences for the O subgroup, LAI for the HIV-1 consensus sequence, representative African HIV-1 MAL sequence, and CPZ for the CIV of the Gabonese chimpanzee, show that DUR is as remote from the other published HIV-1 group (or subgroup) O strains as the latter are from each other.

Figure 17:
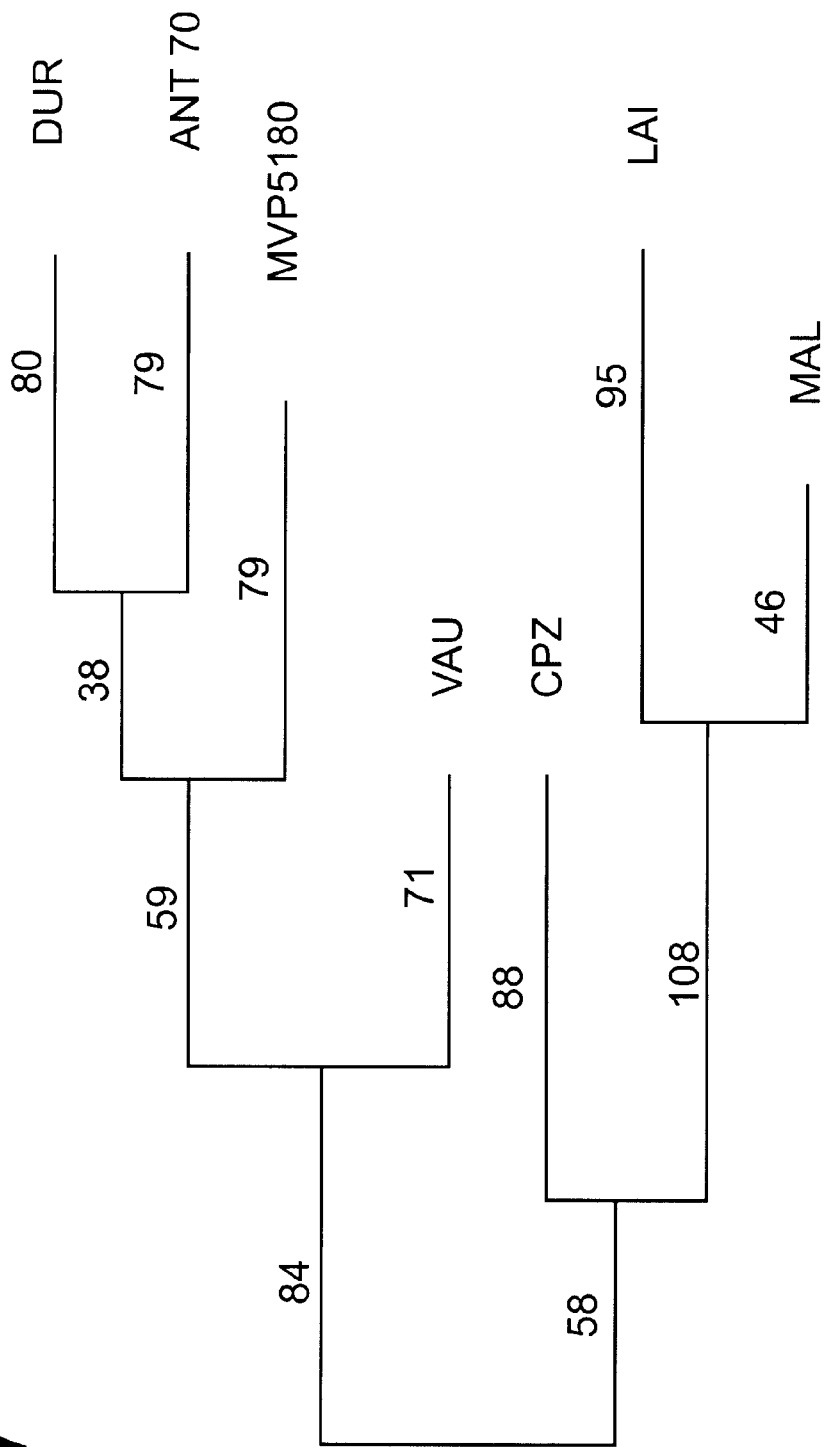
FIG. 17 is a phylogenetic tree.
Figure 18A:
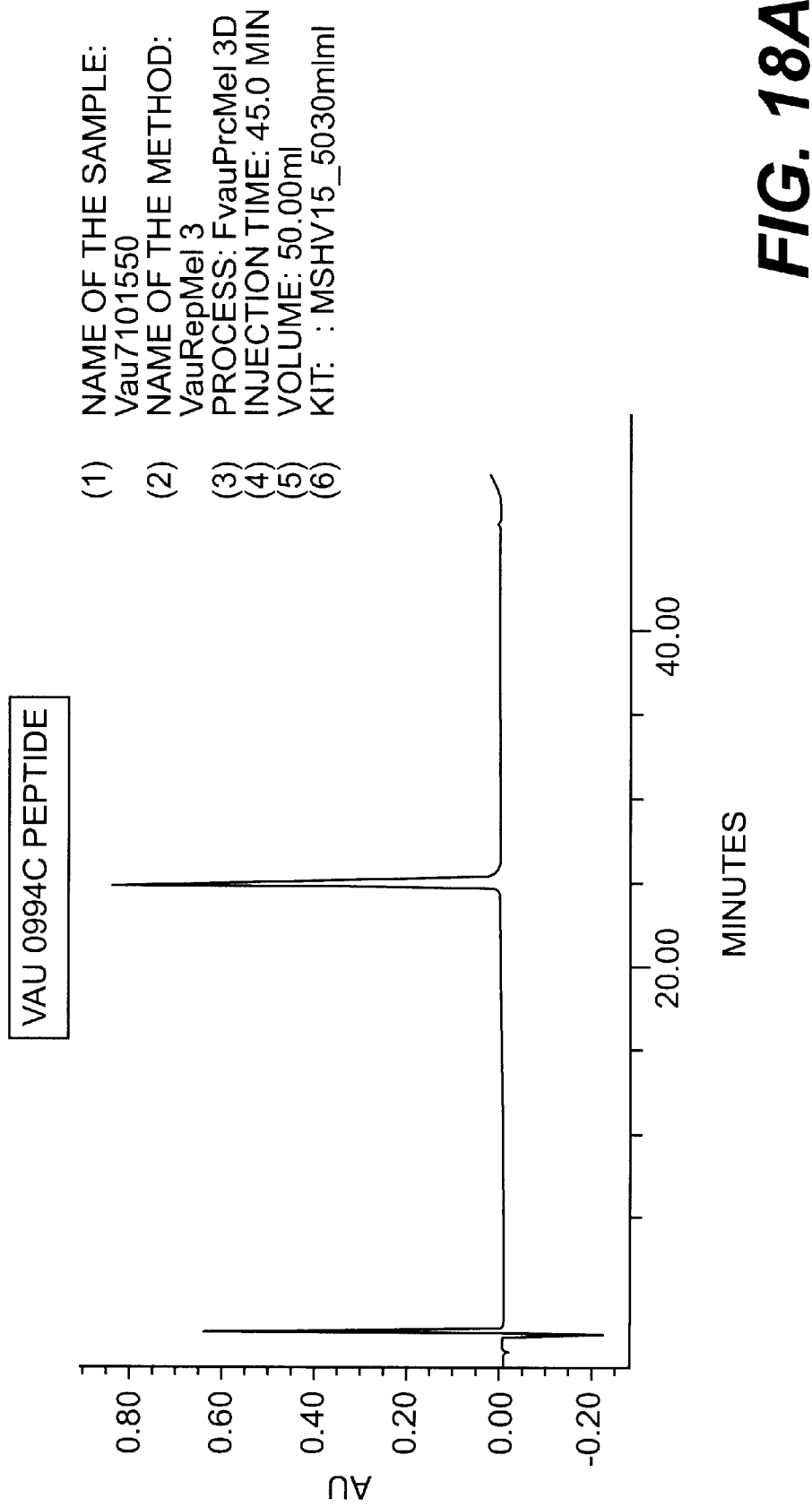
Figure 19A:
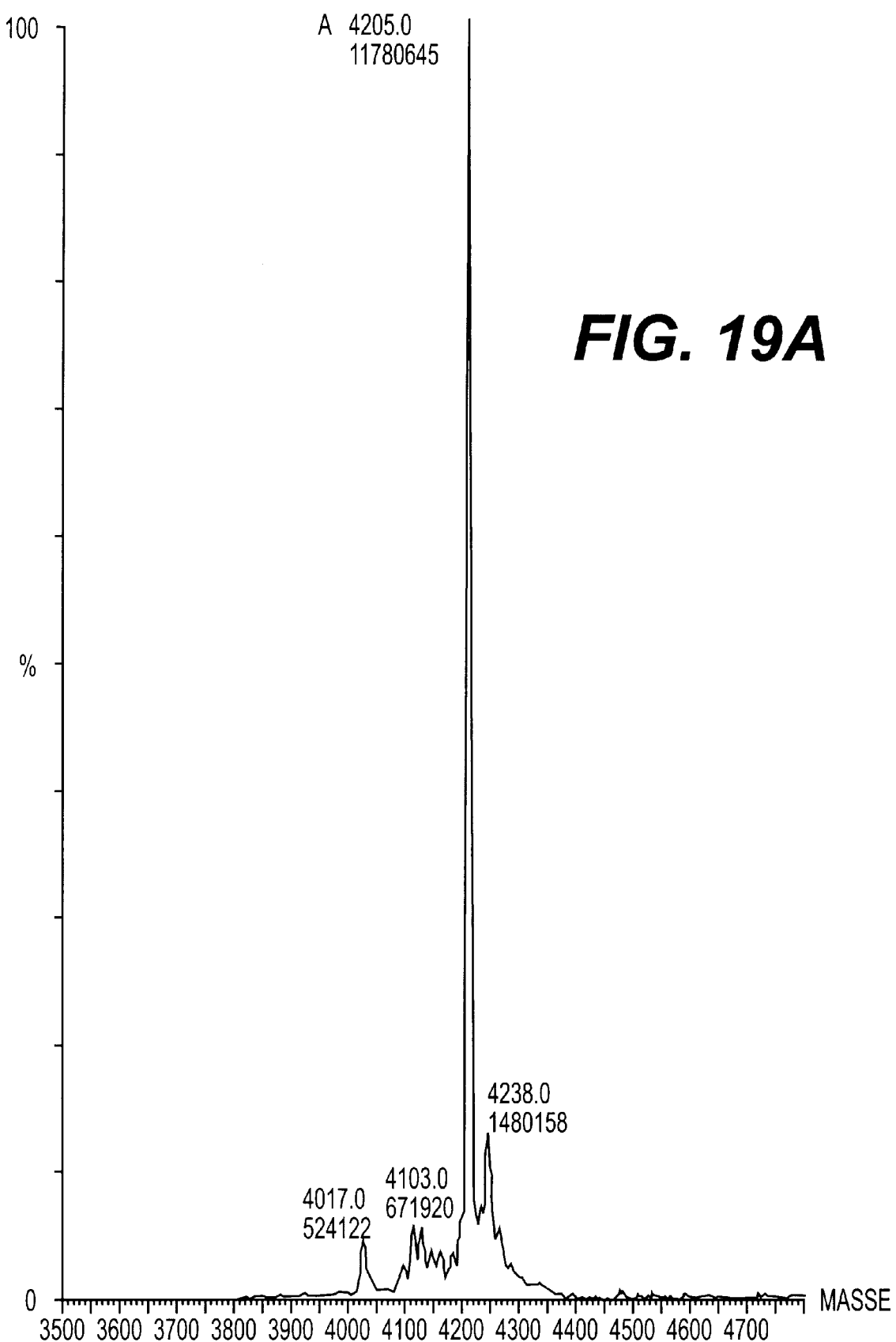

The differences are less in the GAG region and maximal in the region of the V3 loop of gp120, where the protein comparison reaches a difference of 40% (FIG. 16). The phylogenic trees confirm, on the one hand, that the DUR strain forms part of the O subgroup, and, on the other hand, the importance of the differences between the various O strains described, without, however, subtype branching emerging clearly (FIG. 17).

Comparison of the GAG Sequences:

On comparison of the GAG sequence obtained with the other two O strains published, ANT70 and MVP5180, as well as with the representative sequences of the M group (FIG. 8), it was possible to observe that an O consensus sequence exists in several regions, which is distinct from the M consensus sequence in the same regions. Two hypervariable regions, which are more variable for O than for M, and a few point differences for one or the other strain may also be found. Nevertheless, the regions SPRT . . . SEGA, MLNAI . . . KEVIN, GPLPP . . . QQEQI and VGD . . . SPV appear to discriminate between the O consensus sequence and the M consensus sequence.

The regions QQA and LWTTRAGNP are hypervariable regions. The HIV-1 group (or subgroup) O DUR strain is conspicuously different in three positions with respect to the M and O consensus sequence (L for I and twice for E) and takes a specific amino acid in three isolated hypervariable positions, V position L9; A position A77; L position 110.

In addition, it is possible to define in the GAG region segments common to the O group and to the M group, such as SPRTLNAWVK (SEQ ID NO:15), GSDIAGTTST (SEQ ID NO:16) and QGPKEPFRDYVDRF (SEQ ID NO:17).

Comparison of the Sequences of the V3 Loop

This comparative study revealed considerable differences of up to 56% for protein differences with the HIV-1 subgroup M consensus sequence, and 35 to 42% with the other HIV-1 group (or subgroup) O consensus sequences.

The alignments of peptide sequences in the regions of the V3 loop of gp120 and in the immunodominant region of gp41 is given in FIG. 9. The sequence of the interior of the V3 loop of the DUR strain differs substantially from that of the HIV-1 subgroup M consensus sequence. It shares the motif GPMAWYSM (SEQ ID NO:28) with the VAU and ANT70 strains but not with the MVP strain, which has two substitutions: R for A and R for Y.

The left and right parts of the rest of the V3 loop are markedly different from all the other HIVs known and do not leave it possible to imagine other cross-reactivities. Furthermore, the V3 loop of DUR is one amino acid longer than the other O sequences, which are themselves another one amino acid longer than the sequences of the HIV-1 M group.

Comparison of the Alignments Concerning the Immunodominant Region of gp41

The "mini loop" of the DUR strain, having the sequence CRGKAIC, proved to be very specific for this strain: it might constitute an epitope (see FIG. 9). In addition, this sequence might be likely to be involved in the modification of the conditions of unfolding of the gp41 glycoprotein, and consequently in the infectiousness of the strain.

A long sequence of 11 amino acids flanking this loop on the left is identical to the VAU sequence. A polymorphism of the DUR strain may be noted for an S or T position according to the clones analyzed.

Corresponding peptides obtained from other known retroviral strains are also represented in FIG. 9.

The DUR strain also makes it possible to define an HIV subgroup O consensus sequence of the gp41 region, several sufficiently long homologous regions of which might be used. These homologous regions are, inter alia: RL*ALET, QNQQ,LWGC and CYTV (*representing a variable amino acid).

Serological Correlations:

The anti-DUR antiserum does not react with the peptides of the V3 loop of the HIV-1-M consensus sequence, of HIV-1 MAL, of HIV-1 CPZ or of HIV-1 group (or subgroup) O MVP5180 but does, however, react with the peptide of the V3 loop of HIV-1-O ANT70 as seen in FIG. 14A. As regards the gp41 immunodominant region, this does not react with the "standard" HIV-1 subgroup M consensus sequence, but does, however, react, weakly but surprisingly, with the HIV-1 subgroup M right-extended consensus sequence as seen in FIG. 14B.

REFERENCES

Agut, H., Candotti, D., Rabanel, B., Huraux, J., Remy, G., Ingrand, D., Tabary, T., Chippaux, C., Chamaret, S., Guétard, D., Dauguet, C. and Montagnier, L. (1992). Isolation of atypical HIV-1-related retrovirus from AIDS patient. Lancet. 340, 681–682.

Alizon, M., Wain-Hobson, S., Montagnier, L. and Sonigo, P. (1986). Genetic variability of the AIDS virus: nucleotide sequence analysis of two isolates from African patients. Cell. 46, 63–74.

Barré-Sinoussi, F., Chermann, J. C., Rey, F., Nugeyre, M. T., Chamaret, S., Gruest, J., Dauguet, C., Axler-Blin, C., Brun-Vezinet, F., Rouzioux, C., Rozenbaum, W. and Montagnier, L. (1983). Isolation of a T-lymphotropic retrovirus from a patient at risk for acquired immune deficiency syndrome (AIDS). Science. 220, 868–871.

Benn, S., Rutledge, R., Folks, T. et al, e. (1985). Genomic heterogeneity from AIDS retroviral isolates from North America and Zaire. Science. 230, 949–951.

Clavel, F. and Charneau, P. (1994). Fusion from without directed by Human immunodeficiency virus particles. J. Virol. 68, 1179–1185.

Clavel, F., Guétard, D., Brun-Vézinet, F., Chamaret, S., Rey, M. A., Santos-Ferreira, M. O., Laurent, A. G., Dauguet, C., Katlama, C., Rouzioux, C., Klatzmann, D., Champalimaud, J. L. and Montagnier, L. (1986). Isolation of a new human retrovirus from West African patients with AIDS. *Science*. 233, 343–346.

De Cock, K. M., Adjorlolo, G., Epkini, E., Sibailly, T., Kouadio, J., Maran, M., Brattegaard, K., Vetter, K., Doorly, R. and Gayle, H. (1993). Epidemiology and transmission of HIV-2: why there is no HIV-2 epidemic. *JAMA*. 270, 2083–2086.

De Leys, R., Vanderborght, B., Vanden Haesevelde, M., Heyndrickx, L., van Geel, A., Wauters, C., Bernaerts, R., Saman, E., Nijs, P. and Willems, B. (1990). Isolation and partial characterization of an unusual human immunodeficiency retrovirus from two persons of west-central African origin. *J Virol*. 64, 1207–1216.

Gnann, J., Cormick, J., Michell, S., Nelson, J. and Oldstone, M. (1987). Synthetic peptide immunoassay distinguishes HIV type 1 and type 2 infections. *Science 237*, 1346–1349.

Grez, M., Dietrich, U., Balfe, P., von Briesen, H., Maniar, J., Mahambre, G., Delwart, E., Mullins, J. and Rubsamen-Waigmann, H. (1994). Genetic analysis of Human Immunodeficiency virus type 1 and 2 (HIV-1 and HIV-2) mixed infections in India reveals a recent spread of HIV-1 and HIV-2 from a single ancestor for each of these viruses. *J. Virol*. 68, 2161–2168.

Gürtler, L. G., Hauser, P. H., Eberle, J., von Brunn, A., Knapp, S., Zekeng, L., Tsague, J. M. and Kaptue, L. (1994). A new subtype of Human Immunodeficiency Virus type 1 (MVP-5180) from Cameroon. *J. Virol*. 68, 1581–1585.

Harada, S., Koyanagi, Y. and Yamamoto, N. (1985). Infection of HTLV-III/LAV in HTLV-I-carrying cells MT-2 and MT-4 and application in a plaque assay. *Science*. 229, 563–566.

Hirt, B. (1967). Selective extraction of polyoma DNA from infected mouse cell cultures. *J. Mol. Biol*. 26, 365–369.

Huet, T., Cheynier, R., Meyerhans, A., Roclants, G. and Wain-Hobson, S. (1990). Genetic organization of a chimpanzee lentivirus related to HIV-1. 345, 356–359.

Javaherian, K., Langlois, A. J., LaRosa, G. J., Profy, A. T., Bolognesi, D. P., Herlihy, W. C., Putney, S. D. and Matthews, T. J. (1990). Broadly neutralizing antibodies elicited by the hypervariable neutralizing determinant of HIV-1. *Science*. 250, 1590–1593.

Javaherian, K., Langlois, A. J., Mc Danal, C., Ross, K. L.; Eckler, L. I., Jellis, C. L., Profy, A. T., Rusche, J. R., Bolognesi, D. P., Putney, S. D. and Matthews, T. J. (1989). Principal neutralizing domain of the human immunodeficiency virus type 1 envelope protein. *Proc. Natl. Acad. Sci. USA*. 86, 6768–6772.

Louwagie, J., McCutchan, F., Peeters, M., Brennan, T., Sanders-Buell, E., Eddy, G., van der Groen, G., Fransen, K., Gershy-Damet, G. and Deleys, R. (1993). Phylogenetic analysis of gag genes from 70 international HIV-1 isolates provides evidence for multiple genotypes. *AIDS*. 7, 769–80.

Louwagie, J., McCutchan, F., Van der Groen, G., Peeters, M., Fransen, K., Piot, P., Gershy-Damet, G., Roelants, G., Van Heuverswyn, II. and Eddy, G. (1992). Genetic comparison of HIV-1 isolates from Africa, Europe, and North America. *AIDS Res Hum Retroviruses*. 8, 1467–9.

Matsushita, S. M., Robert-Guroff, M., Rusche, J., Koito, A., Hattori, T., Hoshino, H., Javaherian, K., Takatsuki, K. and Putney, S. (1988). Characterization of a Human immunodeficiency virus neutralizing monoclonal antibody and mapping of the neutralizing epitope. *J. Virol* 62, 2107–2114.

NKENGASONG, J. N. et al., *AIDS* 1993, Vol. 7, No. 11, pp. 1536–1538.

Rey, M. A., Krust, B., Laurent, A. G., Montagnier, L. and Hovanessian, A. G. (1989). Characterization of human immunodeficiency virus type 2 envelope glycoproteins: dimerization of the glycoprotein precursor during processing. *J. Virol*. 63, 647–658.

ULMER J. B. et al., *Science* Vol. 259, March 1993, pp. 1745–1749.

Vanden Heasevelde, M., Decourt, J. L., de Leys, R. J., Vanderborght, B., van der Groen, G., van Heuverswijn, H. and Saman, E. (1994). Genomic cloning and complete sequence analysis of a highly divergent African Human Immunodeficiency Virus isolate. *J. Virol*. 68, 1586–1596.

Vartanian, J. -P., Meyerhans, A., Asjö, B. and Wain-Hobson, S. (1991). Selection, recombination, and G→A hypermutation of HIV-1 genomes. *J. Virol*. 65, 1779–1788.

Wain-Hobson, S., Sonigo, P., Danos, O., Cole, S. and Alizon, M. (1985). Nucleotide sequence of the AIDS virus, LAV. *Cell* 40, 9–17.

SEQUENCE LISTING (1) GENERAL INFORMATION:

(iii) NUMBER OF SEQUENCES: 103

(2) INFORMATION FOR SEQ ID NO: 1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Other nucleic acid
        (A) DESCRIPTION:   /desc = "oligonucleotide"

(xi) SEQUENCE DESCRIPTION: SEQ ID NO: 1:

AGTGGATWYA TAGAAGCAGA AGT                                              23

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "oligonucleotide"

(xi) SEQUENCE DESCRIPTION: SEQ ID NO: 2:

ACTGCYCCTT CHCCTTTCCA                                                  20

(2) INFORMATION FOR SEQ ID NO: 3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "oligonucleotide"

(xi) SEQUENCE DESCRIPTION: SEQ ID NO: 3:

GCTCTAGATG GGGATCTCCC ATGGCAGG                                         28

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "oligonucleotide"

(xi) SEQUENCE DESCRIPTION: SEQ ID NO: 4:

GCTCTAGATC AGGGAAGAAT CCCTGAGTGT                                       30

(2) INFORMATION FOR SEQ ID NO: 5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Cys Lys Asn Arg Leu Ile Cys
1               5

(2) INFORMATION FOR SEQ ID NO: 6:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Arg Leu Leu Ala Leu Glu Thr Phe Ile Gln Asn Trp Trp Leu Leu Asn
1               5                   10                  15

Leu Trp Gly Cys Lys Asn Arg Leu Ile Cys
            20                  25
```

(2) INFORMATION FOR SEQ ID NO: 7:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Arg Ala Arg Leu Leu Ala Leu Glu Thr Phe Ile Gln Asn Gln Gln Leu
1               5                   10                  15

Leu Asn Leu Trp Gly Cys Lys Asn Arg Leu Ile Cys Tyr Thr Ser Val
            20                  25                  30

Lys Trp Asn Lys Thr
        35
```

(2) INFORMATION FOR SEQ ID NO: 8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Ala His Pro Gln Gln Ala
1               5
```

(2) INFORMATION FOR SEQ ID NO: 9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

```
Leu Trp Thr Thr Arg Ala Gly Asn Pro
1               5
```

(2) INFORMATION FOR SEQ ID NO: 10:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Ser Pro Arg Thr Leu Asn Ala Trp Val Lys Ala Val Glu Glu Lys Ala
1               5                   10                  15

Phe Asn Pro Glu Ile Ile Pro Met Phe Met Ala Leu Ser Glu Gly Ala
            20                  25                  30
```

(2) INFORMATION FOR SEQ ID NO: 11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Met Leu Asn Ala Ile Gly Gly His Gln Gly Ala Leu Gln Val Leu Lys
1               5                   10                  15
Glu Val Ile Asn
            20
```

(2) INFORMATION FOR SEQ ID NO: 12:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Gly Pro Leu Pro Pro Gly Gln Ile Arg Glu Pro Thr Gly Ser Asp Ile
1               5                   10                  15
Ala Gly Thr Thr Ser Thr Gln Gln Glu Gln Ile
            20                  25
```

(2) INFORMATION FOR SEQ ID NO: 13:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Ile Pro Val Gly Asp Ile Tyr Arg Lys Trp Ile Val Leu Gly Leu Asn
1               5                   10                  15
Lys Met Val Lys Met Tyr Ser Pro Val Ser Ile Leu Asp Ile
            20                  25                  30
```

(2) INFORMATION FOR SEQ ID NO: 14:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Gln Gly Pro Lys Glu Pro Phe Arg Asp Tyr Val Asp Arg Phe Tyr Lys
1               5                   10                  15
Thr Lys Leu Ala Glu
            20
```

(2) INFORMATION FOR SEQ ID NO: 15:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 15:

Ser Pro Arg Thr Leu Asn Ala Trp Val Lys
1               5                   10

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Gly Ser Asp Ile Ala Gly Thr Thr Ser Thr
1               5                   10

(2) INFORMATION FOR SEQ ID NO: 17:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Gln Gly Pro Lys Glu Pro Phe Arg Asp Tyr Val Asp Arg Phe
1               5                   10

(2) INFORMATION FOR SEQ ID NO: 18:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Asn Pro Glu Ile
1

(2) INFORMATION FOR SEQ ID NO: 19:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Ala Val Glu Glu Lys Ala Phe Asn Pro Glu Ile Ile Pro Met Phe Met
1               5                   10                  15

(2) INFORMATION FOR SEQ ID NO: 20:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 20:

Ile Gly Gly His Gln Gly Ala Leu Gln
1               5

(2) INFORMATION FOR SEQ ID NO: 21:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Arg Glu Pro Thr Gly Ser Asp Ile
1               5

(2) INFORMATION FOR SEQ ID NO: 22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Ile Asn Asp Glu Ala Ala Asp Trp Asp
1               5

(2) INFORMATION FOR SEQ ID NO: 23:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Lys Glu Ile Lys Ile
1               5

(2) INFORMATION FOR SEQ ID NO: 24:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Glu Arg Glu Gly Lys Gly Ala Asn
1               5

(2) INFORMATION FOR SEQ ID NO: 25:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Cys Val Arg Pro Gly Asn Asn Ser Val Lys Glu Ile Lys Ile
1               5                   10

(2) INFORMATION FOR SEQ ID NO: 26:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Gln Ile Glu Arg Glu Gly Lys Gly Ala Asn Ser Arg
1               5                   10

(2) INFORMATION FOR SEQ ID NO: 27:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Cys Val Arg Pro Gly Asn Asn Ser Val Lys Glu Ile Lys Ile Gly Pro
1               5                   10                  15

Met Ala Trp Tyr Ser Met Gln Ile Glu Arg Glu Gly Lys Gly Ala Asn
            20                  25                  30

Ser Arg Thr Ala Phe Cys
        35

(2) INFORMATION FOR SEQ ID NO: 28:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Gly Pro Met Ala Trp Tyr Ser Met
1               5

(2) INFORMATION FOR SEQ ID NO: 29:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Arg Leu Leu Ala Leu Glu Thr Leu Met Gln Asn Gln Gln Leu
1               5                   10

(2) INFORMATION FOR SEQ ID NO: 30:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Leu Asn Leu Trp Gly Cys Arg Gly Lys Ala Ile Cys Tyr Thr Ser Val
1               5                   10                  15

Gln Trp Asn Glu Thr Trp Gly
            20

(2) INFORMATION FOR SEQ ID NO: 31:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Cys Arg Gly Lys Ala Ile
1               5

(2) INFORMATION FOR SEQ ID NO: 32:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Ser Val Gln Trp Asn
1               5

(2) INFORMATION FOR SEQ ID NO: 33:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Arg Leu Leu Ala Leu Glu Thr Leu Met Gln Asn Gln Gln Leu Leu Asn Leu
1               5                   10                  15

Trp Gly Cys Arg Gly Lys Ala Ile Cys Tyr Thr Ser
            20                  25

(2) INFORMATION FOR SEQ ID NO: 34:

```
        (i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 34:

Gln Asn Gln Gln Leu Leu Asn Leu Trp Gly Cys Arg Gly Lys Ala Ile
1               5                   10                  15
Cys Tyr Thr Ser Val Gln Trp Asn
            20

(2) INFORMATION FOR SEQ ID NO: 35:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 35:

Arg Ile Leu Ala Val Glu Arg Tyr
1               5

(2) INFORMATION FOR SEQ ID NO: 36:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 36:

Ser Gly Lys Leu Ile Cys
1               5

(2) INFORMATION FOR SEQ ID NO: 37:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 37:

Gly Pro Gly Arg Ala Phe
1               5

(2) INFORMATION FOR SEQ ID NO: 38:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 38:

Gly Pro Met Ala Trp Tyr
1               5
```

(2) INFORMATION FOR SEQ ID NO: 39:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

```
Gly Pro Met Arg Trp Arg
1               5
```

(2) INFORMATION FOR SEQ ID NO: 40:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

```
Thr Phe Ile Gln Asn
1               5
```

(2) INFORMATION FOR SEQ ID NO: 41:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

```
Trp Gly Cys Lys Asn Arg
1               5
```

(2) INFORMATION FOR SEQ ID NO: 42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "oligonucleotide"

(xi) SEQUENCE DESCRIPTION: SEQ ID NO: 42:

```
ATTCCAATAC ACTATTGTGC TCCA                                      24
```

(2) INFORMATION FOR SEQ ID NO: 43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "oligonucleotide"

(xi) SEQUENCE DESCRIPTION: SEQ ID NO: 43:

```
AAAGAATTCT CCATGACTGT TAAA                                                    24
```

(2) INFORMATION FOR SEQ ID NO: 44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "oligonucleotide"

(xi) SEQUENCE DESCRIPTION: SEQ ID NO: 44:

```
GGTATAGTGC AACAGCAGGA CAAC                                                    24
```

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc = "oligonucleotide"

(xi) SEQUENCE DESCRIPTION: SEQ ID NO: 45:

```
AGAGGCCCAT TCATCTAACT C                                                       21
```

(2) INFORMATION FOR SEQ ID NO: 46:

(i) SEQUENCE CHARACTERISTICS:
        (A) LENGTH: 526 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 46:

```
Met Thr Ala Ile Met Lys Ala Met Gly Lys Arg Asn Arg Lys Leu Gly
 1               5                  10                  15

Ile Trp Cys Leu Ile Leu Ala Leu Ile Ile Pro Cys Leu Ser Cys Asn
                20                  25                  30

Gln Leu Tyr Ala Thr Val Tyr Ser Gly Val Pro Val Trp Glu Asp Ala
            35                  40                  45

Lys Pro Thr Leu Phe Cys Ala Ser Asp Ala Asn Leu Thr Ser Thr Glu
        50                  55                  60

Gln His Asn Ile Trp Ala Thr Gln Ala Cys Val Pro Thr Asp Pro Ser
 65                  70                  75                  80

Pro Asn Glu Tyr Glu Leu Lys Asn Val Thr Gly Lys Phe Asn Ile Trp
                85                  90                  95

Lys Asn Tyr Ile Val Asp Gln Met His Glu Asp Ile Ile Asp Leu Trp
            100                 105                 110

Asp Gln Ser Leu Lys Pro Cys Val Gln Met Thr Phe Leu Cys Val Gln
        115                 120                 125

Met Asn Cys Thr Asp Ile Lys Asn Ser Ile Asn Thr Thr Asn Ser Pro
    130                 135                 140

Leu Asn Ser Asn Asn Thr Lys Glu Val Lys Gln Cys Asp Phe Asn Val
145                 150                 155                 160

Thr Thr Val Leu Lys Asp Lys Glu Lys Lys Gln Ala Leu Phe Tyr
                165                 170                 175
```

```
Val Thr Asp Leu Val Lys Ile Asn Ala Thr Ser Asn Glu Thr Met Tyr
            180                 185                 190

Arg Leu Ile Asn Cys Asn Ser Thr Thr Ile Arg Gln Ala Cys Pro Lys
        195                 200                 205

Val Ser Phe Glu Pro Ile Pro Ile His Tyr Cys Ala Pro Ala Gly Cys
    210                 215                 220

Ala Ile Phe Lys Cys Asn Glu Thr Gly Phe Asn Gly Thr Gly Leu Cys
225                 230                 235                 240

Lys Asn Val Thr Val Thr Cys Thr His Gly Ile Lys Pro Thr Val
                245                 250                 255

Ser Thr Gln Leu Ile Leu Asn Gly Thr Leu Ser Lys Gly Asn Ile Thr
            260                 265                 270

Ile Met Gly Lys Asn Ile Ser Asp Ser Gly Glu Asn Ile Leu Ile Thr
        275                 280                 285

Leu Asn Thr Asn Ile Thr Ile Ala Cys Glu Arg Pro Gly Asn Gln Thr
        290                 295                 300

Ile Gln Lys Ile Met Ala Gly Pro Met Ala Trp Tyr Ser Met Ala Leu
305                 310                 315                 320

Ser Asn Thr Lys Gly Asp Thr Arg Ala Ala Tyr Cys Asn Tyr Ser Ala
                325                 330                 335

Thr Asp Trp Asn Lys Ala Leu Lys Asn Ile Thr Glu Arg Tyr Leu Glu
            340                 345                 350

Leu Val Glu Tyr Asn Gln Thr Asp Val Thr Met Lys Phe Gly Asn His
            355                 360                 365

Ser Gly Glu Asp Ala Glu Val Thr Asn Phe Phe Asn Cys His Gly
        370                 375                 380

Glu Phe Phe Tyr Cys Asn Thr Asn Arg Leu Phe Asn His Thr Phe Ser
385                 390                 395                 400

Cys Lys Lys Asn Met Thr Asn Asn Lys Ile Asn Cys Thr Asn Ile Ser
                405                 410                 415

Asn Asn Ser Asn Gly Thr Gln Ala Ile Pro Cys Arg Leu Arg Gln Val
            420                 425                 430

Val Arg Asp Trp Met Arg Gly Gly Ser Gly Leu Tyr Ala Pro Pro Ile
        435                 440                 445

Pro Gly Asn Leu Val Cys Arg Ser Asn Ile Thr Gly Met Ile Leu Gln
    450                 455                 460

Leu Asp Thr Pro Trp Asn Lys Thr His Pro Asn Ser Thr Thr Leu Arg
465                 470                 475                 480

Pro Gly Gly Gly Asp Met Lys Asp Ile Trp Arg Thr Gln Leu Phe Lys
                485                 490                 495

Tyr Lys Val Val Arg Val Lys Pro Phe Ser Val Ala Pro Thr Lys Ile
            500                 505                 510

Ala Arg Pro Thr Ile Gly Thr Arg Ser His Arg Glu Lys Arg
            515                 520                 525

(2) INFORMATION FOR SEQ ID NO: 47:

(i) SEQUENCE CHARACTERISTICS:
        (A) LENGTH: 351 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 47:
```

```
Ala Ala Gly Leu Ala Met Leu Phe Leu Gly Ile Leu Ser Ala Ala Gly
 1               5                  10                 15

Ser Thr Met Gly Ala Ala Ala Thr Ala Leu Thr Val Arg Thr Gln His
            20                  25                  30

Leu Ile Lys Gly Ile Val Gln Gln Asp Asn Leu Leu Arg Ala Ile
            35                  40                  45

Gln Ala Gln Gln His Leu Leu Arg Pro Ser Val Trp Gly Ile Arg Gln
 50                  55                  60

Leu Arg Ala Arg Leu Leu Ala Leu Glu Thr Phe Ile Gln Asn Gln Gln
 65                  70                  75                  80

Leu Leu Asn Leu Trp Gly Cys Lys Asn Arg Leu Ile Cys Tyr Thr Ser
                 85                  90                  95

Val Lys Trp Asn Lys Thr Trp Gly Gly Asp Asn Glu Ser Ile Trp Asp
                100                 105                 110

Glu Leu Thr Trp Gln Gln Trp Asp Gln Gln Ile Asn Asn Val Ser Ser
                115                 120                 125

Phe Ile Tyr Glu Lys Ile Gln Glu Ala Gln Glu Gln Gln Glu Lys Asn
 130                 135                 140

Glu Lys Glu Leu Leu Glu Leu Asp Glu Trp Ala Ser Ile Trp Asn Trp
 145                 150                 155                 160

Leu Asp Ile Thr Lys Trp Leu Trp Tyr Ile Lys Ile Ala Ile Ile Ile
                165                 170                 175

Val Gly Ala Leu Ile Gly Val Arg Val Val Met Ile Val Leu Asn Leu
                180                 185                 190

Val Lys Asn Ile Arg Gln Gly Tyr Gln Pro Leu Ser Leu Gln Ile Pro
 195                 200                 205

Ile Gln Gln Gln Ala Glu Val Gly Thr Pro Gly Gly Thr Gly Glu Gly
 210                 215                 220

Gly Gly Asp Glu Asp Arg Arg Arg Trp Thr Pro Leu Pro Gln Gly Phe
 225                 230                 235                 240

Leu His Leu Leu Tyr Thr Asp Leu Arg Thr Ile Ile Leu Trp Ile Tyr
                245                 250                 255

His Leu Leu Ser Asn Leu Ala Ser Glu Ile Gln Lys Leu Ile Arg His
                260                 265                 270

Leu Gly Leu Gly Leu Trp Ile Ile Gly Gln Arg Thr Ile Glu Ala Cys
 275                 280                 285

Arg Leu Phe Lys Ala Ile Ile Gln Tyr Trp Leu Gln Glu Leu Gln Thr
 290                 295                 300

Ser Ala Thr Asn Leu Leu Asp Thr Val Ala Val Ala Val Ala Asn Trp
 305                 310                 315                 320

Thr Asp Ser Thr Ile Leu Gly Ile Gln Ser Ile Gly Arg Gly Ile Leu
                325                 330                 335

Asn Ile Pro Arg Arg Ile Arg Gln Gly Leu Glu Arg Leu Leu Leu
                340                 345                 350

(2) INFORMATION FOR SEQ ID NO: 48:

(i) SEQUENCE CHARACTERISTICS:
        (A) LENGTH: 516 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 48:
```

-continued

```
Met Arg Val Lys Glu Lys Tyr Gln His Leu Trp Arg Trp Gly Trp Lys
  1               5                       10                      15

Trp Gly Thr Met Leu Leu Gly Ile Leu Met Ile Cys Ser Ala Thr Glu
                20                      25                  30

Lys Leu Trp Val Thr Val Tyr Tyr Gly Val Pro Val Trp Lys Glu Ala
                35                      40                  45

Thr Thr Thr Leu Phe Cys Ala Ser Asp Ala Lys Ala Tyr Asp Thr Glu
            50                      55                  60

Val His Asn Val Trp Ala Thr His Ala Cys Val Pro Thr Asp Pro Asn
 65                      70                  75                  80

Pro Gln Glu Val Val Leu Val Asn Val Thr Glu Asn Phe Asn Met Trp
                        85                  90                  95

Lys Asn Asp Met Val Glu Gln Met His Glu Asp Ile Ile Ser Leu Trp
                100                     105                 110

Asp Gln Ser Leu Lys Pro Cys Val Lys Leu Thr Pro Leu Cys Val Ser
                115                     120                 125

Leu Lys Cys Thr Asp Leu Gly Asn Ala Thr Asn Thr Asn Ser Ser Asn
        130                     135                 140

Thr Asn Ser Ser Ser Gly Glu Met Met Met Glu Lys Gly Glu Ile Lys
145                     150                     155                 160

Asn Cys Ser Phe Asn Ile Ser Thr Ser Ile Arg Gly Lys Val Gln Lys
                    165                     170                 175

Glu Tyr Ala Phe Phe Tyr Lys Leu Asp Ile Ile Pro Ile Asp Asn Asp
                180                     185                 190

Thr Thr Ser Tyr Thr Leu Thr Ser Cys Asn Thr Ser Val Ile Thr Gln
                195                     200                 205

Ala Cys Pro Lys Val Ser Phe Glu Pro Ile Pro Ile His Tyr Cys Ala
210                     215                     220

Pro Ala Gly Phe Ala Ile Leu Lys Cys Asn Asn Lys Thr Phe Asn Gly
225                     230                     235                 240

Thr Gly Pro Cys Thr Asn Val Ser Thr Val Gln Cys Thr His Gly Ile
                    245                     250                 255

Arg Pro Val Val Ser Thr Gln Leu Leu Leu Asn Gly Ser Leu Ala Glu
                260                     265                 270

Glu Glu Val Val Ile Arg Ser Ala Asn Phe Thr Asp Asn Ala Lys Thr
            275                     280                 285

Ile Ile Val Gln Leu Asn Gln Ser Val Glu Ile Asn Cys Thr Arg Pro
290                     295                     300

Asn Asn Asn Thr Arg Lys Ser Ile Arg Ile Gln Arg Gly Pro Gly Arg
305                     310                     315                 320

Ala Phe Val Thr Ile Gly Lys Ile Gly Asn Met Arg Gln Ala His Cys
                    325                     330                 335

Asn Ile Ser Arg Ala Lys Trp Asn Ala Thr Leu Lys Gln Ile Ala Ser
                340                     345                 350

Lys Leu Arg Glu Gln Phe Gly Asn Asn Lys Thr Ile Ile Phe Lys Gln
            355                     360                 365

Ser Ser Gly Gly Asp Pro Glu Ile Val Thr His Ser Phe Asn Cys Gly
370                     375                     380

Gly Glu Phe Phe Tyr Cys Asn Ser Thr Gln Leu Phe Asn Ser Thr Trp
385                     390                     395                 400

Phe Asn Ser Thr Trp Ser Thr Glu Gly Ser Asn Asn Thr Glu Gly Ser
                405                     410                     415
```

```
Asp Thr Ile Thr Leu Pro Cys Arg Ile Lys Gln Phe Ile Asn Met Trp
            420                 425                 430

Gln Glu Val Gly Lys Ala Met Tyr Ala Pro Pro Ile Ser Gly Gln Ile
            435                 440                 445

Arg Cys Ser Ser Asn Ile Thr Gly Leu Leu Leu Thr Arg Asp Gly Gly
            450                 455                 460

Asn Asn Asn Asn Gly Ser Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
            500                 505                 510

Arg Glu Lys Arg
            515

(2) INFORMATION FOR SEQ ID NO: 49:

(i) SEQUENCE CHARACTERISTICS:
        (A) LENGTH: 345 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 49:

Ala Val Gly Ile Gly Ala Leu Phe Leu Gly Phe Leu Gly Ala Ala Gly
1               5                   10                  15

Ser Thr Met Gly Ala Arg Ser Met Thr Leu Thr Val Gln Ala Arg Gln
            20                  25                  30

Leu Leu Ser Gly Ile Val Gln Gln Gln Asn Asn Leu Leu Arg Ala Ile
            35                  40                  45

Glu Ala Gln Gln His Leu Leu Gln Leu Thr Val Trp Gly Ile Lys Gln
            50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn Asn Met Thr Trp Met Glu Trp Asp Arg Glu Ile Asn Asn Tyr Thr
            115                 120                 125

Ser Leu Ile His Ser Leu Ile Glu Glu Ser Gln Asn Gln Gln Glu Lys
            130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Ile Phe Ile Met
                165                 170                 175

Ile Val Gly Gly Leu Val Gly Leu Arg Ile Val Phe Ala Val Leu Ser
            180                 185                 190

Ile Val Asn Arg Val Arg Gln Gly Tyr Ser Pro Leu Ser Phe Gln Thr
            195                 200                 205

His Leu Pro Thr Pro Arg Gly Pro Asp Arg Pro Glu Gly Ile Glu Glu
            210                 215                 220

Glu Gly Gly Glu Arg Asp Arg Asp Arg Ser Ile Arg Leu Val Asn Gly
225                 230                 235                 240
```

```
Ser Leu Ala Leu Ile Trp Asp Asp Leu Arg Ser Leu Cys Leu Phe Ser
                245                 250                 255

Tyr His Arg Leu Arg Asp Leu Leu Ile Val Thr Arg Ile Val Glu
            260                 265                 270

Leu Leu Gly Arg Arg Gly Trp Glu Ala Leu Lys Tyr Trp Trp Asn Leu
            275                 280                 285

Leu Gln Tyr Trp Ser Gln Glu Leu Lys Asn Ser Ala Val Ser Leu Leu
        290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335

Arg Gln Gly Leu Glu Arg Ile Leu Leu
            340                 345

(2) INFORMATION FOR SEQ ID NO: 50:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys
            20                  25

(2) INFORMATION FOR SEQ ID NO: 51:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Arg Ile Leu Ala Val Glu Arg Tyr Leu Lys Asp Gln Gln Leu Leu Gly
1               5                   10                  15

Ile Trp Gly Cys Ser Gly Lys Ile Ile Cys
            20                  25

(2) INFORMATION FOR SEQ ID NO: 52:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

Arg Ile Leu Ala Val Glu Arg Tyr Leu Lys Asp Gln Gln Leu Leu Gly
1               5                   10                  15

Ile Trp Gly Cys Ser Gly Lys His Ile Cys
            20                  25
```

(2) INFORMATION FOR SEQ ID NO: 53:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 53:

Arg Val Leu Ala Val Glu Arg Tyr Leu Lys Asp Gln Gln Leu Met Gly
1               5                   10                  15

Ile Trp Gly Cys Ser Gly Lys Leu Ile Cys
            20                  25

(2) INFORMATION FOR SEQ ID NO: 54:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 54:

Arg Val Leu Ala Val Glu Arg Tyr Leu Arg Asp Gln Gln Leu Leu Gly
1               5                   10                  15

Ile Trp Gly Cys Ser Gly Lys Leu Ile Cys
            20                  25

(2) INFORMATION FOR SEQ ID NO: 55:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

Arg Val Leu Ala Val Glu Arg Tyr Leu Arg Asp Gln Gln Leu Leu Gly
1               5                   10                  15

Ile Trp Gly Cys Ser Gly Arg His Ile Cys
            20                  25

(2) INFORMATION FOR SEQ ID NO: 56:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

Arg Val Leu Ala Val Glu Arg Tyr Leu Gln Asp Gln Arg Leu Leu Gly
1               5                   10                  15

Met Trp Gly Cys Ser Gly Lys His Ile Cys
            20                  25

(2) INFORMATION FOR SEQ ID NO: 57:

(i) SEQUENCE CHARACTERISTICS:

(A) LENGTH: 26 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 57:

Arg Leu Leu Ala Val Glu Arg Tyr Leu Gln Asp Gln Gln Ile Leu Gly
1               5                   10                  15

Leu Trp Gly Cys Ser Gly Lys Ala Val Cys
            20                  25

(2) INFORMATION FOR SEQ ID NO: 58:

(i) SEQUENCE CHARACTERISTICS:
                (A) LENGTH: 26 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 58:

Arg Leu Leu Ala Leu Glu Thr Phe Ile Gln Asn Gln Gln Leu Leu Asn
1               5                   10                  15

Leu Trp Gly Cys Lys Asn Arg Leu Ile Cys
            20                  25

(2) INFORMATION FOR SEQ ID NO: 59:

(i) SEQUENCE CHARACTERISTICS:
                (A) LENGTH: 26 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 59:

Arg Leu Gln Ala Leu Glu Thr Leu Ile Gln Asn Gln Gln Arg Leu Asn
1               5                   10                  15

Leu Trp Gly Cys Lys Gly Lys Leu Ile Cys
            20                  25

(2) INFORMATION FOR SEQ ID NO: 60:

(i) SEQUENCE CHARACTERISTICS:
                (A) LENGTH: 26 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 60:

Arg Leu Leu Ala Leu Glu Thr Leu Leu Gln Asn Gln Gln Leu Leu Ser
1               5                   10                  15

Leu Trp Gly Cys Lys Gly Lys Leu Val Cys
            20                  25

(2) INFORMATION FOR SEQ ID NO: 61:

(i) SEQUENCE CHARACTERISTICS:
                (A) LENGTH: 26 amino acids
                (B) TYPE: amino acid
                (C) STRANDEDNESS: single (D) TOPOLOGY: linear (ii) MOLECULE TYPE: peptide (xi) SEQUENCE DESCRIPTION: SEQ ID NO: 61:

Arg Val Thr Ala Ile Glu Lys Tyr Leu Gln Asp Gln Ala Arg Leu Asn
1               5                   10                  15
Ser Trp Gly Cys Ala Phe Arg Gln Val Cys
            20                  25

(2) INFORMATION FOR SEQ ID NO: 62:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

Arg Val Thr Ala Ile Glu Lys Tyr Leu Lys Asp Gln Ala Gln Leu Asn
1               5                   10                  15
Ser Trp Gly Cys Ala Phe Arg Gln Val Cys
            20                  25

(2) INFORMATION FOR SEQ ID NO: 63:

(i) SEQUENCE CHARACTERISTICS:
        (A) LENGTH: 2621 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 63:

```
ATGACAGCGA TTATGAAAGC AATGGGGAAG AGGAACAGGA AGTTAGGGAT CTGGTGCTTG      60
ATTTTGGCTT TGATAATCCC ATGTTTGAGC TGTAACCAAC TATATGCCAC AGTCTATTCT     120
GGGGTACCTG TATGGGAAGA TGCAAAACCA ACATTGTTCT GTGCTTCAGA TGCTAACTTG     180
ACAAGCACTG AACAGCATAA TATTTGGGCA CACACAAGCCT GTGTTCCCAC AGACCCCAGT    240
CCAAATGAAT ATGAGCTAAA AAATGTGACA GGTAAATTCA ATATATGGAA AAATTATATA     300
GTAGACCAAA TGCACGAAGA CATTATAGAT TTGTGGGACC AGAGTTTAAA ACCTTGTGTT     360
CAAATGACTT TCTTGTGTGT ACAAATGAAT TGTACAGATA TCAAAAATAG TATTAATACC     420
ACAAACAGTC CCTTAAACTC AAACAATACA AAGAGGGTGA AACAGTGTGA CTTTAATGTA     480
ACTACAGTGC TCAAAGACAA ACAGGAGAAA AAACAGGCTC TATTCTATGT GACAGATTTG     540
GTTAAGATTA ACGCCACATC AAATGAAACA ATGTATAGAT TAATTAATTG TAACTCCACA     600
ACCATCAGGC AGGCCTGTCC AAAGGTATCT TTTGAGCCCA TTCCCATACA CTATTGTGCT     660
CCAGCGGGAT GTGCCATCTT TAAGTGTAAT GAAACAGGAT TTAATGGAAC AGGTCTCTGT     720
AAAAACGTTA CAGTAGTTAC TTGTACACAT GGCATCAAAC CAACAGTAAG TACCCAACTA     780
ATACTAAATG GACACTCTCT AAAGGAAAT ATAACAATCA TGGGAAAGAA TATTTCAGAC     840
AGTGGGGAGA ACATCCTAAT AACCCTAAAT ACTAATATAA CAATAGCATG TGAGAGACCA     900
GGAAATCAGA CAATACAAAA GATAATGGCA GGTCCAATGG CTTGGTACAG CATGGCCCTT     960
AGTAATACAA AGGGGGATAC AAGGGCAGCT TATTGTAATT ATAGTGCCAC TGACTGGAAC    1020
AAAGCCTTAA AAACATAAC TGAAAGATAT TTAGAACTTG TAGAATATAA TCAAACTGAT    1080
```

```
GTTACCATGA AATTCGGTAA TCACAGTGGT GAAGATGCAG AAGTAACAAA TTTCTTTTTT      1140

AACTGTCATG GAGAATTCTT TTATTGTAAC ACAAATCGGC TGTTTAATCA TACCTTTTCC      1200

TGCAAGAAGA ATATGACCAA TAACAAGATC AATTGTACTA ATATTAGCAA TAATAGCAAT      1260

GGCACTCAGG CAATACCTTG CAGGTTGAGA CAAGTAGTAA GGGACTGGAT TCGGGACTTT      1320

ATGCACCTCC CATCCCAGGA AACCTAGTAT GCAGGTCAAA CATAACTGGA ATGATTCTAC      1380

AATTGGACAC GCCATGGAAT AAAACACATC CTAACAGCAC CACCCTTAGA CCAGGAGGGG      1440

GAGATATGAA AGATATATGG AGAACTCAAT TGTTCAAATA TAAAGTAGTA AGAGTAAAAC      1500

CTTTTAGTGT AGCACCAACA AAAATTGCAA GGCCAACTAT AGGAACTAGA TCTCATAGAG      1560

AGAAAAGAGC AGCAGGTTTG GCAATGCTAT TCTTGGGGAT TCTAAGTGCA GCAGGAAGCA      1620

CTATGGGCGC AGCGGCAACA GCGCTGACGG TACGGACCCA GCATCTGATA AGGGTATAG      1680

TGCAACAGCA GGATAACCTG CTAAGAGCAA TACAGGCCCA GCAACACTTG CTGAGGCCAT      1740

CTGTATGGGG TATTAGACAA CTCCGAGCTC GCCTGCTAGC CTTAGAAACC TTTATACAGA      1800

ATCAGCAACT CCTTAACCTG TGGGGCTGCA AGAATAGACT AATCTGCTAC ACATCAGTAA      1860

AGTGGAATAA AACATGGGGA GGAGATAATG AATCAATTTG GGATGAGTTA ACATGGCAGC      1920

AGTGGGATCA ACAGATAAAC AACGTAAGCT CCTTCATATA TGAAAAAATA CAAGAGGCAC      1980

AAGAACAACA GGAGAAAAAT GAGAAAGAAT TGCTGGAGTT AGATGAATGG GCCTCTATTT      2040

GGAATTGGCT TGACATAACT AAATGGTTGT GGTATATAAA AATAGCTATA ATCATAGTAG      2100

GAGCACTAAT AGGTGTAAGA GTAGTTATGA TAGTACTTAA TCTAGTAAAG AACATTAGGC      2160

AGGGATATCA ACCCCTCTCG TTACAGATCC CCATCCAACA ACAAGCGGAA GTAGGAACGC      2220

CAGGAGGAAC AGGAGAAGGA GGTGGAGACG AAGACAGGCG CAGGTGGACT CCATTGCCGC      2280

AAGGGTTCTT GCATCTGTTG TACACGGACC TCAGGACAAT AATCTTGTGG ATTTACCACC      2340

TCTTGAGCAA CTTAGCCTCA GAGATCCAGA AGTTGATCAG ACACCTGGGA CTTGGACTAT      2400

GGATCATAGG GCAGAGGACA ATTGAAGCTT GCAGACTCTT TAAAGCTATA ATACAATACT      2460

GGCTACAAGA ATTGCAAACT AGTGCTACAA ATCTACTAGA TACTGTTGCA GTGGCAGTTG      2520

CTAATTGGAC TGACAGCACA ATCTTAGGCA TACAAAGCAT AGGGAGAGGG ATTCTTAACA      2580

TACCAAGAAG GATTAGACAG GGCCTTGAAC GACTCCTGTT A                         2621
```

(2) INFORMATION FOR SEQ ID NO: 64:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 64:

```
GCAGAGACAG GACAGGAAAC TGCCTACTTC CTGTTAAAAT TAGCAGCAAG ATGGCCTATT        60

AAAATACTAC ATACAGACAA TGGGCCTAAC TTTACAAGTG CAGCCATGAA AGCTGCATGT       120

TGGTGGACAA ACATACAACA TGAGTTTGGA ATACCATACA ATCCACAAAG TCAAGGAGTA       180

GTAGAAGCCA TGAACAAGGA ATTAAAATCA ATCATACAGG TGAGGGACCA AGCAGAGCAC       240

TTAAGGACAG CAGTACAAAT GGCAGTATTT GTTCACAATT TTAAAAGAAA AGGGGGGATT       300

GGGGGGTACA CTGCAGGAGA GAGATTAATA GACATATTAG CATCACAAAT ACAAACAACA       360

GAACTACAAA AACAAATTTT AAAAATTCAA AATTTTCGGG TCTATTACAG AGACAGCAGA       420
```

GACCCTATTT GGAAAGGACC GGCACAGCTC CTG                                                      453

(2) INFORMATION FOR SEQ ID NO: 65:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

```
Gln Gly Gln Met Val His Gln Ala Leu Ser Pro Arg Thr Leu Asn Ala
1               5                   10                  15

Trp Val Lys Ala Val Glu Glu Lys Ala Phe Asn Pro Glu Ile Ile Pro
            20                  25                  30

Met Phe Met Ala Leu Ser Glu Gly Ala Val Pro Tyr Asp Ile Asn Val
        35                  40                  45

Met Leu Asn Ala Ile Gly Gly His Gln Gly Ala Leu Gln Val Leu Lys
    50                  55                  60

Glu Val Ile Asn Asp Glu Ala Ala Asp Trp Asp Arg Ala His Pro Gln
65                  70                  75                  80

Gln Ala Gly Pro Leu Pro Pro Gly Gln Ile Arg Glu Pro Thr Gly Ser
                85                  90                  95

Asp Ile Ala Gly Thr Thr Ser Thr Gln Gln Glu Gln Ile Leu Trp Thr
            100                 105                 110

Thr Arg Ala Gly Asn Pro Ile Pro Val Gly Asp Ile Tyr Arg Lys Trp
        115                 120                 125

Ile Val Leu Gly Leu Asn Lys Met Val Lys Met Tyr Ser Pro Val Ser
    130                 135                 140

Ile Leu Asp Ile Arg Gln Gly Pro Lys Glu Pro Phe Arg Asp Tyr Val
145                 150                 155                 160

Asp Arg Phe Tyr Lys Thr Leu Arg Ala Glu
                165                 170
```

(2) INFORMATION FOR SEQ ID NO: 66:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

```
Gln Gly Gln Met Val His Gln Ala Ile Ser Pro Arg Thr Leu Asn Ala
1               5                   10                  15

Trp Val Lys Ala Val Glu Glu Lys Ala Phe Asn Pro Glu Ile Ile Pro
            20                  25                  30

Met Phe Met Ala Leu Ser Glu Gly Ala Ile Ser Tyr Asp Ile Asn Thr
        35                  40                  45

Met Leu Asn Ala Ile Gly Gly His Gln Gly Ala Leu Gln Val Leu Lys
    50                  55                  60

Glu Val Ile Asn Glu Glu Ala Val Glu Trp Asp Arg Thr His Pro Pro
65                  70                  75                  80

Pro Val Gly Pro Leu Pro Pro Gly Gln Ile Arg Glu Pro Thr Gly Ser
                85                  90                  95
```

```
Asp Ile Ala Gly Thr Thr Ser Thr Gln Gln Glu Gln Ile His Trp Thr
            100                 105                 110

Thr Arg Pro Asn Gln Pro Ile Pro Val Gly Asp Ile Tyr Arg Lys Trp
        115                 120                 125

Ile Val Leu Gly Leu Asn Lys Met Val Lys Met Tyr Ser Pro Val Ser
    130                 135                 140

Ile Leu Asp Ile Lys Gln Gly Pro Lys Glu Pro Phe Arg Asp Tyr Val
145                 150                 155                 160

Asp Arg Phe Tyr Lys Thr Leu Arg Ala Glu
                165                 170

(2) INFORMATION FOR SEQ ID NO: 67:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

Gln Gly Gln Met Val His Gln Ala Ile Ser Pro Arg Thr Leu Asn Ala
1               5                   10                  15

Trp Val Lys Ala Val Glu Glu Lys Ala Phe Asn Pro Glu Ile Ile Pro
            20                  25                  30

Met Phe Met Ala Leu Ser Glu Gly Ala Val Pro Tyr Asp Ile Asn Thr
        35                  40                  45

Met Leu Asn Ala Ile Gly Gly His Gln Gly Ala Leu Gln Val Leu Lys
    50                  55                  60

Glu Val Ile Asn Glu Glu Ala Ala Glu Trp Asp Arg Thr His Pro Pro
65                  70                  75                  80

Ala Met Gly Pro Leu Pro Pro Gly Gln Ile Arg Glu Pro Thr Gly Ser
                85                  90                  95

Asp Ile Ala Gly Thr Thr Ser Thr Gln Gln Glu Gln Ile Ile Trp Thr
            100                 105                 110

Thr Arg Gly Ala Asn Ser Ile Pro Val Gly Asp Ile Tyr Arg Lys Trp
        115                 120                 125

Ile Val Leu Gly Leu Asn Lys Met Val Lys Met Tyr Ser Pro Val Ser
    130                 135                 140

Ile Leu Asp Ile Arg Gln Gly Pro Lys Glu Pro Phe Arg Asp Tyr Val
145                 150                 155                 160

Asp Arg Phe Tyr Lys Thr Leu Arg Ala Glu
                165                 170

(2) INFORMATION FOR SEQ ID NO: 68:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 68:

Gln Gly Gln Met Val His Gln Ala Ile Ser Pro Arg Thr Leu Asn Ala
1               5                   10                  15

Trp Val Lys Val Val Glu Glu Lys Ala Phe Ser Pro Glu Val Ile Pro
```

-continued

```
                20                  25                  30
Met Phe Ser Ala Leu Ser Glu Gly Ala Thr Pro Gln Asp Leu Asn Thr
                35                  40                  45

Met Leu Asn Thr Val Gly Gly His Gln Ala Ala Met Gln Met Leu Lys
 50                  55                  60

Glu Thr Ile Asn Glu Glu Ala Ala Glu Trp Asp Arg Val His Pro Val
 65                  70                  75                  80

His Ala Gly Pro Ile Ala Pro Gly Gln Met Arg Glu Pro Arg Gly Ser
                 85                  90                  95

Asp Ile Ala Gly Thr Thr Ser Thr Leu Gln Glu Gln Ile Gly Trp Met
                100                 105                 110

Thr Asn Asn Pro Pro Ile Pro Val Gly Glu Ile Tyr Lys Arg Trp Ile
                115                 120                 125

Ile Leu Gly Leu Asn Lys Ile Val Arg Met Tyr Ser Pro Thr Ser Ile
            130                 135                 140

Leu Asp Ile Arg Gln Gly Pro Lys Glu Pro Phe Arg Asp Tyr Val Asp
145                 150                 155                 160

Arg Phe Tyr Lys Thr Leu Arg Ala Glu
                165
```

(2) INFORMATION FOR SEQ ID NO: 69:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 69:

```
Gln Gly Gln Met Ile His Gln Ala Ile Ser Pro Arg Thr Leu Asn Ala
 1               5                  10                  15

Trp Val Lys Val Ile Glu Glu Lys Ala Phe Ser Pro Glu Val Ile Pro
                20                  25                  30

Met Phe Ser Ala Leu Ser Glu Gly Ala Thr Pro Gln Asp Leu Asn Met
                35                  40                  45

Met Leu Asn Ile Val Gly Gly His Gln Ala Ala Met Gln Met Leu Lys
 50                  55                  60

Asp Thr Ile Asn Glu Glu Ala Ala Asp Trp Asp Arg Val His Pro Val
 65                  70                  75                  80

His Ala Gly Pro Ile Pro Pro Gly Gln Met Arg Glu Pro Arg Gly Ser
                 85                  90                  95

Asp Ile Ala Gly Thr Thr Ser Thr Leu Gln Glu Gln Ile Gly Trp Met
                100                 105                 110

Thr Ser Asn Pro Pro Ile Pro Val Gly Asp Ile Tyr Lys Arg Trp Ile
                115                 120                 125

Ile Leu Gly Leu Asn Lys Ile Val Arg Met Tyr Ser Pro Val Ser Ile
            130                 135                 140

Leu Asp Ile Arg Gln Gly Pro Lys Glu Pro Phe Arg Asp Tyr Val Asp
145                 150                 155                 160

Arg Phe Phe Lys Thr Leu Arg Ala Glu
                165
```

(2) INFORMATION FOR SEQ ID NO: 70:

(i) SEQUENCE CHARACTERISTICS:

(A) LENGTH: 169 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 70:

Gln Gly Gln Met Val His Gln Ala Ile Ser Pro Arg Thr Leu Asn Ala
1               5                   10                  15

Trp Val Lys Val Val Glu Glu Lys Ala Phe Ser Pro Glu Val Ile Pro
                20                  25                  30

Met Phe Ser Ala Leu Ser Glu Gly Ala Leu Pro Gln Asp Val Asn Thr
            35                  40                  45

Met Leu Asn Ala Val Gly Gly His Gln Gly Ala Met Gln Val Leu Lys
        50                  55                  60

Glu Val Ile Asn Glu Glu Ala Ala Glu Trp Asp Arg Leu His Pro Thr
65                  70                  75                  80

His Ala Gly Pro Ile Ala Pro Gly Gln Leu Arg Glu Pro Arg Gly Ser
                85                  90                  95

Asp Ile Ala Gly Thr Thr Ser Thr Leu Gln Glu Gln Ile Gly Trp Thr
            100                 105                 110

Thr Ala Asn Pro Pro Ile Pro Val Gly Asp Val Tyr Arg Arg Trp Val
        115                 120                 125

Ile Leu Gly Leu Asn Lys Val Val Arg Met Tyr Cys Pro Val Ser Ile
130                 135                 140

Leu Asp Ile Arg Gln Gly Pro Lys Glu Pro Phe Arg Asp Tyr Val Asp
145                 150                 155                 160

Arg Phe Tyr Lys Thr Leu Arg Ala Glu
                165

(2) INFORMATION FOR SEQ ID NO: 71:

(i) SEQUENCE CHARACTERISTICS:
            (A) LENGTH: 35 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 71:

Cys Thr Arg Pro Tyr Lys Asn Thr Arg Gln Arg Thr Gly Ile Gly Pro
1               5                   10                  15

Gly Gln Ala Leu Tyr Thr Thr His Arg Ile Ile Gly Asp Ile Arg Gln
                20                  25                  30

Ala His Cys
        35

(2) INFORMATION FOR SEQ ID NO: 72:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 72:

Arg Val Leu Ala Val Glu Arg Tyr Leu Gln Asp Gln Gln Leu Leu Gly
1               5                   10                  15

```
Ile Trp Gly Cys Ser Gly Lys His Ile Cys Thr Thr Thr Val Pro Trp
            20                  25                  30

Asn Ser Ser Trp Ser
            35

(2) INFORMATION FOR SEQ ID NO: 73:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

Cys Thr Arg Pro Asn Asn Asn Thr Arg Lys Ser Ile Arg Ile Gln Arg
1               5                   10                  15

Gly Pro Gly Arg Ala Phe Val Thr Ile Gly Lys Ile Gly Asn Met Arg
            20                  25                  30

Gln Ala His Cys
            35

(2) INFORMATION FOR SEQ ID NO: 74:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Trp
            20                  25                  30

Asn Ala Ser Trp Ser
            35

(2) INFORMATION FOR SEQ ID NO: 75:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 75:

Cys Thr Arg Pro Asn Asn Asn Thr Arg Asn Arg Ile Ser Ile Gln Arg
1               5                   10                  15

Gly Pro Gly Arg Ala His Val Thr Thr Lys Gln Ile Ile Gly Asp Ile
            20                  25                  30

Arg Gln Ala His Cys
            35

(2) INFORMATION FOR SEQ ID NO: 76:

(i) SEQUENCE CHARACTERISTICS:
        (A) LENGTH: 37 amino acids
        (B) TYPE: amino acid
```

(C) STRANDEDNESS: single
           (D) TOPOLOGY: linear (ii) MOLECULE TYPE: peptide (xi) SEQUENCE DESCRIPTION: SEQ ID NO: 76:

Arg Val Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Thr Val Pro Trp
            20                  25                  30

Asn Ala Ser Trp Ser
        35

(2) INFORMATION FOR SEQ ID NO: 77:

(i) SEQUENCE CHARACTERISTICS:
            (A) LENGTH: 34 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 77:

Cys Ala Arg Pro Tyr Gln Asn Thr Arg Gln Arg Thr Pro Ile Gly Leu
1               5                   10                  15

Gly Gln Ser Leu Tyr Thr Thr Arg Ser Arg Ser Ile Ile Gly Gln Ala
            20                  25                  30

His Cys (2) INFORMATION FOR SEQ ID NO: 78:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 78:

Arg Ile Leu Ala Val Glu Arg Tyr Leu Lys Asp Gln Gln Leu Leu Gly
1               5                   10                  15

Ile Trp Gly Cys Ser Gly Lys His Ile Cys Thr Thr Asn Val Pro Trp
            20                  25                  30

Asn Ser Ser Trp Ser
        35

(2) INFORMATION FOR SEQ ID NO: 79:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 79:

Cys Thr Arg Pro Gly Asn Asn Thr Arg Arg Gly Ile His Phe Gly Pro
1               5                   10                  15

Gly Gln Ala Leu Tyr Thr Thr Gly Val Gly Asp Ile Arg Arg Ala Tyr
            20                  25                  30

Cys (2) INFORMATION FOR SEQ ID NO: 80:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

```
Arg Val Leu Ala Val Glu Arg Tyr Leu Gln Asp Gln Arg Leu Leu Gly
 1               5                  10                  15

Met Trp Gly Cys Ser Gly Lys His Ile Cys Thr Thr Phe Val Pro Trp
            20                  25                  30

Asn Ser Ser Trp Ser
            35
```

(2) INFORMATION FOR SEQ ID NO: 81:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

```
Cys Ser Arg Pro Tyr Asn Thr Arg Lys Asn Ile Arg Arg Tyr Ser Ile
 1               5                  10                  15

Gly Ser Gly Gln Ala Phe Tyr Val Thr Gly Lys Ile Gly Asp Ile Arg
            20                  25                  30

Gln Ala His Cys
            35
```

(2) INFORMATION FOR SEQ ID NO: 82:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

```
Arg Val Leu Ala Val Glu Arg Tyr Leu Gln Asp Gln Gln Leu Leu Gly
 1               5                  10                  15

Ile Trp Gly Cys Ser Gly Lys Leu Ile Cys Thr Thr Thr Val Pro Trp
            20                  25                  30

Asn Ser Ser Trp Ser
            35
```

(2) INFORMATION FOR SEQ ID NO: 83:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

Cys His Arg Pro Gly Asn Asn Thr Arg Gly Glu Val Gln Ile Gly Pro
1               5                   10                  15

Gly Met Thr Phe Tyr Asn Ile Glu Asn Val Val Gly Asp Thr Arg Ser
                20                  25                  30

Ala Tyr Cys
        35

(2) INFORMATION FOR SEQ ID NO: 84:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 84:

Arg Leu Leu Ala Val Glu Arg Tyr Leu Gln Asp Gln Gln Ile Leu Gly
1               5                   10                  15

Leu Trp Gly Cys Ser Gly Lys Ala Val Cys Tyr Thr Thr Val Pro Trp
                20                  25                  30

Asn Asn Ser Trp Pro
        35

(2) INFORMATION FOR SEQ ID NO: 85:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

Cys Glu Arg Pro Gln Ile Asp Ile Gln Glu Met Arg Ile Gly Pro Met
1               5                   10                  15

Ala Trp Tyr Ser Met Gly Ile Gly Gly Thr Ala Gly Asn Ser Ser Arg
                20                  25                  30

Gln Ala Tyr Cys
        35

(2) INFORMATION FOR SEQ ID NO: 86:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Arg Leu Leu Ala Leu Glu Thr Leu Leu Gln Asn Gln Gln Leu Leu Ser
1               5                   10                  15

Leu Trp Gly Cys Lys Gly Lys Leu Val Cys Tyr Thr Ser Val Lys Trp
                20                  25                  30

Asn Arg Thr Trp Ile
        35

(2) INFORMATION FOR SEQ ID NO: 87:

(i) SEQUENCE CHARACTERISTICS:
    (A) LENGTH: 36 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 87:

Cys Ile Arg Glu Gly Ile Ala Glu Val Gln Asp Ile Tyr Thr Gly Pro
1               5                   10                  15

Met Arg Trp Arg Ser Met Thr Leu Ile Arg Ser Asn Asn Thr Ser Arg
            20                  25                  30

Val Ala Tyr Cys
        35

(2) INFORMATION FOR SEQ ID NO: 88:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

Arg Leu Gln Ala Leu Glu Thr Leu Ile Gln Asn Gln Gln Arg Leu Asn
1               5                   10                  15

Leu Trp Gly Cys Lys Gly Lys Leu Ile Cys Tyr Thr Ser Val Lys Trp
            20                  25                  30

Asn Arg Thr Trp Ile
        35

(2) INFORMATION FOR SEQ ID NO: 89:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 89:

Cys Glu Arg Pro Gly Asn Gln Thr Ile Gln Lys Ile Met Ala Gly Pro
1               5                   10                  15

Met Ala Trp Tyr Ser Met Ala Leu Ser Asn Thr Lys Gly Asp Thr Arg
            20                  25                  30

Ala Ala Tyr Cys
        35

(2) INFORMATION FOR SEQ ID NO: 90:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

Arg Leu Leu Ala Leu Glu Thr Phe Ile Gln Asn Gln Gln Leu Leu Asn
1               5                   10                  15

Leu Trp Gly Cys Lys Asn Arg Leu Ile Cys Tyr Thr Ser Val Lys Trp
                20                  25                  30

Asn Lys Thr Trp Gly
         35

(2) INFORMATION FOR SEQ ID NO: 91:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 91:

Cys Xaa Arg Xaa Xaa Xaa Xaa Xaa Xaa Xaa Ile Xaa Xaa Xaa Xaa
1               5                   10                  15

Gly Pro Met Xaa Trp Xaa Ser Met Xaa Xaa Xaa Xaa Xaa Xaa Xaa
                20                  25                  30

Xaa Xaa Ser Arg Xaa Ala Xaa Cys
         35                  40

(2) INFORMATION FOR SEQ ID NO: 92:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 92:

Arg Leu Xaa Ala Leu Glu Thr Xaa Xaa Gln Asn Gln Gln Xaa Leu Xaa
1               5                   10                  15

Leu Trp Gly Cys Xaa Xaa Xaa Xaa Xaa Cys Tyr Thr Ser Val Xaa Trp
                20                  25                  30

Asn Xaa Thr Trp Xaa
         35

(2) INFORMATION FOR SEQ ID NO: 93:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 93:

Cys Val Arg Pro Gly Asn Asn Ser Val Lys Glu Ile Lys Ile Gly Pro
1               5                   10                  15

Met Ala Trp Tyr Ser Met Gln Ile Glu Arg Glu Gly Lys Gly Ala Asn
                20                  25                  30

Ser Arg Thr Ala Phe Cys
         35

(2) INFORMATION FOR SEQ ID NO: 94:

(i) SEQUENCE CHARACTERISTICS:
        (A) LENGTH: 37 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 94:

Arg Leu Leu Ala Leu Glu Thr Leu Met Gln Asn Gln Gln Leu Leu Asn
1               5                   10                  15

Leu Trp Gly Cys Arg Gly Lys Ala Ile Cys Tyr Thr Ser Val Gln Trp
            20                  25                  30

Asn Glu Thr Trp Gly
        35

(2) INFORMATION FOR SEQ ID NO: 95:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 95:

CAGGGACAAA TGGTACATCA GGCCATCTCC CCCAGAACTT TATATGTATG GGTAAAGGCA        60

GTAGAAGAAA AGGCCTTTAA CCCTGAAATT ATCCCTATGT TTATGGCACT ATCAGAAGGA       120

GCTGTTCCCT ATGATATCAA TGTTATGCTA AATGCCATAG GAGGACACCA AGGGGCTTTA       180

CAAGTATTAA AGGAAGTAAT CAATGATGAA GCAGCAGACT GGGATAGAGC TCACCCACAA       240

CAGGCAGGGC CGTTACCACC AGGGCAGATA AGGGAACCAA CAGGAAGTGA CATTGCTGGA       300

ACAACTAGCA CACAGCAAGA GCAAATTCTC TGGACTACTA GGGCAGGTAA CCCTATCCCA       360

GTTGGAGACA TCTATAGGAA ATGGATAGTG TTGGGTCTAA ACAAAATGGT AAAAATGTAT       420

AGTCCAGTGA GCATCTTAGA TATTAGGCAG GGACCAAAAG AACCATTTAG AGATTATGTA       480

GACAGGTTCT ACAAAACATT AAGAGCTGAG CAG                                    513

(2) INFORMATION FOR SEQ ID NO: 96:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 96:

Gln Gly Gln Met Val His Gln Ala Leu Ser Pro Arg Thr Leu Asn Ala
1               5                   10                  15

Trp Val Lys Ala Val Glu Glu Lys Ala Phe Asn Pro Glu Ile Ile Pro
            20                  25                  30

Met Phe Met Ala Leu Ser Glu Gly Ala Val Pro Tyr Asp Ile Asn Val
        35                  40                  45

Met Leu Asn Ala Ile Gly Gly His Gln Gly Ala Leu Gln Val Leu Lys
    50                  55                  60

Glu Val Ile Asn Asp Glu Ala Ala Asp Trp Asp Arg Ala His Pro Gln
65                  70                  75                  80

Gln Ala Gly Pro Leu Pro Pro Gly Gln Ile Arg Glu Pro Thr Gly Ser
                85                  90                  95

Asp Ile Ala Gly Thr Thr Ser Thr Gln Gln Glu Gln Ile Leu Trp Thr
            100                 105                 110

```
Thr Arg Ala Gly Asn Pro Ile Pro Val Gly Asp Ile Tyr Arg Lys Trp
        115                 120                 125

Ile Val Leu Gly Leu Asn Lys Met Val Lys Met Tyr Ser Pro Val Ser
        130                 135                 140

Ile Leu Asp Ile Arg Gln Gly Pro Lys Glu Pro Phe Arg Asp Tyr Val
145                 150                 155                 160

Asp Arg Phe Tyr Lys Thr Leu Arg Ala Glu Gln
                165                 170
```

(2) INFORMATION FOR SEQ ID NO: 97:

(i) SEQUENCE CHARACTERISTICS:
        (A) LENGTH: 525 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 97:

```
ATTCCAATAC ACTATTGTGC TCCAGCAGGA TATGCTATCT TTAAATGCAA CAACGAGGAG      60

TTTACTGGAA AAGGCCCATG TAACAACATT TCAGTAGTTA CCTGTACACA GGGTATCAAG     120

CCAACAGTAA GCACTCATCT AATATTCAAT GGGACAATCT CTGAAAGAAA AATAAGAATT     180

ATGGGAAAGA ACATCTCGAG CAACTCAGGT AATATCCTAG TGACCCTAAA TTCTACTATA     240

AACATGACCT GTGTGAGGCC AGGAAATAAT TCAGTACAGG AGATAAAAAT AGGTCCAATG     300

GCTTGGTACA GTATGCAAAT TGAGCGAGAG GGAAAAGGAG CAAATTCAAG AACAGCTTTT     360

TGTACCTATA ATGCCACGGA CTGGAGAAAA ACCTTGCAAG GGATAGCTGA AAGGTATTTA     420

GAACTTGTAA ATAAAACAAG TCCGACTGAA ATAATGTTCA ATAAAAGCAA TGGTGGAGAT     480

GCAGAAATAA CCCGTTTGCA TTTTAACTGT CATGGAGAAT TCTTT                     525
```

(2) INFORMATION FOR SEQ ID NO: 98:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

```
Ile Pro Ile His Tyr Cys Ala Pro Ala Gly Tyr Ala Ile Phe Lys Cys
1               5                   10                  15

Asn Asn Glu Glu Phe Thr Gly Lys Gly Pro Cys Asn Asn Ile Ser Val
                20                  25                  30

Val Thr Cys Thr Gln Gly Ile Lys Pro Thr Val Ser Thr His Leu Ile
            35                  40                  45

Phe Asn Gly Thr Ile Ser Glu Arg Lys Ile Arg Ile Met Gly Lys Asn
        50                  55                  60

Ile Ser Ser Asn Ser Gly Asn Ile Leu Val Thr Leu Asn Ser Thr Ile
65                  70                  75                  80

Asn Met Thr Cys Val Arg Pro Gly Asn Asn Ser Val Gln Glu Ile Lys
                85                  90                  95

Ile Gly Pro Met Ala Trp Tyr Ser Met Gln Ile Glu Arg Glu Gly Lys
            100                 105                 110

Gly Ala Asn Ser Arg Thr Ala Phe Cys Thr Tyr Asn Ala Thr Asp Trp
```

```
            115                 120                 125
Arg Lys Thr Leu Gln Gly Ile Ala Glu Arg Tyr Leu Glu Leu Val Asn
        130                 135                 140

Lys Thr Ser Pro Thr Glu Ile Met Phe Asn Lys Ser Asn Gly Gly Asp
145                 150                 155                 160

Ala Glu Ile Thr Arg Leu His Phe Asn Ser Cys Gly Glu Phe Phe
                165                 170                 175
```

(2) INFORMATION FOR SEQ ID NO: 99:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 99:

```
ATAGTGCAAC AGCAGGACAA CCTGCTGAGA GCAATACAGG CCCAGCAACA TCTGCTGAGG      60

TTATCTGTAT GGGGTATTAG ACAACTCCGA GCTCGCCTGC TAGCCTTAGA AACCCTTATG     120

CAGAATCAGC AACTCCTAAA CCTGTGGGGT TGTAGAGGAA AAGCAATCTG CTACACATCA     180

GTACAATGGA ATGAAACATG GGAGGAAAT GACTCAATTT GGGACAGGTT AACATGGCAG      240

CAATGGGATC AACAGATAGC CAATGTAAGC TCTTTTATAT ATGACAAAAT ACAAGAAGCA     300

CAAGAACAAC AA                                                        312
```

(2) INFORMATION FOR SEQ ID NO: 100:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 100:

```
Ile Val Gln Gln Gln Asp Asn Leu Leu Arg Ala Ile Gln Ala Gln Gln
1               5                   10                  15

His Leu Leu Arg Leu Ser Val Trp Gly Ile Arg Gln Leu Arg Ala Arg
                20                  25                  30

Leu Leu Ala Leu Glu Thr Leu Met Gln Asn Gln Gln Leu Leu Asn Leu
            35                  40                  45

Trp Gly Cys Arg Gly Lys Ala Ile Cys Tyr Thr Ser Val Gln Trp Asn
        50                  55                  60

Glu Thr Trp Gly Gly Asn Asp Ser Ile Trp Asp Arg Leu Thr Trp Gln
65                  70                  75                  80

Gln Trp Asp Gln Gln Ile Ala Asn Val Ser Ser Phe Ile Tyr Asp Lys
                85                  90                  95

Ile Gln Glu Ala Gln Glu Gln Gln
            100
```

(2) INFORMATION FOR SEQ ID NO: 101:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 101:

Arg Leu Leu Ala Leu Glu Thr Phe Ile Gln Asn Gln Gln Leu Leu Asn
1               5                   10                  15

Leu Trp Gly Cys Lys Asn Arg Leu Ile Cys Tyr Thr Ser Val Lys Trp
            20                  25                  30

Asn Lys Thr
        35

(2) INFORMATION FOR SEQ ID NO: 102:

(i) SEQUENCE CHARACTERISTICS:
        (A) LENGTH: 877 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 102:

Met Thr Ala Ile Met Lys Ala Met Gly Lys Arg Asn Arg Lys Leu Gly
1               5                   10                  15

Ile Trp Cys Leu Ile Leu Ala Leu Ile Ile Pro Cys Leu Ser Cys Asn
            20                  25                  30

Gln Leu Tyr Ala Thr Val Tyr Ser Gly Val Pro Val Trp Glu Asp Ala
            35                  40                  45

Lys Pro Thr Leu Phe Cys Ala Ser Asp Ala Asn Leu Thr Ser Thr Glu
        50              55                  60

Gln His Asn Ile Trp Ala Thr Gln Ala Cys Val Pro Thr Asp Pro Ser
65                  70                  75                  80

Pro Asn Glu Tyr Glu Leu Lys Asn Val Thr Gly Lys Phe Asn Ile Trp
            85                  90                  95

Lys Asn Tyr Ile Val Asp Gln Met His Glu Asp Ile Ile Asp Leu Trp
            100                 105                 110

Asp Gln Ser Leu Lys Pro Cys Val Gln Met Thr Phe Leu Cys Val Gln
            115                 120                 125

Met Asn Cys Thr Asp Ile Lys Asn Ser Ile Asn Thr Thr Asn Ser Pro
        130                 135                 140

Leu Asn Ser Asn Asn Thr Lys Glu Val Lys Gln Cys Asp Phe Asn Val
145                 150                 155                 160

Thr Thr Val Leu Lys Asp Lys Gln Glu Lys Lys Gln Ala Leu Phe Tyr
            165                 170                 175

Val Thr Asp Leu Val Lys Ile Asn Ala Thr Ser Asn Glu Thr Met Tyr
            180                 185                 190

Arg Leu Ile Asn Cys Asn Ser Thr Thr Ile Arg Gln Ala Cys Pro Lys
            195                 200                 205

Val Ser Phe Glu Pro Ile Pro Ile His Tyr Cys Ala Pro Ala Gly Cys
        210                 215                 220

Ala Ile Phe Lys Cys Asn Glu Thr Gly Phe Asn Gly Thr Gly Leu Cys
225                 230                 235                 240

Lys Asn Val Thr Val Val Thr Cys Thr His Gly Ile Lys Pro Thr Val
            245                 250                 255

Ser Thr Gln Leu Ile Leu Asn Gly Thr Leu Ser Lys Gly Asn Ile Thr
            260                 265                 270

Ile Met Gly Lys Asn Ile Ser Asp Ser Gly Glu Asn Ile Leu Ile Thr
            275                 280                 285

```
Leu Asn Thr Asn Ile Thr Ile Ala Cys Glu Arg Pro Gly Asn Gln Thr
290                 295                 300

Ile Gln Lys Ile Met Ala Gly Pro Met Ala Trp Tyr Ser Met Ala Leu
305                 310                 315                 320

Ser Asn Thr Lys Gly Asp Thr Arg Ala Ala Tyr Cys Asn Tyr Ser Ala
                325                 330                 335

Thr Asp Trp Asn Lys Ala Leu Lys Asn Ile Thr Glu Arg Tyr Leu Glu
            340                 345                 350

Leu Val Glu Tyr Asn Gln Thr Asp Val Thr Met Lys Phe Gly Asn His
        355                 360                 365

Ser Gly Glu Asp Ala Glu Val Thr Asn Phe Phe Asn Cys His Gly
    370                 375                 380

Glu Phe Phe Tyr Cys Asn Thr Asn Arg Leu Phe Asn His Thr Phe Ser
385                 390                 395                 400

Cys Lys Lys Asn Met Thr Asn Asn Lys Ile Asn Cys Thr Asn Ile Ser
                405                 410                 415

Asn Asn Ser Asn Gly Thr Gln Ala Ile Pro Cys Arg Leu Arg Gln Val
                420                 425                 430

Val Arg Asp Trp Met Arg Gly Ser Gly Leu Tyr Ala Pro Pro Ile
                435                 440                 445

Pro Gly Asn Leu Val Cys Arg Ser Asn Ile Thr Gly Met Ile Leu Gln
    450                 455                 460

Leu Asp Thr Pro Trp Asn Lys Thr His Pro Asn Ser Thr Thr Leu Arg
465                 470                 475                 480

Pro Gly Gly Gly Asp Met Lys Asp Ile Trp Arg Thr Gln Leu Phe Lys
                485                 490                 495

Tyr Lys Val Val Arg Val Lys Pro Phe Ser Val Ala Pro Thr Lys Ile
                500                 505                 510

Ala Arg Pro Thr Ile Gly Thr Arg Ser His Arg Glu Lys Arg Ala Ala
            515                 520                 525

Gly Leu Ala Met Leu Phe Leu Gly Ile Leu Ser Ala Ala Gly Ser Thr
    530                 535                 540

Met Gly Ala Ala Ala Thr Ala Leu Thr Val Arg Thr Gln His Leu Ile
545                 550                 555                 560

Lys Gly Ile Val Gln Gln Asp Asn Leu Leu Arg Ala Ile Gln Ala
                565                 570                 575

Gln Gln His Leu Leu Arg Pro Ser Val Trp Gly Ile Arg Gln Leu Arg
        580                 585                 590

Ala Arg Leu Leu Ala Leu Glu Thr Phe Ile Gln Asn Gln Leu Leu
        595                 600                 605

Asn Leu Trp Gly Cys Lys Asn Arg Leu Ile Cys Tyr Thr Ser Val Lys
    610                 615                 620

Trp Asn Lys Thr Trp Gly Gly Asp Asn Glu Ser Ile Trp Asp Glu Leu
625                 630                 635                 640

Thr Trp Gln Gln Trp Asp Gln Gln Ile Asn Asn Val Ser Ser Phe Ile
                645                 650                 655

Tyr Glu Lys Ile Gln Glu Ala Gln Glu Gln Gln Glu Lys Asn Glu Lys
                660                 665                 670

Glu Leu Leu Glu Leu Asp Glu Trp Ala Ser Ile Trp Asn Trp Leu Asp
        675                 680                 685

Ile Thr Lys Trp Leu Trp Tyr Ile Lys Ile Ala Ile Ile Val Gly
    690                 695                 700
```

Ala Leu Ile Gly Val Arg Val Met Ile Val Leu Asn Leu Val Lys
705                 710                 715                 720

Asn Ile Arg Gln Gly Tyr Gln Pro Leu Ser Leu Gln Ile Pro Ile Gln
            725                 730                 735

Gln Gln Ala Glu Val Gly Thr Pro Gly Gly Thr Gly Glu Gly Gly Gly
            740                 745                 750

Asp Glu Asp Arg Arg Trp Thr Pro Leu Pro Gln Gly Phe Leu His
            755                 760                 765

Leu Leu Tyr Thr Asp Leu Arg Thr Ile Ile Leu Trp Ile Tyr His Leu
770                 775                 780

Leu Ser Asn Leu Ala Ser Glu Ile Gln Lys Leu Ile Arg His Leu Gly
785                 790                 795                 800

Leu Gly Leu Trp Ile Ile Gly Gln Arg Thr Ile Glu Ala Cys Arg Leu
            805                 810                 815

Phe Lys Ala Ile Ile Gln Tyr Trp Leu Gln Glu Leu Gln Thr Ser Ala
            820                 825                 830

Thr Asn Leu Leu Asp Thr Val Ala Val Ala Val Ala Asn Trp Thr Asp
            835                 840                 845

Ser Thr Ile Leu Gly Ile Gln Ser Ile Gly Arg Gly Ile Leu Asn Ile
850                 855                 860

Pro Arg Arg Ile Arg Gln Gly Leu Glu Arg Leu Leu Leu
865                 870                 875

(2) INFORMATION FOR SEQ ID NO: 103:

(i) SEQUENCE CHARACTERISTICS:
        (A) LENGTH: 861 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 103:

Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
            50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
            115                 120                 125

Leu Lys Cys Thr Asp Leu Gly Asn Ala Thr Asn Thr Asn Ser Ser Asn
130                 135                 140

Thr Asn Ser Ser Ser Gly Glu Met Met Met Glu Lys Gly Glu Ile Lys
145                 150                 155                 160

Asn Cys Ser Phe Asn Ile Ser Thr Ser Ile Arg Gly Lys Val Gln Lys
                165                 170                 175

-continued

```
Glu Tyr Ala Phe Phe Tyr Lys Leu Asp Ile Ile Pro Ile Asp Asn Asp
            180                 185                 190

Thr Thr Ser Tyr Thr Leu Thr Ser Cys Asn Thr Ser Val Ile Thr Gln
            195                 200                 205

Ala Cys Pro Lys Val Ser Phe Glu Pro Ile Pro Ile His Tyr Cys Ala
            210                 215                 220

Pro Ala Gly Phe Ala Ile Leu Lys Cys Asn Asn Lys Thr Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Ala Asn Phe Thr Asp Asn Ala Lys Thr
            275                 280                 285

Ile Ile Val Gln Leu Asn Gln Ser Val Glu Ile Asn Cys Thr Arg Pro
            290                 295                 300

Asn Asn Asn Thr Arg Lys Ser Ile Arg Ile Gln Arg Gly Pro Gly Arg
305                 310                 315                 320

Ala Phe Val Thr Ile Gly Lys Ile Gly Asn Met Arg Gln Ala His Cys
                325                 330                 335

Asn Ile Ser Arg Ala Lys Trp Asn Ala Thr Leu Lys Gln Ile Ala Ser
            340                 345                 350

Lys Leu Arg Glu Gln Phe Gly Asn Asn Lys Thr Ile Ile Phe Lys Gln
            355                 360                 365

Ser Ser Gly Gly Asp Pro Glu Ile Val Thr His Ser Phe Asn Cys Gly
            370                 375                 380

Gly Glu Phe Phe Tyr Cys Asn Ser Thr Gln Leu Phe Asn Ser Thr Trp
385                 390                 395                 400

Phe Asn Ser Thr Trp Ser Thr Glu Gly Ser Asn Asn Thr Glu Gly Ser
                405                 410                 415

Asp Thr Ile Thr Leu Pro Cys Arg Ile Lys Gln Phe Ile Asn Met Trp
            420                 425                 430

Gln Glu Val Gly Lys Ala Met Tyr Ala Pro Pro Ile Ser Gly Gln Ile
            435                 440                 445

Arg Cys Ser Ser Asn Ile Thr Gly Leu Leu Leu Thr Arg Asp Gly Gly
            450                 455                 460

Asn Asn Asn Asn Gly Ser Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
            500                 505                 510

Arg Glu Lys Arg Ala Val Gly Ile Gly Ala Leu Phe Leu Gly Phe Leu
            515                 520                 525

Gly Ala Ala Gly Ser Thr Met Gly Ala Arg Ser Met Thr Leu Thr Val
            530                 535                 540

Gln Ala Arg Gln Leu Leu Ser Gly Ile Val Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Ile Leu Ala Val Glu Arg Tyr Leu
            580                 585                 590

Lys Asp Gln Gln Leu Leu Gly Ile Trp Gly Cys Ser Gly Lys Leu Ile
```

-continued

```
        595                 600                 605

Cys Thr Thr Ala Val Pro Trp Asn Ala Ser Trp Ser Asn Lys Ser Leu
    610                 615                 620

Glu Gln Ile Trp Asn Asn Met Thr Trp Met Glu Trp Asp Arg Glu Ile
625                 630                 635                 640

Asn Asn Tyr Thr Ser Leu Ile His Ser Leu Ile Glu Glu Ser Gln Asn
                645                 650                 655

Gln Gln Glu Lys Asn Glu Gln Glu Leu Leu Glu Leu Asp Lys Trp Ala
            660                 665                 670

Ser Leu Trp Asn Trp Phe Asn Ile Thr Asn Trp Leu Trp Tyr Ile Lys
        675                 680                 685

Ile Phe Ile Met Ile Val Gly Gly Leu Val Gly Leu Arg Ile Val Phe
    690                 695                 700

Ala Val Leu Ser Ile Val Asn Arg Val Arg Gln Gly Tyr Ser Pro Leu
705                 710                 715                 720

Ser Phe Gln Thr His Leu Pro Thr Pro Arg Gly Pro Asp Arg Pro Glu
                725                 730                 735

Gly Ile Glu Glu Glu Gly Gly Glu Arg Asp Arg Asp Arg Ser Ile Arg
            740                 745                 750

Leu Val Asn Gly Ser Leu Ala Leu Ile Trp Asp Asp Leu Arg Ser Leu
        755                 760                 765

Cys Leu Phe Ser Tyr His Arg Leu Arg Asp Leu Leu Leu Ile Val Thr
    770                 775                 780

Arg Ile Val Glu Leu Leu Gly Arg Arg Gly Trp Glu Ala Leu Lys Tyr
785                 790                 795                 800

Trp Trp Asn Leu Leu Gln Tyr Trp Ser Gln Glu Leu Lys Asn Ser Ala
                805                 810                 815

Val Ser Leu Leu Asn Ala Thr Ala Ile Ala Val Ala Glu Gly Thr Asp
            820                 825                 830

Arg Val Ile Glu Val Val Gln Gly Ala Cys Arg Ala Ile Arg His Ile
        835                 840                 845

Pro Arg Arg Ile Arg Gln Gly Leu Glu Arg Ile Leu Leu
    850                 855                 860
```

What is claimed is:

1. A purified HIV-1 DUR isolate, which is the isolate deposited at C.N.C.M. under the accession no. I-1542.

2. A purified nucleic acid comprising the sequence of SEQ ID NO:63.

3. A purified nucleic acid comprising the sequence of SEQ ID NO:64.

4. A purified HIV-1 Env peptide comprising a sequence selected from the group consisting of:

CysValArgProGlyAsnAsnSerVal-LysGluIleLysIleGlyProMetAla-TrpTyrSerMetGlnIleGluArgGluG-lyLysGlyAlaAsnSerArgThrAlaPheCys (SEQ ID NO:93);

CysLysAsnArgLeuIleCys (SEQ ID NO:5);

ArgLeuLeuAlaLeuGluThrPheIle-GlnAsnTrpTrpLeuLeuAsnLeuTrpG-lyCysLysAsnArgLeuIleCys (SEQ ID NO:6);

ArgAlaArgLeuLeuAlaLeuGluThr-PheIleGlnAsnGlnGlnLeuLeuAsn-LeuTrpGlyCysLysAsnArgLeuIle-CysTyrThrSerValLysTrpAsnLysThr (SEQ ID NO:7);

LysGluIleLysIle (SEQ ID NO:23);

GluArgGluGlyLysGlyAlaAsn (SEQ ID NO:24);

CysValArgProGlyAsnAsnSerValLysGluIleLysIle (SEQ ID NO:25);

GlnIleGluArgGluGlyLysGlyAlaAsnSerArg (SEQ ID NO:26);

ArgLeuLeuAlaLeuGluThrLeuMetGlnAsnGlnGlnLeu (SEQ ID NO:29);

LeuAsnLeuTrpGlyCysArg-GlyLysAlaIleCysTyrThrSerVal-GlnTrpAsnGluThrTrpGly (SEQ ID NO:30);

CysArgGlyLysAlaIle (SEQ ID NO:31);

SerValGlnTrpAsn (SEQ ID NO:32);

ArgLeuLeuAlaLeuGluThrLeuMet-GlnAsnGlnGlnLeuLeuAsnLeuTrpG-lyCysArgGlyLysAlaIleCysTyrThrSer (SEQ ID NO:33);

GlnAsnGlnGlnLeuLeuAsnLeuTrpG-lyCysArgGlyLysAlaIleCysTyrThrSerValGlnTrpAsn (SEQ ID NO:34);

ThrPheIleGlnAsn (SEQ ID NO:40); and

TrpGlyCysLysAsnArg (SEQ ID NO:41).

5. An oligonucleotide primer selected from the group consisting of:

ATTCCAATACACTATTGTGCTCCA (SEQ ID NO:42);

AAAGAATTCTCCATGACTGTTAAA (SEQ ID NO:43);

GGTATAGTGCAACAGCAGGACAAC (SEQ ID NO:44);

AGAGGCCCATTCATCTAACTC (SEQ ID NO:45); and sequences complementary to these sequences.

6. A probe for HIV group O, wherein said probe is at least 90% identical to SEQ ID NO:63.

7. A purified HIV-1 isolate comprising Env protein, wherein said Env protein comprises a sequence selected from the group consisting of:

CysValArgProGlyAsnAsnSerVal-LysGluIleLysIleGlyProMetAla-TrpTyrSerMetGlnIleGluArgGluGlyLysGlyAlaAsnSerArgThrAlaPheCys (SEQ ID NO:93);

CysLysAsnArgLeuIleCys (SEQ ID NO:5);

ArgLeuLeuAlaLeuGluThr-PheIleGlnAsnTrpTrpLeuLeuAsn-LeuTrpGlyCysLysAsnArgLeuIleCys (SEQ ID NO:6);

ArgAlaArgLeuLeuAlaLeuGluThr-PheIleGlnAsnGlnGlnLeuLeuAsn-LeuTrpGlyCysLysAsnArgLeuIle-CysTyrThrSerValLysTrpAsnLysThr (SEQ ID NO:7);

LysGluIleLysIle (SEQ ID NO:23);

GluArgGluGlyLysGlyAlaAsn (SEQ ID NO:24);

CysValArgProGlyAsnAsnSerValLysGluIleLysIle (SEQ ID NO:25);

GlnIleGluArgGluGlyLysGlyAlaAsnSerArg (SEQ ID NO:26);

ArgLeuLeuAlaLeuGluThrLeuMetGlnAsnGlnGlnLeu (SEQ ID NO:29);

LeuAsnLeuTrpGlyCysArg-GlyLysAlaIleCysTyrThrSerVal-GlnTrpAsnGluThrTrpGly (SEQ ID NO:30);

CysArgGlyLysAlaIle (SEQ ID NO:31);

SerValGlnTrpAsn (SEQ ID NO:32);

ArgLeuLeuAlaLeuGluThrLeuMet-GlnAsnGlnGlnLeuLeuAsnLeuTrpGlyCysArgGlyLysAlaIleCysTyrThrSer (SEQ ID NO:33);

GlnAsnGlnGlnLeuLeuAsnLeuTrpGlyCysArgGlyLysAlaIleCysTyrThrSerValGlnTrpAsn (SEQ ID NO:34);

ThrPheIleGlnAsn (SEQ ID NO:40); and

TrpGlyCysLysAsnArg (SEQ ID NO:41).

8. A probe for HIV group O, wherein said probe encodes an Env peptide comprising a sequence selected from the group consisting of:

CysValArgProGlyAsnAsnSerVal-LysGluIleLysIleGlyProMetAla-TrpTyrSerMetGlnIleGluArgGluGlyLysGlyAlaAsnSerArgThrAlaPheCys (SEQ ID NO:93);

CysLysAsnArgLeuIleCys (SEQ ID NO:5);

ArgLeuLeuAlaLeuGluThr-PheIleGlnAsnTrpTrpLeuLeuAsn-LeuTrpGlyCysLysAsnArgLeuIleCys (SEQ ID NO:6);

ArgAlaArgLeuLeuAlaLeuGluThr-PheIleGlnAsnGlnGlnLeuLeuAsn-LeuTrpGlyCysLysAsnArgLeuIle-CysTyrThrSerValLysTrpAsnLysThr (SEQ ID NO:7);

LysGluIleLysIle (SEQ ID NO:23);

GluArgGluGlyLysGlyAlaAsn (SEQ ID NO:24);

CysValArgProGlyAsnAsnSerValLysGluIleLysIle (SEQ ID NO:25);

GlnIleGluArgGluGlyLysGlyAlaAsnSerArg (SEQ ID NO:26);

ArgLeuLeuAlaLeuGluThrLeuMetGlnAsnGlnGlnLeu (SEQ ID NO:29);

LeuAsnLeuTrpGlyCysArg-GlyLysAlaIleCysTyrThrSerVal-GlnTrpAsnGluThrTrpGly (SEQ ID NO:30);

CysArgGlyLysAlaIle (SEQ ID NO:31);

SerValGlnTrpAsn (SEQ ID NO:32);

ArgLeuLeuAlaLeuGluThrLeuMet-GlnAsnGlnGlnLeuLeuAsnLeuTrpGlyCysArgGlyLysAlaIleCysTyrThrSer (SEQ ID NO:33);

GlnAsnGlnGlnLeuLeuAsnLeuTrpGlyCysArgGlyLysAlaIleCysTyrThrSerValGlnTrpAsn (SEQ ID NO:34);

ThrPheIleGlnAsn (SEQ ID NO:40); and

TrpGlyCysLysAsnArg (SEQ ID NO:41).

9. A purified HIV-1 env gene, wherein said gene encodes a polypeptide comprising a sequence selected from the group consisting of:

CysValArgProGlyAsnAsnSerVal-LysGluIleLysIleGlyProMetAla-TrpTyrSerMetGlnIleGluArgGluGlyLysGlyAlaAsnSerArgThrAlaPheCys (SEQ ID NO:93);

CysLysAsnArgLeuIleCys (SEQ ID NO:5);

ArgLeuLeuAlaLeuGluThr-PheIleGlnAsnTrpTrpLeuLeuAsn-LeuTrpGlyCysLysAsnArgLeuIleCys (SEQ ID NO:6);

ArgAlaArgLeuLeuAlaLeuGluThr-PheIleGlnAsnGlnGlnLeuLeuAsn-LeuTrpGlyCysLysAsnArgLeuIle-CysTyrThrSerValLysTrpAsnLysThr (SEQ ID NO:7);

LysGluIleLysIle (SEQ ID NO:23);

GluArgGluGlyLysGlyAlaAsn (SEQ ID NO:24);

CysValArgProGlyAsnAsnSerValLysGluIleLysIle (SEQ ID NO:25);

GlnIleGluArgGluGlyLysGlyAlaAsnSerArg (SEQ ID NO:26);

ArgLeuLeuAlaLeuGluThrLeuMetGlnAsnGlnGlnLeu (SEQ ID NO:29);

LeuAsnLeuTrpGlyCysArg-GlyLysAlaIleCysTyrThrSerVal-GlnTrpAsnGluThrTrpGly (SEQ ID NO:30);

CysArgGlyLysAlaIle (SEQ ID NO:31);

SerValGlnTrpAsn (SEQ ID NO:32);

ArgLeuLeuAlaLeuGluThrLeuMet-GlnAsnGlnGlnLeuLeuAsnLeuTrpGlyCysArgGlyLysAlaIleCysTyrThrSer (SEQ ID NO:33);

GlnAsnGlnGlnLeuLeuAsnLeuTrpGlyCysArgGlyLysAlaIleCysTyrThrSerValGlnTrpAsn (SEQ ID NO:34);

ThrPheIleGlnAsn (SEQ ID NO:40); and
TrpGlyCysLysAsnArg (SEQ ID NO:41).

10. A purified HIV-1 nucleic acid, wherein said nucleic acid encodes a polypeptide comprising a sequence selected from the group consisting of:

CysValArgProGlyAsnAsnSerVal-LysGluIleLysIleGlyProMetAla-TrpTyrSerMetGlnIleGluArgGluG-lyLysGlyAlaAsnSerArgThrAlaPheCys (SEQ ID NO:93);

CysLysAsnArgLeuIleCys (SEQ ID NO:5);

ArgLeuLeuAlaLeuGluThr-PheIleGlnAsnTrpTrpLeuLeuAsn-LeuTrpGlyCysLysAsnArgLeuIleCys (SEQ ID NO:6);

ArgAlaArgLeuLeuAlaLeuGluThr-PheIleGlnAsnGlnGlnLeuLeuAsn-LeuTrpGlyCysLysAsnArgLeuIle-CysTyrThrSerValLysTrpAsnLysThr (SEQ ID NO:7);

LysGluIleLysIle (SEQ ID NO:23);

GluArgGluGlyLysGlyAlaAsn (SEQ ID NO:24);

CysValArgProGlyAsnAsnSerValLysGluIleLysIle (SEQ ID NO:25);

GlnIleGluArgGluGlyLysGlyAlaAsnSerArg (SEQ ID NO:26);

ArgLeuLeuAlaLeuGluThrLeuMetGlnAsnGlnGlnLeu (SEQ ID NO:29);

LeuAsnLeuTrpGlyCysArg-GlyLysAlaIleCysTyrThrSerVal-GlnTrpAsnGluThrTrpGly (SEQ ID NO:30);

CysArgGlyLysAlaIle (SEQ ID NO:31);

SerValGlnTrpAsn (SEQ ID NO:32);

ArgLeuLeuAlaLeuGluThrLeuMet-GlnAsnGlnGlnLeuLeuAsnLeuTrpG-lyCysArgGlyLysAlaIleCysTyrThrSer (SEQ ID NO:33);

GlnAsnGlnGlnLeuLeuAsnLeuTrpG-lyCysArgGlyLysAlaIleCysTyrThrSerValGlnTrpAsn (SEQ ID NO:34);

ThrPheIleGlnAsn (SEQ ID NO:40); and

TrpGlyCysLysAsnArg (SEQ ID NO:41).

11. A method for the in vitro diagnosis of an infection caused by an HIV-$1_{(VAU)}$ virus, said process comprising:

(A) obtaining a biological sample comprising antibodies;

(B) contacting said sample with at least one peptide of claim 4; and (C) detecting the immunological complexes formed.

* * * * *